United States Patent
Steinbrenner et al.

(10) Patent No.: US 10,405,549 B2
(45) Date of Patent: *Sep. 10, 2019

(54) COMPOSITION OF 1,5-DIMETHYL-6-THIOXO-3-(2,2,7-TRIFLUORO-3-OXO-4-(PROP-2-YNYL)-3,4-DIHYDRO-2H-BENZO[B][1,4]OXAZIN-6-YL)-1,2,5-TRIAZINANE-2,4-DIONE

(71) Applicant: BASF SE, Ludwigshafen (DE)

(72) Inventors: Ulrich Steinbrenner, Neustadt (DE); Joerg Steuerwald, Boehl-Iggelheim (DE); Anja Simon, Weinheim (DE)

(73) Assignee: BASF SE, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/036,248

(22) PCT Filed: Oct. 28, 2014

(86) PCT No.: PCT/EP2014/073073
§ 371 (c)(1),
(2) Date: May 12, 2016

(87) PCT Pub. No.: WO2015/071087
PCT Pub. Date: May 21, 2015

(65) Prior Publication Data
US 2016/0295866 A1    Oct. 13, 2016

(30) Foreign Application Priority Data
Nov. 14, 2013  (EP) .................................... 13192898

(51) Int. Cl.
*A01N 43/84* (2006.01)
*A01N 25/32* (2006.01)
*A01N 25/12* (2006.01)
*A01N 43/64* (2006.01)
*C07D 413/04* (2006.01)

(52) U.S. Cl.
CPC ............. *A01N 43/84* (2013.01); *A01N 25/12* (2013.01); *A01N 25/32* (2013.01); *A01N 43/64* (2013.01); *C07D 413/04* (2013.01)

(58) Field of Classification Search
CPC ........ A01N 43/84; A01N 43/64; A01N 25/32; A01N 25/12; C07D 413/04
See application file for complete search history.

(56) References Cited

U.S. PATENT DOCUMENTS 9,328,101 B2 *  5/2016  Reinhard ............. C07D 413/04
9,353,095 B2 *  5/2016  Reinhard ............... A01N 43/84

FOREIGN PATENT DOCUMENTS

| WO | WO 2010/145992 | 12/2010 | |
| WO | WO 2010145992 A1 * | 12/2010 | ............. A01N 43/84 |
| WO | 2011151899 A1 | 12/2011 | |
| WO | WO 2013174693 A1 * | 11/2013 | ............. A01N 43/84 |

OTHER PUBLICATIONS

Rahman, A., et al. "Influence of particle size and type of formulation on phytotoxicity and persistence of atrazine" Weed Research, Aug. 1, 1984, p. 257-259. vol. 24, No. 4.
International Search Report dated Dec. 3, 2014, prepared in International Application No. PCT/EP2014/073073.
International Preliminary Report on Patentability dated May 17, 2016, prepared in International Application No. PCT/EP2014/073073.
European Search Report prepared in EP Application No. 13192898 dated Feb. 14, 2017.
Office Action issued in EP Application No. 14790581 dated Jun. 23, 2017.

* cited by examiner

*Primary Examiner* — Sue X Liu
*Assistant Examiner* — Andriae M Holt
(74) *Attorney, Agent, or Firm* — Brinks Gilson & Lione

(57) ABSTRACT

The present invention relates to a composition of benzoxazinone (I) comprising the benzoxazinone (I) in form of particles, wherein at most 50% per volume of the particles have a diameter below 3 μm.

18 Claims, 2 Drawing Sheets

COMPOSITION OF 1,5-DIMETHYL-6-THIOXO-3-(2,2,7-TRIFLUORO-3-OXO-4-(PROP-2-YNYL)-3,4-DIHYDRO-2H-BENZO[B][1,4]OXAZIN-6-YL)-1,2,5-TRIAZINANE-2,4-DIONE

This application is a National Stage application of International Application No. PCT/EP2014/073073, filed Oct. 28, 2014. This application also claims priority under 35U.S.C. § 119 to European Patent Application No. 13192898.8, filed Nov. 14, 2013.

One of the most common practices for controlling undesirable plant species is the use of herbicides.

In crop protection products, it is desirable in principle to increase the specificity and the reliability of the action of active compounds. In particular, it is desirable for the crop protection product to control the harmful plants effectively and, at the same time, to be tolerated by the useful plants in question. It is known that in some cases better crop plant compatibility can be achieved by joint application of specifically acting herbicides with organic active compounds, which act as antidotes or antagonists. Owing to the fact that they can reduce or even prevent damage to the crop plants, they are also referred to as safeners.

1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione, which hereinafter is also termed as "benzoxazinone (I)", is the herbicidally active substance of the formula I

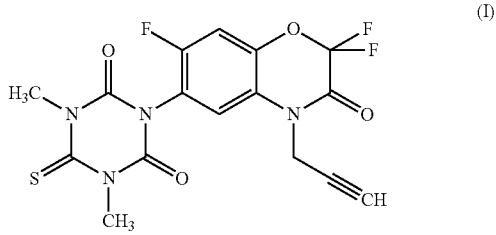 [SMILES: C#CCN1C(=O)C(F)(F)Oc2cc(F)c(-n3c(=O)n(C)c(=S)n(C)c3=O)cc21]

Benzoxazinone (I) and a process for its production are known from WO 2010/145992. This process yields benzoxazinone (I) as an amorphous solid.

However, the herbicidal properties of the known benzoxazinone (I) with regard to the harmful plants, and their compatibility with crop plants are not always entirely satisfactory.

It is therefore an object of the present invention to provide a herbicidal benzoxazinone (I), which is highly active against unwanted harmful plants, and, at the same time, has good compatibility with useful plants.

This and further objects are achieved by the composition of benzoxazinone (I) as defined below.

Surprisingly it has been found that the benzoxazinone (I) applied in the form of particles, wherein at most 50% per volume of the particles have a diameter below 3 μm, exhibits reduced phytotoxicity.

Accordingly, the present invention relates to a composition of benzoxazinone (I),

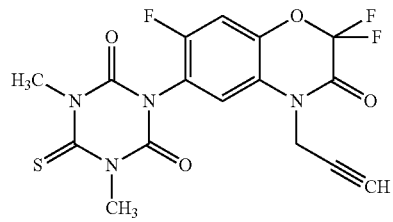

comprising the benzoxazinone (I) in form of particles, wherein at most 50% per volume of the particles have a diameter below 3 μm.

This composition of benzoxazinone of formula (I) comprising the benzoxazinone of formula (I) in form of particles wherein at most 50% per volume of the particles have a diameter below 3 μm is hereinafter also described and termed as "composition of benzoxazinone (I) comprising the benzoxazinone (I) in form of particles" or as "composition A".

The present invention also provides plant protection agents comprising a herbicidally active amount of the composition of benzoxazinone (I) as described herein (composition A) and at least one inert liquid and/or solid carrier and, if appropriate, at least one surface-active substance.

The present invention also provides a method of safening crops from phytotoxic injury from application of a herbicidally effective amount of the composition of benzoxazinone (I) as described herein (composition A).

The present invention also provides a method of controlling undesired vegetation, which comprises allowing an herbicidal active amount of the composition of benzoxazinone (I) as described herein (composition A), to act on plants, their environment or on seed.

The present invention further relates to herbicidal combinations comprising at least the composition A (as component A) and at least one further compound selected from herbicidal compounds (as component B) and safeners (as component C).

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

The particle diameter, as referred herein, is the volume average particle diameter according to static laser scattering. In the following the term "$x_n$" defines the particle size x with n vol.-% of the particles having a diameter below x and (100−n) vol.-% having a diameter above x.

Method and definitions are in detail laid down in the European Norm ISO 13320, "Particle size analysis—Laser diffraction Methods", first edition 2009-10-01, corrected version 2009-12-01. A skilled person is familiar with these methods which are also described e.g. in H. Wiese (D. Distler, Ed.), Aqueous Polymer Dispersions (Wässrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429.

The preparation of benzoxazinone (I) used for the production of the composition of benzoxazinone (I) as described herein (composition A), can be effected by the process described in WO 2010/145992, to which full reference is hereby made.

Particles of benzoxazinone (I) can be manufactured by various techniques, the necessary unit operations are generally known to a chemical engineer.

For example the benzoxazinone (I) can result from the synthesis with the right particle size, e.g. by a precipitation from appropriate solvents under appropriate technical conditions, like e.g. mixing speed, turbulence, temperature or solvent gradients, just to mention a few. Particles too small can be enlarged by e.g. agglomeration or Ostwald ripening, particles too large can be milled down mechanically. Usually, it is most economical to start with larger particles and mill subsequently.

For this step both dry and wet milling operations are suitable, for examples see e.g. H. Mollet and A. Grubenmann, Formulierungstechnik Emulsionen, Suspensionen, Feste Formen, Wiley VCH, Weinheim2000, chapter 5.3.1"Der Zerkleinerungsvorgang".

Dry milling can be performed with jet mills or mechanical mills (hammer mills, crushing or grinding gears, cryogenic grinding), wet milling can be achieved with e.g. colloid mills, rotor stator mills, double-cone mills, ball or bead mills, attritors, agitator ball mills, rotating mills, disk mills, annular chamber mills, and media mills, such as sand mills.) To dissipate the heat energy introduced during the grinding process, the grinding chambers are preferably fitted with cooling systems. Particularly suitable is the ball mill Drais Superflow DCP SF 12 from DRAISWERKE, INC.40 Whitney Road. Mahwah, N.J. 07430 USA, a Drais Perl Mill PMC from DRAISWERKE, INC., the circulating mill system ZETA from Netzsch-Feinmahltechnik GmbH, the disk mill from Netzsch Feinmahltechnik GmbH, Selb, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland.

In all cases the milling parameters—like e.g. equipment, energy input, velocity, size, material and filling of balls and beads—have to be adjusted to result in the particle size and particle size distribution according to this invention.

Finally all unit operations above can be coupled with sieves, gaps, cyclones or alike that allow a classification and thus a further refinement of the particle size distribution by separation and usually also recirculation of unwanted particles.

In above processes usually also milling aids, like e.g. dispersing agents, anti-baking agents but also defoamers and thickeners can be used to aid the operation.

The preferred embodiments of the invention mentioned herein below have to be understood as being preferred either independently from each other or in combination with one another.

Preferably at most 35% per volume of the particles have a diameter below 3 µm, which equals $x_{35}>=3$ µm;

particularly preferred at most 25% per volume of the particles have a diameter below 3 µm, which equals $x_{25}>=3$ µm;

especially preferred at most 20% per volume of the particles have a diameter below 3 µm, which equals $x_{20}>=3$ µm.

According to a further embodiment of the invention, preferably at most 60% per volume of the particles have a diameter below 5 µm, which equals $x_{60}>=5$ µm;

particularly preferred at most 45% per volume of the particles have a diameter below 5 µm, which equals $x_{45}>=5$ µm;

especially preferred at most 35% per volume of the particles have a diameter below 5 µm, which equals $x_{35}>=5$ µm;

more preferred at most 30% per volume of the particles have a diameter below 5 µm, which equals $x_{30}>=5$ µm.

According to a further embodiment of the invention, preferably at most 15% per volume of the particles have a diameter above 45 µm, which equals $x_{85}<=45$ µm.

The composition of benzoxazinone (I) according to the invention (composition A) comprises the benzoxazinone (I) in form of particles.

Preferably the particles of benzoxazinone (I) are in a crystalline form, more preferably in form of the crystalline, stable modifications A, B and/or C of the benzoxazinone (I).

Crystalline benzoxazinone (I) can be generally prepared by applying suitable crystallization conditions as described below. In order to yield crystalline benzoxazinone (I) according to the particle size distribution claimed in this invention fine-tuning of the process is necessary.

The concentration of benzoxazinone (I) in the solution or slurry used for the crystallization naturally depends on the nature of the solvent and the dissolution temperature and often lies in the range from 100 to 800 g/l. Suitable conditions can be determined by the person skilled in the art by routine experiments.

Preferably the solution or slurry used for the crystallization contains benzoxazinone (I) in a purity of at least 85%, often at least 90%, in particular at least 95%, i.e. the content of organic impurities which are not organic solvents is not more than 15 wt. %, often not more than 10 wt. %, and in particular not more than 5 wt. %, based on the benzoxazinone (I) present dissolved in the solvent.

The solution or slurry used for the crystallization is preferably essentially free from solvents other than those stated. In this context, "essentially free" means that the concentration of other solvents in the benzoxazinone (I) containing solution or slurry does not exceed 10 wt. %, often 5 wt. %, based on the total quantity of solvent.

The solution of benzoxazinone (I) can for example be prepared by the following methods (1) Dissolution of the benzoxazinone (I), in one of the aforesaid polar organic solvents, or
(2) Preparation of the benzoxazinone (I) by a chemical reaction and transfer of the reaction mixture, if necessary after removal of reagents and/or side products, into an organic solvent suitable according to the invention.

For the preparation of the solution by dissolution of the benzoxazinone (I), essentially any known form of benzoxazinone (I) can be used. Often amorphous benzoxazinone (I) or a mixture of different crystalline modifications or a mixture of amorphous and crystalline benzoxazinone (I) will be used. Also suitable are other crystalline forms of benzoxazinone (I) and mixtures thereof, for example the form B described below and the form C also described below, and mixtures of these forms as well as mixtures of form A with form B or form C of benzoxazinone (I).

The dissolution of the benzoxazinone (I) is usually effected at temperatures in the range from 10 to 200° C., preferably in the range from 10 to 100° C., in particular from 20 to 60° C.;

also preferably in the range from 85 to 200° C., in particular from 90 to 150° C.

The solution of the benzoxazinone (I) can also be prepared by transferring a reaction mixture obtained by a chemical reaction, which contains the benzoxazinone (I), if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present, for example water and/or methanol, are removed. The preparation of a solution of the benzoxazinone (I) by chemical reaction of a suitable precursor of benzoxazinone (I) can be effected by analogy to the methods which are described in the state of the art cited at the beginning, to which full reference is hereby made.

For the preparation of a slurry of the benzoxazinone (I), essentially any known form of benzoxazinone (I) can be used. Of course, in the preparation of a specific crystalline form of benzoxazinone (I), usually a form of benzoxazinone (I), which is different from the pure specific crystalline form, is used. However, benzoxazinone (I) may be used in a form already containing the specific crystalline form, thereby achieving a specific crystalline form having a higher content of the specific crystalline form.

For example, in the preparation of form A, usually a form of benzoxazinone (I), which is different from pure form A, is used. However, benzoxazinone (I) may be used in a form already containing form A, thereby achieving a form A having a higher content of form A.

Often amorphous benzoxazinone (I) or a mixture of different crystalline modifications or a mixture of amorphous and crystalline benzoxazinone (I) will be used. Also suitable are other crystalline forms of benzoxazinone (I) and mixtures thereof, for example the forms A, B and C described below, as well as mixtures of form A with form B and/or form C of benzoxazinone (I).

The crystallization of the benzoxazinone (I) is as a rule carried out until at least 80 wt. %, preferably at least 90 wt. %, of the benzoxazinone (I) used crystallizes out.

If the crystallization of the benzoxazinone (I) is effected by cooling, the cooling rate is preferably less than 10 K/min.

The crystallization of the benzoxazinone (I) can be promoted or accelerated by seeding with seed crystals of the benzoxazinone (I), preferably of form A, for example by adding seed crystals of the benzoxazinone (I), preferably of form A, before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved benzoxazinone (I).

If the crystallization is performed in the presence of seed crystals of the benzoxazinone (I), preferably of form A, these are preferably only added at a temperature at which the saturation concentration of the benzoxazinone (I) in the solvent in question has been reached, i.e. at or below that temperature at which the dissolved quantity of benzoxazinone (I) forms a saturated solution in the solvent in question. The person skilled in the art can determine the temperature dependence of the saturation concentration in a solvent in routine experiments.

The isolation of the crystallization product, i.e. the separation of the crystalline benzoxazinone (I), preferably form A, from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be affected in one or more steps, washing with water often being used in the last washing step. The washing is typically affected at temperatures below 30° C., often below 25° C. and in particular below 20° C., in order to keep the loss of valuable product as small as possible. Next, the form A obtained can be dried and then supplied for further processing. Often, however, the moist active substance obtained after washing, in particular an active substance moist with water, will be supplied directly for the further processing.

By means of the crystallization, the crystalline benzoxazinone (I), preferably form A, is obtained with a benzoxazinone (I) content of as a rule at least 90 wt. %, often 94 wt. %, in particular at least 96 wt. %.

The content of crystalline benzoxazinone (I), preferably form A, based on the total quantity of benzoxazinone (I), is typically at least 90% and often at least 95% or at least 96%.

Therefore, a particular embodiment of the invention relates to a composition of benzoxazinone (I) comprising the benzoxazinone (I) in form of particles, wherein the particles consist of at least 90 wt. % and often at least 95% or at least 96% of a crystalline benzoxazinone (I), preferably the crystalline form A.

The particles of benzoxazinone (I), preferably particles of benzoxazinone (I) containing the benzoxazinone (I) in a crystalline form, more preferably the crystalline form A, may be mixed with other forms of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, e.g. form B and/or form C, without loosing the benefits achieved by the particles of benzoxazinone (I).

Therefore, the invention also relates to a to a composition of benzoxazinone (I) comprising the benzoxazinone (I) in form of particles (composition A), wherein the particles are a mixture of the particles of benzoxazinone (I) containing the crystalline form A of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione as described herein and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione in a form which is different from form A, where the total amount of 1,5-dimethyl-6-thioxo-3-(2,2,7-trifluoro-3-oxo-4-(prop-2-ynyl)3,4-dihydro-2H-benzo[b][1,4]oxazin-6-yl)-1,3,5-triazinane-2,4-dione in the mixture is at least 90% by weight, preferably at least 94% by weight, based on the total weight of the mixture. The mixture can likewise be used for preparing formulations as described hereinafter and can likewise be used as the particles of benzoxazinone (I) containing the benzoxazinone (I) in a crystalline form, itself. In the mixture, the amount of crystalline benzoxazinone (I), preferably form A, will generally be at least 50% by weight, in particular at least 60% by weight, e.g. from 50 to 95% by weight, in particular from 60 to 90% by weight, based on the total amount of the particles of benzoxazinone (I) contained in the mixture.

In connection with the study on the crystallization of benzoxazinone (I), three crystalline modifications A, B and C were found. While modifications A and B can be obtained in pure form, modification C was occasionally obtained as a mixture with forms A and B.

The form A of the benzoxazinone (I) can be identified by X-ray powder diffractometry on the basis of its diffraction diagram. Thus an X-ray powder diffraction diagram of form A recorded using Cu-Kα radiation (1.54178 Å) at 25° C.

shows at least 3, often at least 5, in particular at least 7, and especially all of the reflections quoted in the following table as 2θ values or as interplanar spacings d

| 2θ values | d [Å] |
|---|---|
| 8.6 ± 0.2° | 10.28 |
| 10.9 ± 0.2° | 8.16 |
| 12.9 ± 0.2° | 6.86 |
| 13.4 ± 0.2° | 6.63 |
| 14.0 ± 0.2° | 6.33 |
| 14.4 ± 0.2° | 6.14 |
| 15.5 ± 0.2° | 5.72 |
| 16.9 ± 0.2° | 5.25 |
| 18.2 ± 0.2° | 4.88 |
| 20.5 ± 0.2° | 4.33 |

Studies on single crystals of form A demonstrate that the underlying crystal structure is orthorhombic. The unit cell has the space group Pna2(1). The characteristic data of the crystal structure of form A (determined at −173° C.) are compiled in the following table.

Crystallographic Characteristics of Form A

| Parameter | Form A |
|---|---|
| Crystal system | Orthorhombic |
| Space group | P n a 2$_1$ |
| a | 16.0815(4) Å |
| b | 13.1360(3) Å |
| c | 7.9675(2) Å |
| α | 90° |
| β | 90° |
| γ | 90° |
| Volume | 1683.11(7) Å$^3$ |
| Z | 4 |
| Density (calculated) | 1.63 g/cm$^3$ |
| R-Factor (%) | 2.97 | a, b, c = Length of the edges of the unit cell
α, β, γ = Angles of the unit cell
Z = Number of molecules, in the unit cell Form A displays a thermogram with a characteristic melting peak in the range from 150 to 185° C. The melting point, determined as the onset of the melting peak, typically lies in the range from about 170° C. to 180° C., in particular in the range from 174 to 179° C. The melting enthalpy is preferably in the range from 70 to 80 J/g. The values quoted here relate to values determined by differential calorimetry (differential scanning calorimetry DSC, aluminum closed and vented cup, nitrogen flow 150 ml/min, heating rate 5 K/min).

The production of the form A of benzoxazinone (I) may be effected by crystallization from a solution of benzoxazinone (I) in a suitable organic solvent. Suitable solvents for the crystallization of form A from a solution are organic solvents which are selected from $C_1$-$C_3$-alkanols, such as methanol, ethanol, n-propanol or isopropanol, $C_1$-$C_4$-dialkylketones, such as acetone, mono- or di-$C_1$-$C_4$-dialkylbenzenes such as ethylbenzene or xylenes, and mono- or dichlorobenzenes.

The production of the form A of benzoxazinone (I) may be also be effected by crystallization from a slurry of benzoxazinone (I) in a suitable organic solvent. Suitable solvents for the crystallization of form A from a slurry are mixtures of water with water-miscible organic solvents which are selected from $C_1$-$C_3$-alkanols, in particular ethanol or isopropanol, $C_2$-$C_4$-alkandiols, such as 1,3-propanediol, $C_1$-$C_4$-dialkylketones, such as acetone and cyclic ethers having preferably 4 to 6 carbon atoms and 1 or 2 oxygen atoms, such as tetrahydrofurane and 1,4-dioxane.

In order to obtain form A of benzoxazinone (I), the crystallization is affected at temperatures of below 60° C., in particular at most 50° C. and more preferably at most 40° C. Crystallization of form A is preferably effected under controlled conditions, i.e. the conditions of the crystallization are chosen to achieve a slow crystallization rate.

For this, in a first step i) a solution or slurry of benzoxazinone (I) in one of the aforesaid solvents or solvent mixtures is prepared, and then in a second step ii) crystallization of the benzoxazinone (I) is effected at temperatures of below 60° C., in particular at most 50° C. and more preferably at most 40° C., e.g. from −10 to 50° C., in particular from 0 to 40° C.

In order to obtain form A of benzoxazinone (I), the dissolution of the benzoxazinone (I) is usually effected at temperatures in the range from 10 to 100° C., in particular from 20 to 60° C.

The crystallization of form A of benzoxazinone (I) can be effected as follows, for example
  by cooling of the solution or slurry which contains the dissolved or dispersed benzoxazinone (I),
  by concentration of the solution or slurry which contains the dissolved or dispersed benzoxazinone (I), or
  by a combination of the aforesaid measures.

The form B can be identified by X-ray powder diffractometry on the basis of its diffraction diagram. Thus an X-ray powder diffraction diagram of form B recorded using Cu-Kα radiation (1.54178 Å) at 25° C. shows at least 3, often at least 5, in particular at least 7, and especially all of the reflections quoted in the following table as 2θ values or as interplanar spacings d

| 2θ values | d [Å] |
|---|---|
| 9.0 ± 0.2° | 9.85 |
| 10.9 ± 0.2° | 8.10 |
| 11.5 ± 0.2° | 7.69 |
| 12.9 ± 0.2° | 6.87 |
| 13.5 ± 0.2° | 6.56 |
| 14.9 ± 0.2° | 5.96 |
| 16.4 ± 0.2° | 5.42 |
| 16.5 ± 0.2° | 5.36 |
| 17.5 ± 0.2° | 5.06 |
| 20.3 ± 0.2° | 4.39 |

Form B displays a thermogram with a characteristic melting peak in the range from 190 to 220° C. The melting point, determined as the onset of the melting peak, typically lies in the range from about 200° C. to 210° C., in particular in the range from 203 to 208° C.

The melting enthalpy is preferably in the range from 30 to 40 J/g. The values quoted here relate to values determined by differential calorimetry (differential scanning calorimetry DSC, aluminum closed and vented cup, nitrogen flow 150 ml/min, heating rate 5 K/min).

The production of the modification B can be principally effected by running the crystallization at temperatures exceeding 60° C., in particular at temperatures of at least 80° C. or at least 90° C., e.g. from 80 to 130° C. or from 90 to 120° C.

Form B can be obtained e.g. by crystallization from a solution or slurry of benzoxazinone I in an organic solvent selected from toluene, monochlorobenzene or dichlorobenzene at temperatures of at least 80° C. or at least 90° C., e.g. from 80 to 130° C. or from 90 to 120° C.

Form B can be obtained e.g. by crystallization from a slurry of benzoxazinone (I) in a mixture of water and a water-miscible solvent, selected from $C_1$-$C_3$-alkanols, in particular methanol or isopropanol, $C_2$-$C_4$-alkandiols, such as 1,3-propanediol, $C_1$-$C_4$-dialkylketones, such as acetone and cyclic ethers having preferably 4 to 6 carbon atoms and 1 or 2 oxygen atoms such as tetrahydrofurane and 1,4-dioxane at temperatures of at least 80° C. or at least 90° C., e.g. from 80 to 130° C. or from 90 to 120° C. Apart from that crystallization from a slurry of benzoxazinone (I) to obtain form B can be performed by analogy to the crystallization of form A, in particular regarding preparation of the slurry, concentrations and measures of effecting crystallization, provided that crystallization is effected in the above temperature range.

Form B can be also be obtained e.g. by crystallization from a solution or slurry of benzoxazinone (I) in toluene at temperatures of at least 80° C. or at least 90° C., e.g. from 80 to 130° C. or from 90 to 120° C. Apart from that crystallization from a solution of benzoxazinone (I) to obtain form B can be performed by analogy to the crystallization of form A, in particular regarding preparation of the solution, concentrations and measures of effecting crystallization, provided that crystallization is effected in the above temperature range.

Pure form B is also obtained by heating the crystalline benzoxazinone (I), e.g. form A of benzoxazinone (I) or mixtures of forms A+B+C to temperatures of at least 160° C., in particular at least 170° C., e.g. temperatures in the range from 160° C. to 210° C. or in the range from 170 to 200° C.

In order to obtain form B of benzoxazinone (I), the crystallization is effected at temperatures of at least 80° C. or at least 90° C., e.g. from 80 to 130° C. or from 90 to 120° C. Crystallization of form B is preferably effected under controlled conditions, i.e. the conditions of the crystallization are chosen to achieve a slow crystallization rate.

For this, in a first step i) a solution or slurry of benzoxazinone I in one of the aforesaid solvents or solvent mixtures is prepared, and then in a second step ii) crystallization of the benzoxazinone I is effected at temperatures of at least 80° C. or at least 90° C., e.g. from 80 to 130° C. or from 90 to 120° C.

In order to obtain form B of benzoxazinone (I), the dissolution of the benzoxazinone (I) is usually effected at temperatures in the range from 85 to 200° C., in particular from 90 to 150° C.

The crystallization of form B of benzoxazinone I can be effected as follows, for example
  by cooling of a hot saturated solution or slurry which contains the dissolved or suspended benzoxazinone I, to a temperature in the range from 80 to 100° C.
  by concentration of a hot saturated solution or slurry which contains the dissolved or dispersed benzoxazinone I, or
  by a combination of the aforesaid measures.

By means of the crystallization the form B can be obtained with a benzoxazinone (I) content of as a rule at least 90 wt. %, often 94 wt. %, in particular at least 96 wt. %. The content of form B, based on the total quantity of benzoxazinone (I), is typically at least 90% and often at least 95% or at least 96%.

In the mixture of forms A, B and C, form C can be identified by X-ray powder diffractometry on the basis of its diffraction diagram. Thus an X-ray powder diffraction diagram recorded using Cu-Kα radiation (1.54178 Å) at 25° C. shows at least 3, often at least 5, and especially all of the reflections quoted in the following table as 2θ values or as interplanar spacings d

| 2θ values | d [Å] |
|---|---|
| 7.6 ± 0.2° | 11.64 |
| 9.6 ± 0.2° | 9.17 |
| 11.8 ± 0.2° | 7.48 |
| 12.4 ± 0.2° | 7.11 |
| 15.2 ± 0.2° | 5.81 |
| 15.9 ± 0.2° | 5.57 |
| 16.1 ± 0.2° | 5.52 |
| 19.1 ± 0.2° | 4.64 |

Just like the known amorphous benzoxazinone (I), the composition of benzoxazinone (I) comprising the benzoxazinone (I) in form of particles, preferably in form A of benzoxazinone (I) as well as mixtures of form A with other form of benzoxazinone (I) are suitable as a herbicide.

The invention thus also relates to plant protection agents containing the composition of benzoxazinone (I) comprising the benzoxazinone (I) in form of particles (composition A), preferably in the crystalline form A, and additives usual for the formulation of plant protection agents, in particular plant protection agents in the form of aqueous suspension concentrates (so-called SCs), non-aqueous suspension concentrates (so-called ODs), wettable powders (so-called WPs), water-dispersible granules (so-called WG's), dustable powder (so-called DP), powder for dry seed treatment (so-called DS), flowable concentrate for seed treatment (so-called FS), granules (so-called GR), oil-miscible flowable concentrate (so-called OF), oil-dispersible powder (so-called OP), directly applicable suspension concentrate (so-called SD), suspoemulsion (so-called SE); water-dispersible powder for slurry seed treatment (so-called WS), water-dispersible tablet (so-called WT) and mixed formulations ZE and ZC.

Preferred are the formulation types SC, WG, SE as well as the mix formulations ZC and ZE.

Especially preferred are the formulation types SC, WG and SE.

The invention also relates to a process for combating undesired plant growth, which is characterized in that the composition of benzoxazinone (I) comprising the benzoxazinone (I) in form of particles, preferably in the form A of benzoxazinone (I), more preferably as a suitable active substance preparation, is used on plants, their habitat and/or on seeds.

The invention also relates to plant protection agents containing a mixture of the composition of benzoxazinone (I) comprising the benzoxazinone (I) in form of particles, preferably in the crystalline form A, with at least one other form of benzoxazinone (I) and additives usual for the formulation of plant protection agents, in particular plant protection agents in the form of any of the formulation types mentioned above.

The invention also relates to a process for combating undesired plant growth, which is characterized in that the mixture of the composition of benzoxazinone (I) comprising the benzoxazinone (I) in form of particles, preferably in form A, of benzoxazinone (I), with at least one other form of benzoxazinone (I), preferably as a suitable active substance preparation, is used on plants, their habitat and/or on seeds.

The statements made hereinafter with regard to the composition of benzoxazinone (I) comprising the benzoxazinone (I) in form of particles, preferably in form A of benzoxazinone (I), also apply to mixtures of the composition of benzoxazinone (I) comprising the benzoxazinone (I) in form of particles, preferably in form A, with other forms of benzoxazinone (I).

Further, the statements made hereinafter with regard to the composition of benzoxazinone (I) comprising the benzoxazinone (I) in form of particles, preferably in form A of benzoxazinone (I), also apply to combinations of the composition of benzoxazinone (I) comprising as component A the benzoxazinone (I) in form of particles, preferably in form A, with at least one further herbicide B (component B) and/or safener C (component C) as defined.

In such combinations, the composition A can also comprise a mixtures of the composition of benzoxazinone (I) comprising the benzoxazinone (I) in form of particles, preferably in form A, with other forms of benzoxazinone (I).

In crop protection products, it is desirable in principle to increase the specificity and the reliability of the action of active compounds. In particular, it is desirable for the crop protection product to control the harmful plants effectively and, at the same time, to be tolerated by the useful plants in question. Selective herbicides control undesired vegetation while not harming the desired crop significantly.

The composition of benzoxazinone (I) comprising the benzoxazinone (I) in form of particles, preferably in form A of benzoxazinone (I), combinations comprising the composition A as defined (component A) and at least one further herbicide B (component B) and/or safener C (component C) as defined, and the plant protection agents which contain, composition A or or combinations thereof combat plant growth, in particular monocotyledonous weed species such as *Avena, Lolium, Alopecurus, Phalaris, Echinochloa, Digitaria, Setaria, Cyperus* species, *Agropyron, Cynodon, Imparato* and *Sorghum*, and dicotyledonous weed species such as *Galium, Viola, Veronica, Lamium, Stellaria, Amaranthus, Sinapsis, Ipomoea, Matricaria, Abutilon, Sida, Convolvulus, Cirsium, Rumex* and *Artemisia* on non-cultivated areas very well, particularly at high application levels. In crops such as wheat, barley, rye, rice, maize, sugar beet, soya and cotton, they are active against weeds and noxious grasses, without harming the crop plants significantly. This effect occurs above all at low application levels.

Depending on the particular application method, the composition of benzoxazinone (I) comprising the benzoxazinone (I) in form of particles, preferably in form A of benzoxazinone (I), combinations comprising the composition A as defined (component A) and at least one further herbicide B (component B) and/or safener C (component C) as defined or the plant protection agents containing composition A or or combinations thereof can also be used in a further number of crop plants for the elimination of undesired plants.

Examples for crops are crops of corn, soybeans, cereals, pulse, cotton, peanuts, sunflower, citrus, nuts, rice abd sugar cane;

preferred crops are corn, soybeans and cereals;
particularly preferred crops are corn and cereals,
especially preferred is corn.

Possible crops for example include the following
*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragara vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus armeniaca, Prunus avium, Prunus cerasus, Prunus dulcis, Prunus domestica, Prunus persica, Pyrus communis, Ribes sylvestre, Ricinus communis, Saccharum officinarum, Secale cereale, Sinapis alba, Solanum tuberosum, Sorghum bicolor (S. vulgare), Theobroma cacao, Trifolium pratense, Triticale, Triticum aestivum, Triticum durum, Vicia faba, Vitis vinifera* and *Zea mays*. Preferred crops are the following *Avena sativa, Glycine max, Gossypium hirsutum, (Gossypium arboreum, Gossypium herbaceum, Gossypium vitifolium), Helianthus annuus, Hordeum vulgare, Lens culinaris, Linum usitatissimum, Oryza sativa, Phaseolus lunatus, Phaseolus vulgaris, Pisum sativum Saccharum officinarum, Secale cereale, Sorghum bicolor (S. vulgare), Triticale, Triticum aestivum, Triticum durum, Vicia faba,* and *Zea mays*.

In addition, the composition of benzoxazinone (I) comprising the benzoxazinone (I) in form of particles, preferably in form A of benzoxazinone (I), or the plant protection agents containing the composition of benzoxazinone (I) comprising the benzoxazinone (I) in form of particles, preferably in form A, or combinations comprising the composition A as defined (component A) and at least one further herbicide B (component B) and/or safener C (component C) as defined can also be used in crops which through breeding including genetic engineering methods are tolerant towards the action of herbicides.

The composition A according to the invention and combinations comprising it can also be used in genetically modified plants. The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e. g. by glycosylation or polymer additions such as prenylated, acetylated or farnesylated moieties or PEG moieties. Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glypho-sate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoAreductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be under-stood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are dis-closed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these pro-teins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal pro-teins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton culti-vars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn culti-vars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars produ-cing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to in-crease the resistance or tolerance of those plants to bacterial, viral or fungal pathogens. Examples of such proteins are the so-called "pathogenesis-related proteins" (PR proteins, see, e.g. EP-A 392 225), plant disease resistance genes (e. g. potato culti-vars, which express resistance genes acting against *Phytophthora* infestans derived from the Mexican wild potato *Solanum bulbocastanum*) or T4-lyso-zym (e.g. potato cultivars capable of synthesizing these proteins with increased resistance against bacteria such as *Erwinia* amylvora). The methods for producing such genetically modi-fied plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Further, the composition of benzoxazinone (I) comprising the benzoxazinone (I) in form of particles, preferably in form A of benzoxazinone (I), or the plant protection agents containing the composition of benzoxazinone (I) comprising the benzoxazinone (I) in form of particles, preferably in form A, can also be used in crops which through breeding including genetic engineering methods are tolerant towards insect or fungal attack.

The composition of benzoxazinone (I) comprising the benzoxazinone (I) in form of particles, preferably in form A of benzoxazinone (I), or combinations comprising the composition A as defined (component A) and at least one further herbicide B (component B) and/or safener C (component C) as defined, are also just as suitable as the known amorphous benzoxazinone or combinations comprising it for the defoliation and desiccation of plant parts, for example for crop plants such as cotton, potato, rape, sunflower, soya bean or field beans, in particular cotton. In this regard, embodiments of the invention also relate to agents for the desiccation and/or defoliation of plants, processes for the production of these agents and methods for the desiccation and/or defoliation of plants using the composition of benzoxazinone (I)

comprising the benzoxazinone (I) in form of particles, preferably in the form A of benzoxazinone (I).

The composition of benzoxazinone (I) comprising the benzoxazinone (I) in form of particles, preferably in form A of benzoxazinone (I), are in particular suitable as desiccants for the desiccation of the aboveground parts of crop plants such as potato, rape, sunflower and soya bean, but also cereals. This enables completely mechanical harvesting of these important crop plants.

Also of scientific interest is the facilitation of harvesting which is enabled by the time-concentrated dropping or reduction of the strength of attachment to the tree with citrus fruits, olives or other species and varieties of pomaceous, stone and shelled fruit. The same mechanism, i.e. the promotion of the formation of separation tissue between fruit or leaf and shoot of the plants is also significant for well-controlled defoliation of useful plants, in particular cotton.

In addition, the shortening of the time interval in which the individual cotton plants become ripe leads to heightened fiber quality after the harvest.

The composition of benzoxazinone (I) comprising the benzoxazinone (I) in form of particles, preferably in form A of benzoxazinone (I), combinations comprising the composition A as defined (component A) and at least one further herbicide B (component B) and/or safener C (component C) as defined, or the plant protection agents containing either composition A or combinations thereof can for example be used in the form of directly sprayable aqueous solutions, powders, suspensions and also high concentration aqueous, oily or other suspensions, oil suspensions, pastes, dusting agents, scattering agents or granules by spraying, misting, dusting, scattering or pouring. The use forms are determined by the use purposes; in each case, they should ensure the finest possible distribution of the active substances according to the invention.

The plant protection agents according to the invention contain the composition of benzoxazinone (I) comprising the benzoxazinone (I) in form of particles, preferably in form A of benzoxazinone (I), in a purity, based on the modification in question, of at least 90 wt. %, and additives and/or carriers such as are usual for the formulation of plant protection agents. In such plant protection agents, the quantity of active substance, i.e. the total quantity of benzoxazinone (I) and of other active substances if necessary, normally lies in the range from 1 to 98 wt. %, in particular in the range from 10 to 95 wt. %, based on the total weight of the plant protection agent.

All solid and liquid substances which are normally used as carriers in plant protection agents, in particular in herbicide formulations are possible as carriers.

Solid carriers are for example mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder, ground plant parts like straw, flax, sugarcane straw or alike, and other solid carriers.

Liquid carriers, as well as water, are also organic liquids, for example mineral oil fractions of medium to high boiling point such as kerosene and diesel oil, also coal tar oils and oils of plant or animal origin, aliphatic, cyclic and aromatic hydrocarbons, for example paraffins, tetrahydronaphthalene, alkylated naphthalenes and derivatives thereof, alkylated benzenes and derivatives thereof, including aromatic and non-aromatic hydrocarbon mixtures, for example the products marketed under the trade names Exxsol and Solvesso, natural oils like plant—e.g. sunflower, corn, cotton, rapeseed, palm, soybean, coconut, olive, linseed—or animal oils—e.g. fish, pork, beef—or derivative of those like methyl oleate or biodiesel, alcohols such as propanol, butanol and cyclohexanol, ketones such as cyclohexanone, and strongly polar solvents, for example amides such as fatty alkyl dimethyl amides or N-methyl-pyrrolidone.

Typical additives include surface-active substances, in particular those wetting agents, emulsifiers and dispersant (additives) normally used in plant protection agents, and also viscosity-modifying additives (thickeners and rheology modifiers), antifoaming agents, antifreeze agents, pH adjusting agents, stabilizers, anticaking agents and biocides (preservatives).

Possible surface-active substances are preferably anionic and nonionic surfactants. Protective colloids are also suitable surface-active substances.

The quantity of surface-active substances will as a rule be 0.1 to 50 wt. %, in particular 0.5 to 30 wt. %, based on the total weight of the plant protection agents according to the invention, or 0.5 to 100 wt. %, based on the total quantity of solid active substances in the formulation. Preferably, the surface-active substance include at least one anionic surface-active substance and at least one nonionic surface-active substance, and the proportion of anionic to nonionic surface-active substance typically lies in the range from 101 to 110.

Examples of anionic surfactants include alkyl aryl-sulfonates, aromatic sulfonates, for example ligninsulfonates (Borresperse types, Borregaard), phenylsulfonates, naphthalenesulfonates (Morwet types, Akzo Nobel), dibutylnaphthalenesulfonates (Nekal types, BASF), alkyl sulfates, in particular fatty alcohol sulfates, lauryl sulfates, and sulfated hexadeca-, heptadeca- and octadecanols, alkylsulfonates, alkyl ether sulfates, in particular fatty alcohol (poly)glycol ether sulfates, alkyl aryl ether sulfates, alkyl polyglycol ether phosphates, polyarylphenyl ether phosphates, alkylsulfosuccinates, olefin sulfonates, paraffin sulfon-ates, petroleum sulfonates, taurides, sarcosides, fatty acids, alkylnaphthalenesulfonic acids, naphthalene-sulfonic acids, ligninsulfonic acids, condensation products of sulfonated naphthalenes with formaldehyde, condensation products of sulfonated naphthalenes with formaldehyde and phenol and optionally urea and condensation products of phenolsulfonic acid with formaldehyde and urea, lignin sulfite waste liquor, alkyl phosphates, alkyl aryl phosphates, for example tristyryl phosphates, and polycarboxylates such as for example polyacrylates, maleic anhydride/olefin copolymers (for example Sokalan® CP9, BASF), including the alkali metal, alkaline earth, ammonium and amine salts of the aforesaid substances. Preferred anionic surface-active substances are those which bear at least one sulfonate group and in particular the alkali metal and ammonium salts thereof.

Examples of non-ionic surface-active substances are alkylphenol alkoxylates, in particular ethoxylates and ethoxylate-copropoxylates of octylphenol, isooctylphenol, nonylphenol and tributylphenol, di- and tristyrylphenol alkoxylates, alcohol alkoxylates, in particular fatty alcohol ethoxylates and fatty alcohol ethoxylate-copropoxylates, for example alkoxylated isotridecanol, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, ethoxylated fatty acid amides, ethoxylated fatty acid esters, alkyl polyglycosides, ethoxylated alkyl polyglycosides, sorbitan fatty acid esters, ethoxylated sorbitan fatty acid esters, glycerol fatty acid esters, lower molecular weight polyalkylene oxides such as polyethylene glycol, polypropylene oxide, polyethylene oxide copropylene oxide di- and tri-block copolymers, and mixtures thereof. Preferred nonionic surface-active substances are fatty alcohol ethoxylates, alkyl polyglycosides, glycerol fatty acid esters, castor oil ethoxylates, fatty acid ethoxylates, fatty acid amide ethoxylates, lanolin ethoxylates, fatty acid polyglycol esters, ethylene oxide propylene oxide block copolymers and mixtures thereof.

Protective colloids are typically water-soluble, amphiphilic polymers which unlike the aforesaid surfactants typically have molecular weights over 2,000 daltons (number average). Examples thereof are proteins and denatured proteins such as casein, polysaccharides such as water-soluble starch derivatives and cellulose derivatives, hydrophobically modified starches and celluloses, for example methylcellulose, and also polycarboxylates such as polyacrylic acid, acrylic acid copolymers and maleic acid copolymers (BASF Sokalan types), polyvinyl alcohol (Mowiol types from Clariant), polyalkoxylates, polyvinylpyrrolidone, vinylpyrrolidone copolymers, polyvinyl amines, polyethyleneimines (Lupasol types from BASF) and higher molecular weight polyalkylene oxides such as polyethylene glycol, polypropylene oxides, and polyethylene oxide copolypropylene oxide di- and tri-block copolymers.

The plant protection agents according to the invention can also contain one or more additives modifying the viscosity (rheology modifiers). These are understood in particular to mean substances and substance mixtures which impart modified flow behavior to the formulation, for example a high viscosity in the resting state and low viscosity in the moving state. The nature of the rheology modifier is determined by the nature of the formulation. As examples of rheology modifiers, inorganic substances, for example layer silicates and organically modified layer silicates such as bentonites or attapulgites (for example Attaclay®, Engelhardt Co.), and organic substances such as polysaccharides and heteropolysaccharides such as Xanthan Gum® (Kelzan® from Kelco Co.), Rhodopol® 23 (Rhone Poulenc) or Veegum® (R.T. Vanderbilt Co.) should be mentioned. The quantity of the viscosity-modifying additives is often 0.1 to 5 wt. %, based on the total weight of the plant protection agent.

Examples of antifoaming agents are the silicone emulsions known for this purpose (Silikon® SRE, Wacker Co. or Rhodorsil® from Rhodia Co.), long-chain alcohols, fatty acids and salts thereof, foam suppressants of the aqueous wax dispersion type, solid foam suppressants (so-called Compounds) and organofluorine compounds and mixtures thereof. The quantity of antifoaming agent is typically 0.1 to 1 wt. %, based on the total weight of the plant protection agent.

The plant protection agents according to the invention can also contain preservatives for stabilization. Suitable preservatives are those based on isothiazol-ones, for example Proxel® from ICI Co., or Acticide® from Thor Chemie Co. or Kathon® MK from Rohm & Hass Co. The quantity of preservative is typically 0.05 to 0.5 wt. %, based on the total weight of the SC.

Aqueous plant protection agents, i.e. those with an aqueous carrier, often contain antifreeze agents. Suitable antifreeze agents are liquid polyols, for example ethylene glycol, propylene glycol or glycerine, and urea. The quantity of antifreeze agent is as a rule 1 to 20 wt. %, in particular 5 to 10 wt. %, based on the total weight of the aqueous plant protection agent.

If the plant protection agents containing the composition of benzoxazinone (I) comprising the benzoxazinone (I) in form of particles, preferably in the crystalline modification A of benzoxazinone (I) and optionally at least one further herbicide B (component B) and/or safener C (component C) are used for seed treatment, they can also contain normal components such as are used for seed treatment, for example in dressing or coating. In addition to the aforesaid components, these include in particular colorants, adhesives, fillers and plasticizers.

All the dyes and pigments usual for such purposes are possible as colorants. Both pigments of low solubility in water and also dyes soluble in water are usable here. As examples, the dyes and pigments known under the names Rhodamin B, C.I. Pigment Red 112 and C.I. Solvent Red 1, Pigment Blue 154, Pigment Blue 153, Pigment Blue 152, Pigment Blue 151, Pigment Blue 80, Pigment Yellow 1, Pigment Yellow 13, Pigment Red 482, Pigment Red 481, Pigment Red 571, Pigment Red 531, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 10 and Basic Red 108 may be mentioned. The quantity of colorant will normally not constitute more than 20 wt. % of the formulation and preferably lies in the range from 0.1 to 15 wt. %, based on the total weight of the formulation.

All binders normally usable in dressings come under consideration as adhesives. Examples of suitable binders include thermoplastic polymers such as poly-vinylpyrrolidone, polyvinyl acetate, polyvinyl alcohol and tylose and also polyacrylates, polymethacrylates, polybutenes, polyisobutenes, polystyrene, polyethylene amines, polyethylene amides, the aforesaid protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropyl cellulose and starch derivatives and modified starches, dextrins, maltodextrins, alginates and chitosans, and also fats, oils, proteins, including casein, gelatin and zein, gum Arabic and shellac. The adhesives are preferably plantcompatible, i.e. they exhibit no, or no significant, phytotoxic effects. The adhesives are preferably biodegradable. The adhesive is preferably selected such that it acts as a matrix for the active components of the formulation. The quantity of adhesive will normally not constitute more than 40 wt. % of the formulation and preferably lies in the range from 1 to 40 wt. % and in particular in the range from 5 to 30 wt. %, based on the total weight of the formulation.

In addition to the adhesive, the formulation for seed treatment can also contain inert fillers. Examples of these are the aforesaid solid carriers, in particular finely divided inorganic materials such as clays, chalk, bentonite, kaolin, talc, perlite, mica, silica gel, diatomaceous earth, quartz powder and montmorillonite but also fine-particle organic materials such as wood flour, cereal flour, active charcoal and the like. The quantity of filler is preferably selected such that the total quantity of filler does not exceed 70 wt. %, based on the total weight of all non-volatile components of the formulation. Often, the quantity of filler lies in the range from 1 to 50 wt. %, based on the total weight of all non-volatile components of the formulation.

In addition, the formulation for seed treatment can also contain a plasticizer which increases the flexibility of the coating. Examples of plasticizers are oligomeric polyalkylene glycols, glycerine, dialkyl phthalates, alkylbenzyl phthalates, glycol benzoates and comparable compounds. The quantity of plasticizer in the coating often lies in the range from 0.1 to 20 wt. %, based on the total weight of all non-volatile components of the formulation.

A preferred embodiment of the invention relates to liquid formulations of the composition of benzoxazinone (I) comprising the benzoxazinone (I) in form of particles, preferably in the form A of benzoxazinone (I) and optionally at least one further herbicide B (component B) and/or safener C (component C). In addition to the solid active substance phase, these have at least one liquid phase, in which benzoxazinone (I) is present in the form of particles according to the invention, preferably in the form of form A. Possible liquid phases are essentially water and those organic solvents in which the particles of benzoxazinone (I), preferably the form A, is only slightly soluble, or insoluble, for example those wherein the solubility of the particles of benzoxazinone (I), preferably of the form A at 25° C. and 1013 mbar is not more than 1 wt. %, in particular not more than 0.1 wt. %, and especially not more than 0.01 wt. %.

According to one embodiment of the invention, the liquid phase, wherein the composition as claimed in claims 1 to 5 is present in form of particles, is water.

According to a first preferred embodiment, the liquid phase is selected from water and aqueous solvents, i.e. solvent mixtures which in addition to water also contain up to 20 wt. %, preferably however not more than 10 wt. %, based on the total quantity of water and solvent, of one or more organic solvents miscible with water, for example ethers miscible with water such as tetrahydrofuran, methyl glycol, methyl diglycol, alkanols such as isopropanol or polyols such as glycol, glycerine, diethylene glycol, propylene glycol and the like. Such formulations are also referred to below as suspension concentrates (SCs).

Such suspension concentrates contain benzoxazinone (I) in the form of the particles of benzoxazinone (I), preferably of the modification A, in a finely divided particulate form, wherein the particles of benzoxazinone (I), preferably the form A, are present suspended in an aqueous phase.

In such SCs the quantity of active substance, i.e. the total quantity of benzoxazinone (I) and of other active substances if necessary, usually lies in the range from 10 to 70 wt. %, in particular in the range from 20 to 50 wt. %, based on the total weight of the suspension concentrate.

In addition to the active substance, aqueous suspension concentrates typically contain surface-active substances, and also if necessary antifoaming agents, thickeners (=rheology modifiers), antifreeze agents, stabilizers (biocides), agents for adjusting the pH and anticaking agents.

Possible surface-active substances are the previously named surface-active substances. Preferably the aqueous plant protection agents according to the invention contain at least one of the previously named anionic surfactants and if necessary one or more nonionic surfactants, if necessary in combination with a protective colloid. The quantity of surface-active substances will as a rule be 1 to 50 wt. %, in particular 2 to 30 wt. %, based on the total weight of the aqueous SCs according to the invention. Preferably the surface-active substances include at least one anionic surface-active substance and at least one nonionic surface-active substance, and the proportion of anionic to nonionic surface-active substance typically lies in the range from 101 to 110.

Concerning the nature and quantity of the antifoaming agents, thickeners, antifreeze agents and biocides, the same applies as aforesaid.

If necessary, the aqueous SCs according to the invention can contain buffers for pH regulation. Examples of buffers are alkali metal salts of weak inorganic or organic acids, such as for example phosphoric acid, boric acid, acetic acid, propionic acid, citric acid, fumaric acid, tartaric acid, oxalic acid and succinic acid.

According to a second preferred embodiment, the liquid phase consists of non-aqueous organic solvents in which the solubility of the composition of benzoxazinone (I) comprising the benzoxazinone (I) in form of particles, preferably in the form A of benzoxazinone (I), at 25° C. and 1013 mbar is not more than 1 wt. %, in particular not more than 0.1 wt. %, and especially not more than 0.01 wt. %. These include in particular aliphatic and cycloaliphatic hydrocarbons and oils, in particular those of plant origin, and also $C_1$-$C_4$ alkyl esters of saturated or unsaturated fatty acids or fatty acid mixtures, in particular the methyl esters, for example methyl oleate, methyl stearate and rape oil methyl ester, but also paraffinic mineral oils and the like.

Accordingly, the present invention relates also to agents for plant protection in the form of a non-aqueous suspension concentrate, which will also be referred to below as OD (oil-dispersion). Such ODs contain the composition of benzoxazinone (I) as described herein comprise the benzoxazinone (I) in a finely divided particulate form, wherein the particles, preferably of the form A, are present suspended in a non-aqueous phase.

In such ODs, the quantity of active substance, i.e. the total quantity of benzoxazinone (I) and of other active substances if necessary, usually lies in the range from 10 to 70 wt. %, in particular in the range from 20 to 50 wt. %, based on the total weight of the non-aqueous suspension concentrate.

In addition to the active substance and the liquid carrier, non-aqueous suspension concentrates typically contain surface-active substances, and also if necessary antifoaming agents, agents to modify the rheology and stabilizers (biocides).

Possible surface-active substances are preferably the previously named anionic and nonionic surfactants. The quantity of surface-active substances will as a rule be 1 to 30 wt. %, in particular 2 to 20 wt. %, based on the total weight of the non-aqueous SCs according to the invention. Preferably the surface-active substances include at least one anionic surface-active substance and at least one nonionic surface-active substance, and the proportion of anionic to nonionic surface-active substance typically lies in the range from 101 to 110.

The composition of benzoxazinone (I) comprising the benzoxazinone (I) in form of particles, preferably in form A of benzoxazinone (I), according to the invention can also be formulated as solid plant protection agents. These include powder, scattering and dusting agents but also water-dispersible powders and granules, for example coated, impregnated and homogenous granules. Such formulations can be produced by mixing or simultaneous grinding of the particles of benzoxazinone (I), preferably of the form A of benzoxazinone (I) with a solid carrier and if necessary other additives, in particular surface-active substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder or other solid carriers. Solid formulations can also be produced by spray drying, if necessary in the presence of polymeric or inorganic drying aids, and if necessary in the presence of solid carriers. For the production of solid formulations of the particles of benzoxazinone (I), preferably of benzoxazinone (I) of form A, extrusion processes, fluidized bed granulation, spray granulation and comparable technologies are suitable.

Possible surface-active substances are the previously named surfactants and protective colloids. The quantity of surface-active substances will as a rule be 1 to 30 wt. %, in particular 2 to 20 wt. %, based on the total weight of the solid formulation according to the invention.

In such solid formulations, the quantity of active substance, i.e. the total quantity of benzoxazinone and of other active substances if necessary, usually lies in the range from 10 to 70 wt. %, in particular in the range from 20 to 50 wt. %, based on the total weight of the solid formulation.

The application of the composition of benzoxazinone (I) comprising the benzoxazinone (I) in form of particles, preferably in the form A of benzoxazinone (I), or the herbicidal agents containing them is effected, if the formulation is not already ready for use, in the form of aqueous spray fluids. These are prepared by dilution of the aforesaid formulations containing the composition of benzoxazinone (I) comprising the benzoxazinone (I) in form of particles, preferably in the form A of benzoxazinone (I), with water. The spray fluids can also contain other components in dissolved, emulsified or suspended form, for example fertilizers, active substances of other herbicidal or growth-regulating active substance groups, other active substances, for example active substances for combating animal pests or phyto-pathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention.

The application of the composition of benzoxazinone (I) comprising the benzoxazinone (I) in form of particles, preferably in the form A of benzoxazinone (I), or of the plant protection agents containing them can be effected in a pre-emergence or in a post-emergence method. Also application techniques can be used wherein the herbicidal agents are sprayed using the spraying equipment in such a manner that the leaves of the sensitive crop plants are as far as possible not hit, while the active substances reach the leaves of undesired plants growing under them or the uncovered soil surface (post-directed, lay-by).

The quantities of benzoxazinone (I) applied are 0.001 to 3.0 kg active substance per hectare, preferably 0.01 to 1.0 kg active substance (a·S)/ha, depending on the treatment aim, season, target plants and growth stage.

In a further embodiment, the application of the composition of benzoxazinone (I) comprising the benzoxazinone (I) in form of particles, preferably in the form A of benzoxazinone (I), or the plant protection agent containing them can be effected by treatment of seed.

Treatment of seed essentially includes all techniques with which the person skilled in the art is familiar (seed dressing, seed coating, seed dusting, seed soaking, seed film coating, seed multilayer coating, seed encrusting, seed dripping and seed pelleting) on the basis of the composition of benzoxazinone (I) comprising the benzoxazinone (I) in form of particles, preferably in form A of benzoxazinone (I), or agents prepared therefrom. Here the plant protection agents can be applied diluted or undiluted.

The term seed includes seed of all types, for example grains, seeds, fruits, tubers, cuttings and similar forms. Preferably, the term seed here describes grains and seeds.

As seed, seed of the crop plants mentioned above but also the seeds of transgenic plants or those obtained by conventional breeding methods can be used.

For the seed treatment, benzoxazinone (I) is normally used in quantities of 0.001 to 10 kg per 100 kg of seed.

To broaden the spectrum of action and to achieve synergistic effects, the composition of benzoxazinone (I) comprising the benzoxazinone (I) in form of particles, preferably in the form A of benzoxazinone (I), can be mixed and applied together with many members of other herbicidal or growth regulating active substance groups. In addition, it can be advantageous to formulate or apply the composition of benzoxazinone (I) comprising the benzoxazinone (I) in form of partilles, preferably in the form A of benzoxazinone (I) together with safeners. With regard to such combinations, full reference is made to WO 2010/145992.

Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

In addition, it can be of value to apply the composition of benzoxazinone (I) comprising the benzoxazinone (I) in form of particles, preferably in the form A, alone or in combination with other herbicides also mixed with still further plant protection agents, together for example with agents for combating pests or phytopathogenic fungi or bacteria. Also of interest is the miscibility with mineral salt solutions which are used for the elimination of nutritional and trace element deficiencies. Additives such as non-phytotoxic oils and oil concentrates can also be added.

In one embodiment of the present invention the herbicidal combinations according to the present invention comprise at least the composition A (component A) and at least one further active compound selected from herbicides B (component B), preferably herbicides B of class b1) to b15), and safeners C (component C).

In another embodiment of the present invention the the herbicidal combinations according to the present invention comprise at least the composition A and at least one further active compound B (herbicide B).

The further active compound B (herbicide B) is preferably selected from the herbicides of class b1) to b15)

b1) lipid biosynthesis inhibitors;

b2) acetolactate synthase inhibitors (ALS inhibitors);

b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of very long chain fatty acids (VLCFA inhibitors);
b11) cellulose biosynthesis inhibitors;
b12) decoupler herbicides;
b13) auxin herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

including their agriculturally acceptable salts or derivatives.

Preference is given to those herbicidal combinations according to the present invention comprising at least one herbicide B selected from herbicides of class b2, b3, b4, b5, b6, b9 and b10.

Specific preference is given to those herbicidal combinations according to the present invention which comprise at least one herbicide B selected from the herbicides of class b4, b6, b9 and b10.

Particular preference is given to those herbicidal combinations according to the present invention which comprise at least one herbicide B selected from the herbicides of class b4, b6 and b10.

According to a first embodiment of the invention the herbicidal combinations contain at least one inhibitor of the lipid biosynthesis (herbicide b1). These are compounds which inhibit lipid biosynthesis. Inhibition of the lipid biosynthesis can be affected either through inhibition of acetyl CoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to a second embodiment of the invention the herbicidal combinations contain at least one ALS inhibitor (herbicide b2). The herbicidal activity of these compounds is based on the inhibition of acetolactate synthase und thus on the inhibition of the branched chain aminoacid biosynthesis. These inhibitors belong to the group B of the HRAC classification system.

According to a third embodiment of the invention the herbicidal combinations contain at least one inhibitor of photosynthesis (herbicide b3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

According to a fourth embodiment of the invention the herbicidal combinations contain at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

According to a fifth embodiment of the invention the herbicidal combinations contain at least one bleacher-herbicide (herbicide b5). The herbicidal activity of these compounds is based on the inhibition of the carotinoid biosynthesis. These include compounds which inhibit carotinoid biosynthesis by inhibition of phytoene desaturase (so-called PDS inhibitors, group F1 of HRAC classification), compounds which inhibit the 4-hydroxyphenylpyruvat-dioxygenase (HPPD inhibitors, group F2 of HRAC classification) and compounds which inhibit carotinoid biosynthesis by an unknown mode of action (bleacher—unknown target, group F3 of HRAC classification).

According to a sixth embodiment of the invention the herbicidal combinations contain at least one EPSP synthase inhibitor (herbicide b6). The herbicidal activity of these compounds is based on the inhibition of enolpyruvyl shikimate 3-phosphate synthase und thus on the inhibition of the aminoacid biosynthesis in plants. These inhibitors belong to the group G of the HRAC classification system.

According to a seventh embodiment of the invention the herbicidal combinations contain at least one glutamin synthetase inhibitor (herbicide b7). The herbicidal activity of these compounds is based on the inhibition of glutamin synthetase und thus on the inhibition of the aminoacid biosynthesis in plants. These inhibitors belong to the group H of the HRAC classification system.

According to an eighth embodiment of the invention the herbicidal combinations contain at least one DHP synthase inhibitor (herbicide b8). The herbicidal activity of these compounds is based on the inhibition of 7,8-dihydropteroate synthetase. These inhibitors belong to the group I of the HRAC classification system.

According to a ninth embodiment of the invention the herbicidal combinations contain at least one mitose inhibitor (herbicide b9). The herbicidal activity of these compounds is based on the disturbance or inhibition of microtubule formation or organization and thus on the mitosis inhibition. These inhibitors belong to the groups K1 and K2 of the HRAC classification system. Among these, compounds of the group K1, in particular dinitroanilines, are preferred.

According to a tenth embodiment of the invention the herbicidal combinations contain at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

According to an eleventh embodiment of the invention the herbicidal combinations contain at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

According to a twelfth embodiment of the invention the herbicidal combinations contain at least one decoupler herbicide (herbicide b12). The herbicidal activity of these compounds is based on the disruption of the cell membrane. These inhibitors belong to the group M of the HRAC classification system.

According to a thirteenth embodiment of the invention the herbicidal combinations contain at least one auxin herbicide (herbicide b13). These include compounds which act like auxins, i.e. plant hormones, and inhibit the growth of the plants. These compounds belong to the group O of the HRAC classification system.

According to a fourteenth embodiment of the invention the herbicidal combinations contain at least one auxin transport inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http//www.plant-protection.org/hrac/MOA.html).

Examples of herbicides B which can be used in combination with the composition A according to the present invention are b1) from the group of the lipid biosynthesis inhibitors ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors

Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-yrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]-benzenemethanamine (CAS 420138-01-8) and sulfonylaminocarbonyl-triazolinone herbicides such as flucarbazone, flucarbazone-sodium, propoxycarbazon, propoxycarbazon-sodium, thiencarbazone and thiencarbazone-methyl. Among these, a preferred embodiment of the invention relates to those combinations comprising at least one imidazolinone herbicide;

b3) from the group of the photosynthesis inhibitors amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazin, simazin, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridatre, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those combinations comprising at least one aryl urea herbicide. Among these, likewise a preferred embodiment of the invention relates to those combinations comprising at least one triazine herbicide. Among these, likewise a preferred embodiment of the invention relates to those combinations comprising at least one nitrile herbicide;

b4) from the group of the protoporphyrinogen-IX oxidase inhibitors acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-b 1H-pyrazole-1-carboxamide CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-2-chloro-6-fluoro-4-trifluoromethylphenoxy)-5-methyl-1H-pyrazole-1-carboxamide (CAS 45100-b 03-7) and 3-[7-fluoro-3-oxo-4-(prop-2-ynyl)-3,4-dihydro-2H-benzo[1,4]oxazin-6-yl]-1,5-dimethyl-6-thioxo[1,3,5]triazinan-2,4-dione;

b5) from the group of the bleacher herbicides

PDS inhibitors beflubutamid, diflufenican, fluridone, flurochloridone, flurtamone, norflurazon, picolinafen, and 4-(3-trifluoromethylphenoxy)-2-(4-trifluoromethylphenyOpyrimidine (CAS 180608-33-7), HPPD inhibitors benzobicyclon, benzofenap, isoxaflutole, mesotrione, pyrasulfotole, pyrazolynate, pyrazoxyfen, sulcotrione, tefuryltrione, tembotrione, topramezone and bicyclopyrone, bleacher, unknown target aclonifen, amitrole, clomazone and flumeturon;

b6) from the group of the EPSP synthase inhibitors
glyphosate, glyphosate-isopropylammonium and glyphosate-trimesium (sulfosate);

b7) from the group of the glutamine synthase inhibitors
bilanaphos (bialaphos), bilanaphos-sodium, glufosinate, glufosinate-P and glufosinate-ammonium;

b8) from the group of the DHP synthase inhibitors
asulam;

b9) from the group of the mitose inhibitors
compounds of group K1 dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2 chlorpropham, propham and carbetamide, among these, compounds of group K1, in particular dinitroanilines are preferred;

b10) from the group of the VLCFA inhibitors
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napronilide and napropamide, tetrazolinones such fentrazamide, and other herbicides such as anilofos, cafenstrole, fenoxasulfone, ipfencarbazone, piperophos, pyroxasulfone and isoxazoline compounds of the formula II,

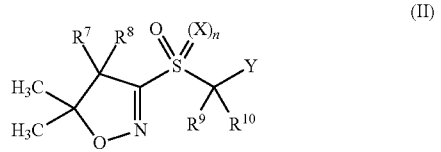

(II)

wherein $R^7$, $R^8$, $R^9$, $R^{10}$, W, Z and n have the following meanings $R^7$, $R^8$, $R^9$, $R^{10}$ independently of one another hydrogen, halogen or $C_1$-$C_4$-alkyl;

X oxygen or NH;

Y phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$-alkoxy, $C_1$-$C_4$-haloalkyl and $C_1$-$C_4$-haloalkoxy;

preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$; and n zero or one;

among the isoxazoline compounds of the formula II, preference is given to isoxazoline compounds of the formula II, wherein $R^7$, $R^8$, $R^9$, $R^{10}$ independently of one another are H, F, Cl or methyl;

X is oxygen;

n is 0 or 1; and

Y is phenyl, pyrazolyl or 1,2,3-triazolyl, wherein the three last-mentioned radicals are unsubstituted or carry one, two or three substituents $R^{yy}$, especially one of the following radicals

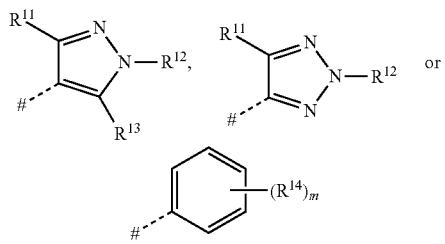

wherein
$R^{11}$ is halogen, $C_1$-$C_4$-alkyl or $C_1$-$C_4$-haloalkyl;
$R^{12}$ is $C_1$-$C_4$-alkyl;
$R^{13}$ is halogen, $C_1$-$C_4$-alkoxy or $C_1$-$C_4$-haloalkoxy;
$R^{14}$ is halogen, $C_1$-$C_4$-alkyl, $C_1$-$C_4$-haloalkyl or $C_1$-$C_4$-haloalkoxy;
m is 0, 1, 2 or 3; and
# denotes the point of attachment to the group $CR^{13}R^{14}$;

among the isoxazoline compounds of the formula II, particular preference is given to those isoxazoline compounds of the formula II, wherein $R^7$ is hydrogen;
$R^8$ is fluorine;
$R^9$ is hydrogen or fluorine;
$R^{10}$ is hydrogen or fluorine;
X is oxygen;
Y is one of the radicals of the formulae $Y^1$, $Y^2$, $Y^3$ or $Y^4$

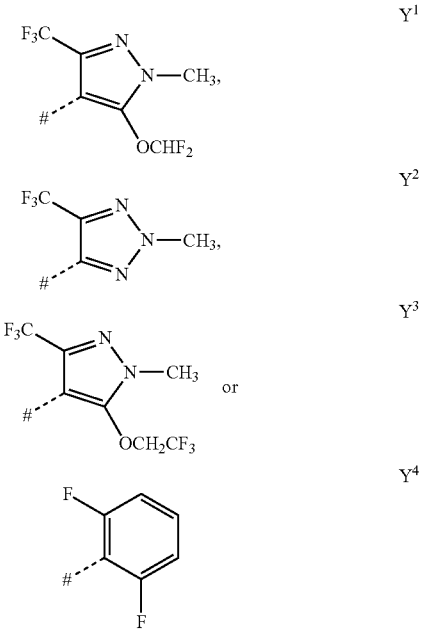

wherein # denotes the point of attachment to the group $CR^9R^{10}$;

n is zero or 1, in particular 1; and among these, especially preferred are the isoxazoline compounds of the formulae II.1, II.2, II.3, II.4, II.5, II.6, II.7, II.8 and II.9

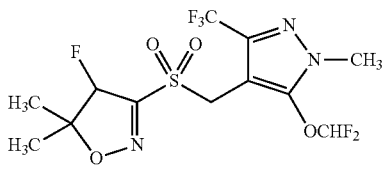
II.1

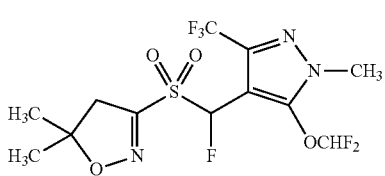
II.2

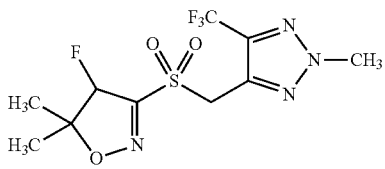
II.3

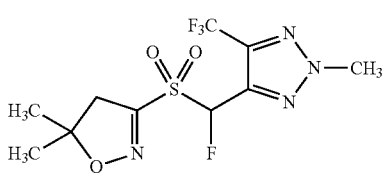
II.4

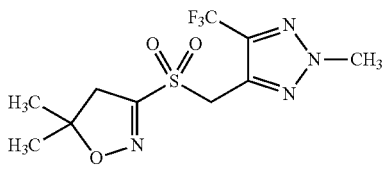
II.5

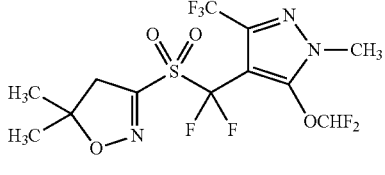
II.6

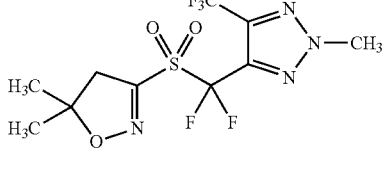
II.7

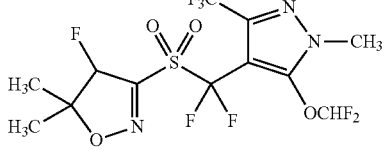
II.8

-continued

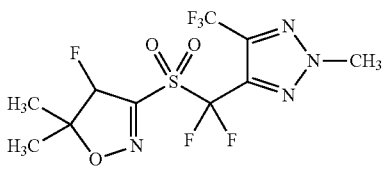
II.9 the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxyacetamides, especially to pyroxasulfone;

b11) from the group of the cellulose biosynthesis inhibitors chlorthiamid, dichlobenil, flupoxam, isoxaben, 1-Cyclohexyl-5-pentafluorphenyloxy-$1^4$-[1,2,4,6]thiatriazin-3-ylamine and piperazine compounds of formula III,

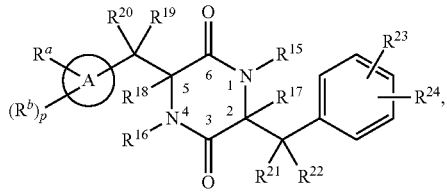
III in which

A is phenyl or pyridyl where $R^a$ is attached in the ortho-position to the point of attachment of A to a carbon atom;

$R^a$ is CN, $NO_2$, $C_1$-$C_4$-alkyl, D-$C_3$-$C_6$-cycloalkyl, $C_1$-$C_4$-haloalkyl, $C_1$-$C_4$-alkoxy, $C_1$-$C_4$-haloalkoxy, O-D-$C_3$-$C_6$-cycloalkyl, $S(O)_qR^y$, $C_2$-$C_6$-alkenyl, D-$C_3$-$C_6$-cycloalkenyl, $C_3$-$C_6$-alkenyloxy, $C_2$-$C_6$-alkynyl, $C_3$-$C_6$-alkynyloxy, $NR^AR^B$, tri-$C_1$-$C_4$-alkylsilyl, D-C(=O)—$R^{a1}$, D-P(=O)$(R^{a1})_2$, phenyl, naphthyl, a 3- to 7-membered monocyclic or 9-or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups $R^{aa}$ and/or $R^{a1}$, and, if $R^a$ is attached to a carbon atom, additionally halogen; $R^y$ is $C_1$-$C_6$-alkyl, $C_3$-$C_4$-alkenyl, $C_3$-$C_4$-alkynyl, $NR^AR^B$ or $C_1$-$C_4$-haloalkyl and q is 0, 1 or 2;

$R^A,R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A,R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond, $C_1$-$C_4$-alkylene, $C_2$-$C_6$-alkenyl or $C_2$-$C_6$-alkynyl;

$R^{a1}$ is hydrogen, OH, $C_1$-$C_8$-Alkyl, $C_1$-$C_4$-haloalkyl, $C_3$-$C_6$-cycloalkyl, $C_2$-$C_8$-alkenyl, $C_5$-$C_6$-cycloalkenyl, $C_2$-$C_8$-alkynyl, $C_1$-$C_6$-alkoxy, $C_1$-$_4$-haloalkoxy, $C_3$-$C_8$-alkenyloxy, $C_3$-$C_8$-alkynyloxy, $NR^AR^B$, $C_1$-$C_6$-alkoxyamino, $C_1$-$C_6$-alkylsulfonylamino, $C_1$-$C_6$-alkylaminosulfonylamino, [di-($C_1$-$C_6$)alkylamino]sulfonylamino, $C_3$-$C_6$-alkenylamino, $C_3$-$C_6$-alkynylamino, N—($C_2$-$C_6$-alkenyl)-N—($C_1$-$C_6$-alkyl)amino, N—($C_2$-$C_6$-alkynyl)-N—($C_1$-$C_6$-alkyl)amino, N($C_1$-$C_6$-alkoxy)-N—($C_1$-$C_6$-alkyl) amino, N—($C_2$-$C_6$-alkenyl)-N—($C_1$-$C_6$-alkoxy) amino, N—($C_2$-$C_6$-alkynyl)-N—($C_1$-$C_6$-alkoxy)-amino, $C_1$-$C_6$-alkylsulfonyl, tri-$C_1$-$C_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^{aa}$;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^b$ independently of one another are hydrogen, CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0, 1, 2 or 3;

$R^{15}$ is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^A R^B$, $S(O)_n R^y$, $S(O)_n NR^A R^B$, C(=O)$R^{25}$, CONR$^A$R$^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups $C_1$-$C_4$-alkyl, $C_3$-$C_4$-alkenyl, $C_3$-$C_4$-alkynyl, $C_1$-$C_4$-alkoxy, $C_3$-$C_6$-cycloalkyl, $C_5$-$C_6$-cycloalkenyl, $NR^A R^B$, $S(O)_n R^y$, $S(O)_n NR^A R^B$, C(=O)$R^{25}$, CONR$^A$R$^B$;

preferably is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^A R^B$, $S(O)_n R^y$, $S(O)_n NR^A R^B$, C(=O)$R^{25}$, CONR$^A$R$^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups $C_1$-$C_4$-alkyl, $C_3$-$C_4$-alkenyl and $C_3$-$C_4$-alkynyl;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy;

$D^1$ is carbonyl or a group D;

where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl, $C_3$-$C_4$-alkenyl or $C_3$-$C_4$-alkynyl;

$R^{17}$ is OH, $NH_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-haloalkyl, $C_1$-$C_4$-alkoxy-$C_1$-$C_4$-alkyl or C(=O)$R^{25}$;

$R^{18}$ is hydrogen, halogen, $C_1$-$C_4$-alkyl or $C_1$-$C_4$-haloalkyl, or $R^{18}$ and $R^{19}$ together are a covalent bond;

$R^{19}$, $R^{20}$, $R^{21}$, $R^{21}$ independently of one another are hydrogen, halogen, OH, CN, $NO_2$, $C_1$-$C_4$-alkyl, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

$R^{23}$, $R^{24}$ independently of one another are hydrogen, halogen, OH, haloalkyl, $NR^A R^B$, $NR^A C(O)R^{26}$, CN, $NO_2$, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)$R^{26}$, phenoxy or benzyloxy, where in groups $R^{23}$ and $R^{24}$ the carbon chains and/or the cyclic groups may carry 1, 2, 3 or 4 substituents $R^{aa}$;

$R^{26}$ is $C_1$-$C_4$-alkyl or $NR^A R^B$;

among the isoxazoline compounds of the piperazin compounds of formula III, preference is given to the piperazine compounds of the formula III, wherein A is phenyl or pyridyl where $R^a$ is attached in the ortho-position to the point of attachment of A to a carbon atom;

$R^a$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(=O)—$R^{a1}$;

$R^y$ is $C_1$-$C_6$-alkyl, $C_3$-$C_4$-alkenyl, $C_3$-$C_4$-alkynyl, $NR^A R^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$,$R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^b$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{15}$ is hydrogen, $C_1$-$C_{12}$-alkyl, $C_3$-$C_{12}$-alkenyl, $C_3$-$C_{12}$-alkynyl, $C_1$-$C_4$-alkoxy or C(=O)$R^{25}$, which can be partially or fully substituted by $R^{aa}$-groups;

preferably is hydrogen, $C_1$-$C_{12}$-alkyl, $C_3$-$C_{12}$-alkenyl, $C_3$-$C_{12}$-alkynyl, $C_1$-$C_4$-alkoxy or C(=O)$R^{25}$;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl;

$R^{17}$ is OH, $NH_2$, $C_1$-$C_4$-alkyl, $C_3$-$C_6$-cycloalkyl, $C_1$-$C_4$-haloalkyl or C(=O)$R^{25}$;

$R^{18}$ is hydrogen, or $R^{18}$ and $R^{19}$ together are a covalent bond;

$R^{19}$, $R^{20}$, $R^{21}$, $R^{21}$ independently of one another are hydrogen;

$R^{23}$, $R^{24}$ independently of one another are hydrogen, halogen or OH;

b12) from the group of the decoupler herbicides dinoseb, dinoterb and DNOC and its salts;

b13) from the group of the auxin herbicides 2,4-D and its salts and esters, 2,4-DB and its salts and esters, aminopyralid and its salts such as aminopyralid-tris (2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, MCPA and its salts and esters, MCPAthioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors diflufenzopyr, diflufenzopyr-sodium, naptalam and naptalam-sodium;

b15) from the group of the other herbicides bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flampropmethyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Preferred herbicides B which can be used in combination with the composition A according to the present invention are b1) from the group of the lipid biosynthesis inhibitors clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, benfuresate, dimepiperate, EPTC, esprocarb, ethofumesate, molinate, orbencarb, prosulfocarb, thiobencarb and triallate;

b2) from the group of the ALS inhibitors amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl and tritosulfuron;

b3) from the group of the photosynthesis inhibitors ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors acifluorfen-sodium, bencarbazone, benzfendizone, butafenacil, carfentrazone-ethyl, cinidon-ethyl, flufenpyrethyl, flumiclorac-pentyl, flumioxazin, fluoroglycofen-ethyl, fomesafen, lactofen, oxadiargyl, oxadiazon, oxyfluorfen, pentoxazone, pyraflufen-ethyl, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7) and 3-[7-fluoro-3-oxo-4-(prop-2-ynyl)-3,4-dihydro-2H-benzo[1,4]oxazin-6-yl]-1,5-dimethyl-6-thioxo[1,3,5]triazinan-2,4-dione;

b5) from the group of the bleacher herbicides aclonifen, beflubutamid, benzobicyclon, clomazone, diflufenican, flurochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

b6) from the group of the EPSP synthase inhibitors glyphosate, glyphosate-isopropylammonium and glyphosate-trimesium (sulfosate);

b7) from the group of the glutamine synthase inhibitors glufosinate, glufosinate-P, glufosinate-ammonium;

b8) from the group of the DHP synthase inhibitors asulam;

b9) from the group of the mitose inhibitors benfluralin, dithiopyr, ethalfluralin, oryzalin, pendimethalin, thiazopyr and trifluralin;

b10) from the group of the VLCFA inhibitors acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors dichlobenil, flupoxam, isoxaben, 1-Cyclohexyl-5-pentafluorphenyloxy-1$^4$-[1,2,4,6]thiatriazin-3-ylamine and the piperazine compounds of formula III as mentioned above;

b13) from the group of the auxin herbicides 2,4-D and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluroxypyr-meptyl, MCPA and its salts and esters, MCPB and its salts and esters, mecoprop-P and its salts and esters, picloram and its salts and esters, quinclorac, quinmerac, triclopyr and its salts and esters, and aminocyclopyrachlor and its salts and esters;

b14) from the group of the auxin transport inhibitors diflufenzopyr and diflufenzopyr-sodium;

b15) from the group of the other herbicides bromobutide, cinmethylin, cumyluron, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methyl-bromide, MSMA, oxaziclomefone, pyributicarb, triaziflam, tridiphane and 6-chloro-3-(2-cyclopropyl-6-methylphenoxy)-4-pyridazinol (CAS 499223-49-3) and its salts and esters.

Particularly preferred herbicides B which can be used in combination with the composition A according to the present invention are b1) from the group of the lipid biosynthesis inhibitors clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate;

b2) from the group of the ALS inhibitors bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron;

b3) from the group of the photosynthesis inhibitors ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100) and 3-[7-fluoro-3-oxo-4-(prop-2-ynyl)-3,4-dihydro-2H-benzo[1,4]oxazin-6-yl]-1,5-dimethyl-6-thioxo[1,3,5]triazinan-2,4-dione;

b5) from the group of the bleacher herbicides clomazone, diflufenican, flurochloridone, isoxaflutole, mesotrione, picolinafen, sulcotrione, tefuryltrione, tembotrione, topramezone, bicyclopyrone, amitrole and flumeturon;

b6) from the group of the EPSP synthase inhibitors glyphosate, glyphosate-isopropylammonium and glyphosate-trimesium (sulfosate);

b7) from the group of the glutamine synthase inhibitors glufosinate, glufosinate-P and glufosinate-ammonium;

b9) from the group of the mitose inhibitors pendimethalin and trifluralin;

b10) from the group of the VLCFA inhibitors acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and 11.9 as mentioned above;

b11) from the group of the cellulose biosynthesis inhibitors isoxaben and the piperazine compounds of formula III as mentioned above;

b13) from the group of the auxin herbicides 2,4-D and its salts and esters, aminopyralid and its salts and its esters, clopyralid and its salts and esters, dicamba and its salts and esters, fluroxypyr-meptyl, quinclorac, quinmerac and aminocyclopyrachlor and its salts and esters;

b14) from the group of the auxin transport inhibitors diflufenzopyr and diflufenzopyr-sodium, b15) from the group of the other herbicides dymron (=daimuron), indanofan, indaziflam, oxaziclomefone and triaziflam.

Moreover, it may be useful to apply the composition A in combination with safeners. Safeners are chemical compounds which prevent or reduce damage on useful plants without having a major impact on the herbicidal action of the composition A towards unwanted plants. They can be applied either before sowings (e.g. on seed treatments, shoots or seedlings) or in the pre-emergence application or post-emergence application of the useful plant. The safeners and the composition A can be applied simultaneously or in succession.

Furthermore, the safeners C, the composition A and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

The active compounds B of groups b1) to b15) and the active compounds C are known herbicides and safeners, see, for example, The Compendium of Pesticide Common Names (http//www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660. Further herbicidal compounds are known from WO 96/26202, WO 97/41116, WO 97/41117, WO 97/41118 and WO 01/83459 and also from W. Kramer et al. (ed.) "Modern Crop Protection Compounds", Vol. 1, Wiley VCH, 2007 and the literature cited therein.

The assignment of the active compounds to the respective mechanisms of action is based on current knowledge. If several mechanisms of action apply to one active compound, this substance was only assigned to one mechanism of action.

If the herbicides B and/or the safener C are capable of forming geometrical isomers, for example E/Z isomers, both the pure isomers and mixtures thereof may be used in the combinations according to the invention. If the herbicides B and/or the safener C have one of more centers of chirality and are thus present as enantiomers or diastereomers, both the pure enantiomers and diastereomers and mixtures thereof may be used in the combinations according to the invention.

If the herbicides B and/or the safener C have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl)-ammonium, benzyltrimethylammonium, benzyltriethylammonium, furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl) sulfoxonium.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Active compounds B and C having a carboxyl group can be employed in the form of the acid, in the form of an agriculturally suitable salt or else in the form of an agriculturally acceptable derivative in the combinations according to the invention, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the methoxyethyl, ethoxyethyl or butoxyethyl ester. An example of a straight-chain or branched $C_1$-$C_{10}$-alkylthio ester is the ethylthio ester.

According to a preferred embodiment of the invention, the herbicidal combination comprises as herbicidal active compound B or component B, at least one, preferably exactly one herbicide B.

According to another preferred embodiment of the invention, the herbicidal combination comprises as herbicidal active compound B or component B, at least two, preferably exactly two herbicides B different from each other.

According to another preferred embodiment of the invention, the herbicidal combination comprises as herbicidal active compound B or component B, at least three, preferably exactly three herbicides B different from each other.

According to another preferred embodiment of the invention, the herbicidal combination comprises as safening component C at least one, preferably exactly one safener C.

According to another preferred embodiment of the invention, the herbicidal combination comprises as component B, at least one, preferably exactly one herbicide B, and at least one, preferably exactly one, safener C.

According to another preferred embodiment of the invention, the herbicidal combination comprises as component B, preferably exactly two herbicides B different from each other, and at least one, preferably exactly one, safener C.

According to another preferred embodiment of the invention, the herbicidal combination comprises as component B, at least three, preferably exactly three herbicides B different from each other, and at least one, preferably exactly one, safener C.

According to a another preferred embodiment of the invention, the herbicidal combination comprises as component A the composition A, wherein the particles of benzoxazinone (I) are in a crystalline form, more preferably in form A, and as component B, at least one, preferably exactly one herbicide B.

According to another preferred embodiment of the invention, the herbicidal combination comprises as component A the composition A, wherein the particles of benzoxazinone (I) are in a crystalline form, more preferably in form A, and as component B, at least two, preferably exactly two herbicides B different from each other.

According to another preferred embodiment of the invention, the herbicidal combination comprises as component A the composition A, wherein the particles of benzoxazinone (I) are in a crystalline form, more preferably in form A, and as component B, at least three, preferably exactly three herbicides B different from each other.

According to another preferred embodiment of the invention, the herbicidal combination comprises as component A the composition A, wherein the particles of benzoxazinone (I) are in a crystalline form, more preferably in form A, and as component C at least one, preferably exactly one safener C.

According to another preferred embodiment of the invention, the herbicidal combination comprises as component A the composition A, wherein the particles of benzoxazinone (I) are in a crystalline form, more preferably in form A, as component B at least one, preferably exactly one herbicide B, and as component C at least one, preferably exactly one, safener C.

According to another preferred embodiment of the invention, the herbicidal combination comprises as component A the composition A, wherein the particles of benzoxazinone (I) are in a crystalline form, more preferably in form A, as component B preferably exactly two herbicides B different from each other, and as component C at least one, preferably exactly one, safener C.

According to another preferred embodiment of the invention, the herbicidal combination comprises as component A the composition A, wherein the particles of benzoxazinone (I) are in a crystalline form, more preferably in form A, and as component B, at least three, preferably exactly three herbicides B different from each other, and as component C at least one, preferably exactly one, safener C.

A first preferred embodiment of the invention relates to herbicidal combinations according to the invention comprising, in addition to the composition A, at least one and especially exactly one herbicidal compound from group b1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate.

A second preferred embodiment of the invention relates to herbicidal combinations according to the invention comprising, in addition to the composition A, at least one and especially exactly one herbicidal compound from group b2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

A third preferred embodiment of the invention relates to herbicidal combinations according to the invention comprising, in addition to the composition A, at least one and especially exactly one herbicidal compound from group b3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

A fourth preferred embodiment of the invention relates to herbicidal combinations according to the invention comprising, in addition to the composition A, at least one and especially exactly one herbicidal compound from group b4), in particular selected from the group consisting of flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS353292-31-6; S-3100) and 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione.

A fifth preferred embodiment of the invention relates to herbicidal combinations according to the invention comprising, in addition to the composition A, at least one and especially exactly one herbicidal compound from group b5), in particular selected from the group consisting of clomazone, diflufenican, flurochloridone, isoxaflutole, mesotrione, picolinafen, sulcotrione, tefuryltrione, tembotrione, topramezone, bicyclopyrone, amitrole and flumeturon.

A sixth preferred embodiment of the invention relates to herbicidal combinations according to the invention comprising, in addition to the composition A, at least one and especially exactly one herbicidal compound from group b6), in particular selected from the group consisting of glyphosate, glyphosate-isopropylammonium and glyphosate-trimesium (sulfosate).

A seventh preferred embodiment of the invention relates to herbicidal combinations according to the invention comprising, in addition to the composition A, at least one and especially exactly one herbicidal compound from group b7), in particular selected from the group consisting of glufosinate, glufosinate-P and glufosinate-ammonium.

An eighth preferred embodiment of the invention relates to herbicidal combinations according to the invention comprising, in addition to the composition A, at least one and especially exactly one herbicidal compound from group b9), in particular selected from the group consisting of pendimethalin and trifluralin.

A ninth preferred embodiment of the invention relates to herbicidal combinations according to the invention comprising, in addition to the composition A, at least one and especially exactly one herbicidal compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to combinations comprising in addition to the composition A, at least one and especially exactly one herbicidal compound from group b10), in particular selected from the group consisting of isoxazoline compounds of the formulae II.1, II.2, II.3, II.4, II.5, II.6, II.7, II.8 and II.9, as defined above.

A tenth preferred embodiment of the invention relates to herbicidal combinations according to the invention comprising, in addition to the composition A, at least one and especially exactly one herbicidal compound from group b11), in particular isoxaben. Likewise, preference is given to combinations comprising in addition to the composition A, at least one and especially exactly one herbicidal compound from group b10), in particular selected from the group consisting of piperazine compounds of formula III as defined above.

An eleventh preferred embodiment of the invention relates to herbicidal combinations according to the invention comprising, in addition to the composition A, at least one and especially exactly one herbicidal compound from group b13), in particular selected from the group consisting of 2,4-D and its salts and esters, aminopyralid and its salts such as aminopyralid-tris(2-hydroxypropyl)ammonium and its esters, clopyralid and its salts and esters, dicamba and its salts and esters, fluroxypyr-meptyl, quinclorac, quinmerac and aminocyclopyrachlor and its salts and esters.

A twelfth preferred embodiment of the invention relates to herbicidal combinations according to the invention comprising, in addition to the composition A, at least one and especially exactly one herbicidal compound from group b14), in particular selected from the group consisting of diflufenzopyr and diflufenzopyr-sodium.

A 13th preferred embodiment of the invention relates to herbicidal combinations according to the invention comprising, in addition to the composition A, at least one and especially exactly one herbicidal compound from group b15), in particular selected from the group consisting of dymron (=daimuron), indanofan, indaziflam, oxaziclomefone and triaziflam.

A 14th preferred embodiment of the invention relates to herbicidal combinations according to the invention comprising, in addition the composition A, at least one and especially exactly one herbicidal compound from the safeners C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Further preferred embodiments relate to ternary herbicidal combinations which correspond to the binary herbicidal combinations of embodiments 1 to 14 and additionally comprise a safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary herbicidal combinations" includes herbicidal combinations comprising the composition A and one or more, for example 1, 2 or 3, herbicides B or one or more safeners.

Correspondingly, the term "ternary herbicidal combinations" includes herbicidal combinations comprising the composition A, one or more, for example 1, 2 or 3, herbicides B and one or more, for example 1, 2 or 3, safeners C.

In binary herbicidal combinations comprising the composition A as component A and at least one herbicide B, the weight ratio of the active components AB is generally in the range of from 11000 to 10001, preferably in the range of from 1500 to 5001, in particular in the range of from 1250 to 2501 and particularly preferably in the range of from 175 to 751.

In binary herbicidal combinations comprising the composition A as component A and at least one safener C, the weight ratio of the active components AC is generally in the range of from 11000 to 10001, preferably in the range of from 1500 to 5001, in particular in the range of from 1250 to 2501 and particularly preferably in the range of from 175 to 751.

In ternary herbicidal combinations comprising the composition A as component A, at least one herbicide B and at least one safener C, the relative proportions by weight of the components AB are generally in the range of from 11000 to 10001, preferably in the range of from 1500 to 5001, in particular in the range of from 1250 to 2501 and particularly preferably in the range of from 175 to 751, the weight ratio of the components AC is generally in the range of from 11000 to 10001, preferably in the range of from 1500 to 5001, in particular in the range of from 1250 to 2501 and particularly preferably in the range of from 175 to 751, and the weight ratio of the components BC is generally in the range of from 11000 to 10001, preferably in the range of from 1500 to 5001, in particular in the range of from 1250 to 2501 and particularly preferably in the range of from 175 to 751. The weight ratio of components A+B to component C is preferably in the range of from 1500 to 5001, in particular in the range of from 1250 to 2501 and particularly preferably in the range of from 175 to 751.

Particularly preferred herbicides B are the herbicides B as defined above; in particular the herbicides B.1-B.141 listed below in table B

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-P-ethyl |
| B.6 | metamifop |
| B.7 | pinoxaden |
| B.8 | profoxydim |
| B.9 | sethoxydim |
| B.10 | tepraloxydim |
| B.11 | tralkoxydim |
| B.12 | esprocarb |
| B.13 | ethofumesate |

TABLE B-continued

| | Herbicide B |
|---|---|
| B.14 | molinate |
| B.15 | prosulfocarb |
| B.16 | thiobencarb |
| B.17 | triallate |
| B.18 | bensulfuron-methyl |
| B.19 | bispyribac-sodium |
| B.20 | cloransulam |
| B.21 | chlorsulfuron |
| B.22 | clorimuron |
| B.23 | cyclosulfamuron |
| B.24 | diclosulam |
| B.25 | florasulam |
| B.26 | flumetsulam |
| B.27 | flupyrsulfuron-methyl-sodium |
| B.28 | foramsulfuron |
| B.29 | imazamox |
| B.30 | imazapic |
| B.31 | imazapyr |
| B.32 | imazaquin |
| B.33 | imazethapyr |
| B.34 | imazosulfuron |
| B.35 | iodosulfuron-methyl-sodium |
| B.36 | mesosulfuron |
| B.37 | metazosulfuron |
| B.38 | metsulfuron |
| B.39 | metosulam |
| B.40 | nicosulfuron |
| B.41 | penoxsulam |
| B.42 | propoxycarbazon-sodium |
| B.43 | pyrazosulfuron-ethyl |
| B.44 | pyribenzoxim |
| B.45 | pyriftalid |
| B.46 | pyroxsulam |
| B.47 | rimsulfuron |
| B.48 | sulfosulfuron |
| B.49 | thiencarbazone-methyl |
| B.50 | thifensulfuron |
| B.51 | tribenuron |
| B.52 | tritosulfuron |
| B.53 | ametryne |
| B.54 | atrazine |
| B.55 | bentazon |
| B.56 | bromoxynil |
| B.57 | diuron |
| B.58 | fluometuron |
| B.59 | hexazinone |
| B.60 | isoproturon |
| B.61 | linuron |
| B.62 | metamitron |
| B.63 | metribuzin |
| B.64 | propanil |
| B.65 | simazin |
| B.66 | terbuthylazine |
| B.67 | terbutryn |
| B.68 | paraquat-dichloride |
| B.69 | acifluorfen |
| B.70 | butafenacil |
| B.71 | carfentrazone-ethyl |
| B.72 | flumioxazin |
| B.73 | fomesafen |
| B.74 | oxadiargyl |
| B.75 | oxyfluorfen |
| B.76 | saflufenacil |
| B.77 | sulfentrazone |
| B.78 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) |
| B.79 | 3-[7-fluoro-3-oxo-4-(prop-2-yn-yl)-3,4-dihydro-2H-benzo[1,4]-oxazin-6-yl]-1,5-dimethyl-6-thi-oxo-[1,3,5]triazinan-2,4-dione |
| B.80 | benzobicyclon |
| B.81 | clomazone |
| B.82 | diflufenican |
| B.83 | flurochloridone |
| B.84 | isoxaflutole |
| B.85 | mesotrione |
| B.86 | norflurazone |
| B.87 | picolinafen |
| B.88 | sulcotrione |

TABLE B-continued

| | Herbicide B |
|---|---|
| B.89 | tefuryltrione |
| B.90 | tembotrione |
| B.91 | topramezone |
| B.92 | bicyclopyrone |
| B.93 | amitrole |
| B.94 | fluometuron |
| B.95 | glyphosate |
| B.96 | glyphosate-isopropylammonium |
| B.97 | glyphosate-trimesium (sulfosate) |
| B.98 | glufosinate |
| B.99 | glufosinate-P |
| B.100 | glufosinate-ammonium |
| B.101 | pendimethalin |
| B.102 | trifluralin |
| B.103 | acetochlor |
| B.104 | butachlor |
| B.105 | cafenstrole |
| B.106 | dimethenamid-P |
| B.107 | fentrazamide |
| B.108 | flufenacet |
| B.109 | mefenacet |
| B.110 | metazachlor |
| B.111 | metolachlor |
| B.112 | S-metolachlor |
| B.113 | pretilachlor |
| B.114 | fenoxasulfone |
| B.115 | isoxaben |
| B.116 | pyroxasulfone |
| B.117 | 2,4-D |
| B.118 | aminopyralid |
| B.119 | clopyralid |
| B.120 | dicamba |
| B.121 | fluroxypyr-meptyl |
| B.122 | MCPA |
| B.123 | quinclorac |
| B.124 | quinmerac |
| B.125 | aminocyclopyrachlor |
| B.126 | diflufenzopyr |
| B.127 | diflufenzopyr-sodium |
| B.128 | dymron |
| B.129 | indanofan |
| B.130 | indaziflam |
| B.131 | oxaziclomefone |
| B.132 | triaziflam |
| B.133 | II.1 |
| B.134 | II.2 |
| B.135 | II.3 |
| B.136 | II.4 |
| B.137 | II.5 |
| B.138 | II.6 |
| B.139 | II.7 |
| B.140 | II.8 |
| B.141 | II.9 |

Particularly preferred safeners C, which, as component C, are constituent of the herbicidal combinations according to the invention are the safeners C as defined above; in particular the safeners C.1-C.12 listed below in table C

TABLE C

| | Safener C |
|---|---|
| C.1 | benoxacor |
| C.2 | cloquintocet |
| C.3 | cyprosulfamide |
| C.4 | dichlormid |
| C.5 | fenclorim |
| C.6 | fenchlorazole |
| C.7 | furilazole |
| C.8 | isoxadifen |
| C.9 | mefenpyr |
| C.10 | 4-(dichloroacetyl)-1-oxa-4-azaspiro[4.5]decane (MON4660, CAS 71526-07-3) |

TABLE C-continued

| | Safener C |
|---|---|
| C.11 | 2,2,5-trimethyl-3-(dichloroacetyl)-1,3-oxazolidine (R-29148, CAS 52836-31-4) |
| C.12 | naphtalic acid anhydride |

The weight ratios of the individual components in the preferred herbicidal combinations mentioned below are within the limits given above, in particular within the preferred limits.

Particularly preferred are the herbicidal combinations mentioned below, comprising the composition A as defined and the substance(s) as defined in the respective row of table 1;

especially preferred comprising as only herbicidal active compounds the composition A as defined and the substance(s) as defined in the respective row of table 1;

most preferably comprising as only active compounds the composition A as defined and the substance(s) as defined in the respective row of table 1.

Particularly preferred are the herbicidal combinations 1.1 to 1.1833 comprising the composition A and the substance(s) as defined in the respective row of table 1

TABLE 1

(herbicidal combinations 1.1 to 1.1833):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |

TABLE 1-continued (herbicidal combinations 1.1 to 1.1833):

| comp. no. | herbicide B | safener C |
|---|---|---|
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.1 | C.1 |
| 1.143 | B.2 | C.1 |
| 1.144 | B.3 | C.1 |
| 1.145 | B.4 | C.1 |
| 1.146 | B.5 | C.1 |
| 1.147 | B.6 | C.1 |
| 1.148 | B.7 | C.1 |
| 1.149 | B.8 | C.1 |
| 1.150 | B.9 | C.1 |
| 1.151 | B.10 | C.1 |
| 1.152 | B.11 | C.1 |
| 1.153 | B.12 | C.1 |
| 1.154 | B.13 | C.1 |
| 1.155 | B.14 | C.1 |
| 1.156 | B.15 | C.1 |
| 1.157 | B.16 | C.1 |
| 1.158 | B.17 | C.1 |
| 1.159 | B.18 | C.1 |
| 1.160 | B.19 | C.1 |
| 1.161 | B.20 | C.1 |
| 1.162 | B.21 | C.1 |
| 1.163 | B.22 | C.1 |
| 1.164 | B.23 | C.1 |
| 1.165 | B.24 | C.1 |
| 1.166 | B.25 | C.1 |
| 1.167 | B.26 | C.1 |
| 1.168 | B.27 | C.1 |
| 1.169 | B.28 | C.1 |
| 1.170 | B.29 | C.1 |
| 1.171 | B.30 | C.1 |
| 1.172 | B.31 | C.1 |
| 1.173 | B.32 | C.1 |
| 1.174 | B.33 | C.1 |
| 1.175 | B.34 | C.1 |
| 1.176 | B.35 | C.1 |
| 1.177 | B.36 | C.1 |
| 1.178 | B.37 | C.1 |
| 1.179 | B.38 | C.1 |
| 1.180 | B.39 | C.1 |
| 1.181 | B.40 | C.1 |
| 1.182 | B.41 | C.1 |
| 1.183 | B.42 | C.1 |
| 1.184 | B.43 | C.1 |
| 1.185 | B.44 | C.1 |
| 1.186 | B.45 | C.1 |
| 1.187 | B.46 | C.1 |
| 1.188 | B.47 | C.1 |
| 1.189 | B.48 | C.1 |
| 1.190 | B.49 | C.1 |
| 1.191 | B.50 | C.1 |
| 1.192 | B.51 | C.1 |
| 1.193 | B.52 | C.1 |

TABLE 1-continued (herbicidal combinations 1.1 to 1.1833):

| comp. no. | herbicide B | safener C |
|---|---|---|
| 1.194 | B.53 | C.1 |
| 1.195 | B.54 | C.1 |
| 1.196 | B.55 | C.1 |
| 1.197 | B.56 | C.1 |
| 1.198 | B.57 | C.1 |
| 1.199 | B.58. | C.1 |
| 1.200 | B.59 | C.1 |
| 1.201 | B.60 | C.1 |
| 1.202 | B.61 | C.1 |
| 1.203 | B.62 | C.1 |
| 1.204 | B.63 | C.1 |
| 1.205 | B.64 | C.1 |
| 1.206 | B.65 | C.1 |
| 1.207 | B.66 | C.1 |
| 1.208 | B.67 | C.1 |
| 1.209 | B.68 | C.1 |
| 1.210 | B.69 | C.1 |
| 1.211 | B.70 | C.1 |
| 1.212 | B.71 | C.1 |
| 1.213 | B.72 | C.1 |
| 1.214 | B.73 | C.1 |
| 1.215 | B.74 | C.1 |
| 1.216 | B.75 | C.1 |
| 1.217 | B.76 | C.1 |
| 1.218 | B.77 | C.1 |
| 1.219 | B.78 | C.1 |
| 1.220 | B.79 | C.1 |
| 1.221 | B.80 | C.1 |
| 1.222 | B.81 | C.1 |
| 1.223 | B.82 | C.1 |
| 1.224 | B.83 | C.1 |
| 1.225 | B.84 | C.1 |
| 1.226 | B.85 | C.1 |
| 1.227 | B.86 | C.1 |
| 1.228 | B.87 | C.1 |
| 1.229 | B.88 | C.1 |
| 1.230 | B.89 | C.1 |
| 1.231 | B.90 | C.1 |
| 1.232 | B.91 | C.1 |
| 1.233 | B.92 | C.1 |
| 1.234 | B.93 | C.1 |
| 1.235 | B.94 | C.1 |
| 1.236 | B.95 | C.1 |
| 1.237 | B.96 | C.1 |
| 1.238 | B.97 | C.1 |
| 1.239 | B.98 | C.1 |
| 1.240 | B.99 | C.1 |
| 1.241 | B.100 | C.1 |
| 1.242 | B.101 | C.1 |
| 1.243 | B.102 | C.1 |
| 1.244 | B.103 | C.1 |
| 1.245 | B.104 | C.1 |
| 1.246 | B.105 | C.1 |
| 1.247 | B.106 | C.1 |
| 1.248 | B.107 | C.1 |
| 1.249 | B.108 | C.1 |
| 1.250 | B.109 | C.1 |
| 1.251 | B.110 | C.1 |
| 1.252 | B.111 | C.1 |
| 1.253 | B.112 | C.1 |
| 1.254 | B.113 | C.1 |
| 1.255 | B.114 | C.1 |
| 1.256 | B.115 | C.1 |
| 1.257 | B.116 | C.1 |
| 1.258 | B.117 | C.1 |
| 1.259 | B.118 | C.1 |
| 1.260 | B.119 | C.1 |
| 1.261 | B.120 | C.1 |
| 1.262 | B.121 | C.1 |
| 1.263 | B.122 | C.1 |
| 1.264 | B.123 | C.1 |
| 1.265 | B.124 | C.1 |
| 1.266 | B.125 | C.1 |
| 1.267 | B.126 | C.1 |
| 1.268 | B.127 | C.1 |
| 1.269 | B.128 | C.1 |
| 1.270 | B.129 | C.1 |
| 1.271 | B.130 | C.1 |
| 1.272 | B.131 | C.1 |
| 1.273 | B.132 | C.1 |
| 1.274 | B.133 | C.1 |
| 1.275 | B.134 | C.1 |
| 1.276 | B.135 | C.1 |
| 1.277 | B.136 | C.1 |
| 1.278 | B.137 | C.1 |
| 1.279 | B.138 | C.1 |
| 1.280 | B.139 | C.1 |
| 1.281 | B.140 | C.1 |
| 1.282 | B.141 | C.1 |
| 1.283 | B.1 | C.2 |
| 1.284 | B.2 | C.2 |
| 1.285 | B.3 | C.2 |
| 1.286 | B.4 | C.2 |
| 1.287 | B.5 | C.2 |
| 1.288 | B.6 | C.2 |
| 1.289 | B.7 | C.2 |
| 1.290 | B.8 | C.2 |
| 1.291 | B.9 | C.2 |
| 1.292 | B.10 | C.2 |
| 1.293 | B.11 | C.2 |
| 1.294 | B.12 | C.2 |
| 1.295 | B.13 | C.2 |
| 1.296 | B.14 | C.2 |
| 1.297 | B.15 | C.2 |
| 1.298 | B.16 | C.2 |
| 1.299 | B.17 | C.2 |
| 1.300 | B.18 | C.2 |
| 1.301 | B.19 | C.2 |
| 1.302 | B.20 | C.2 |
| 1.303 | B.21 | C.2 |
| 1.304 | B.22 | C.2 |
| 1.305 | B.23 | C.2 |
| 1.306 | B.24 | C.2 |
| 1.307 | B.25 | C.2 |
| 1.308 | B.26 | C.2 |
| 1.309 | B.27 | C.2 |
| 1.310 | B.28 | C.2 |
| 1.311 | B.29 | C.2 |
| 1.312 | B.30 | C.2 |
| 1.313 | B.31 | C.2 |
| 1.314 | B.32 | C.2 |
| 1.315 | B.33 | C.2 |
| 1.316 | B.34 | C.2 |
| 1.317 | B.35 | C.2 |
| 1.318 | B.36 | C.2 |
| 1.319 | B.37 | C.2 |
| 1.320 | B.38 | C.2 |
| 1.321 | B.39 | C.2 |
| 1.322 | B.40 | C.2 |
| 1.323 | B.41 | C.2 |
| 1.324 | B.42 | C.2 |
| 1.325 | B.43 | C.2 |
| 1.326 | B.44 | C.2 |
| 1.327 | B.45 | C.2 |
| 1.328 | B.46 | C.2 |
| 1.329 | B.47 | C.2 |
| 1.330 | B.48 | C.2 |
| 1.331 | B.49 | C.2 |
| 1.332 | B.50 | C.2 |
| 1.333 | B.51 | C.2 |
| 1.334 | B.52 | C.2 |
| 1.335 | B.53 | C.2 |
| 1.336 | B.54 | C.2 |
| 1.337 | B.55 | C.2 |
| 1.338 | B.56 | C.2 |
| 1.339 | B.57 | C.2 |
| 1.340 | B.58. | C.2 |
| 1.341 | B.59 | C.2 |
| 1.342 | B.60 | C.2 |
| 1.343 | B.61 | C.2 |

TABLE 1-continued (herbicidal combinations 1.1 to 1.1833):

| comp. no. | herbicide B | safener C |
|---|---|---|
| 1.344 | B.62 | C.2 |
| 1.345 | B.63 | C.2 |
| 1.346 | B.64 | C.2 |
| 1.347 | B.65 | C.2 |
| 1.348 | B.66 | C.2 |
| 1.349 | B.67 | C.2 |
| 1.350 | B.68 | C.2 |
| 1.351 | B.69 | C.2 |
| 1.352 | B.70 | C.2 |
| 1.353 | B.71 | C.2 |
| 1.354 | B.72 | C.2 |
| 1.355 | B.73 | C.2 |
| 1.356 | B.74 | C.2 |
| 1.357 | B.75 | C.2 |
| 1.358 | B.76 | C.2 |
| 1.359 | B.77 | C.2 |
| 1.360 | B.78 | C.2 |
| 1.361 | B.79 | C.2 |
| 1.362 | B.80 | C.2 |
| 1.363 | B.81 | C.2 |
| 1.364 | B.82 | C.2 |
| 1.365 | B.83 | C.2 |
| 1.366 | B.84 | C.2 |
| 1.367 | B.85 | C.2 |
| 1.368 | B.86 | C.2 |
| 1.369 | B.87 | C.2 |
| 1.370 | B.88 | C.2 |
| 1.371 | B.89 | C.2 |
| 1.372 | B.90 | C.2 |
| 1.373 | B.91 | C.2 |
| 1.374 | B.92 | C.2 |
| 1.375 | B.93 | C.2 |
| 1.376 | B.94 | C.2 |
| 1.377 | B.95 | C.2 |
| 1.378 | B.96 | C.2 |
| 1.379 | B.97 | C.2 |
| 1.380 | B.98 | C.2 |
| 1.381 | B.99 | C.2 |
| 1.382 | B.100 | C.2 |
| 1.383 | B.101 | C.2 |
| 1.384 | B.102 | C.2 |
| 1.385 | B.103 | C.2 |
| 1.386 | B.104 | C.2 |
| 1.387 | B.105 | C.2 |
| 1.388 | B.106 | C.2 |
| 1.389 | B.107 | C.2 |
| 1.390 | B.108 | C.2 |
| 1.391 | B.109 | C.2 |
| 1.392 | B.110 | C.2 |
| 1.393 | B.111 | C.2 |
| 1.394 | B.112 | C.2 |
| 1.395 | B.113 | C.2 |
| 1.396 | B.114 | C.2 |
| 1.397 | B.115 | C.2 |
| 1.398 | B.116 | C.2 |
| 1.399 | B.117 | C.2 |
| 1.400 | B.118 | C.2 |
| 1.401 | B.119 | C.2 |
| 1.402 | B.120 | C.2 |
| 1.403 | B.121 | C.2 |
| 1.404 | B.122 | C.2 |
| 1.405 | B.123 | C.2 |
| 1.406 | B.124 | C.2 |
| 1.407 | B.125 | C.2 |
| 1.408 | B.126 | C.2 |
| 1.409 | B.127 | C.2 |
| 1.410 | B.128 | C.2 |
| 1.411 | B.129 | C.2 |
| 1.412 | B.130 | C.2 |
| 1.413 | B.131 | C.2 |
| 1.414 | B.132 | C.2 |
| 1.415 | B.133 | C.2 |
| 1.416 | B.134 | C.2 |
| 1.417 | B.135 | C.2 |
| 1.418 | B.136 | C.2 |
| 1.419 | B.137 | C.2 |
| 1.420 | B.138 | C.2 |
| 1.421 | B.139 | C.2 |
| 1.422 | B.140 | C.2 |
| 1.423 | B.141 | C.2 |
| 1.424 | B.1 | C.3 |
| 1.425 | B.2 | C.3 |
| 1.426 | B.3 | C.3 |
| 1.427 | B.4 | C.3 |
| 1.428 | B.5 | C.3 |
| 1.429 | B.6 | C.3 |
| 1.430 | B.7 | C.3 |
| 1.431 | B.8 | C.3 |
| 1.432 | B.9 | C.3 |
| 1.433 | B.10 | C.3 |
| 1.434 | B.11 | C.3 |
| 1.435 | B.12 | C.3 |
| 1.436 | B.13 | C.3 |
| 1.437 | B.14 | C.3 |
| 1.438 | B.15 | C.3 |
| 1.439 | B.16 | C.3 |
| 1.440 | B.17 | C.3 |
| 1.441 | B.18 | C.3 |
| 1.442 | B.19 | C.3 |
| 1.443 | B.20 | C.3 |
| 1.444 | B.21 | C.3 |
| 1.445 | B.22 | C.3 |
| 1.446 | B.23 | C.3 |
| 1.447 | B.24 | C.3 |
| 1.448 | B.25 | C.3 |
| 1.449 | B.26 | C.3 |
| 1.450 | B.27 | C.3 |
| 1.451 | B.28 | C.3 |
| 1.452 | B.29 | C.3 |
| 1.453 | B.30 | C.3 |
| 1.454 | B.31 | C.3 |
| 1.455 | B.32 | C.3 |
| 1.456 | B.33 | C.3 |
| 1.457 | B.34 | C.3 |
| 1.458 | B.35 | C.3 |
| 1.459 | B.36 | C.3 |
| 1.460 | B.37 | C.3 |
| 1.461 | B.38 | C.3 |
| 1.462 | B.39 | C.3 |
| 1.463 | B.40 | C.3 |
| 1.464 | B.41 | C.3 |
| 1.465 | B.42 | C.3 |
| 1.466 | B.43 | C.3 |
| 1.467 | B.44 | C.3 |
| 1.468 | B.45 | C.3 |
| 1.469 | B.46 | C.3 |
| 1.470 | B.47 | C.3 |
| 1.471 | B.48 | C.3 |
| 1.472 | B.49 | C.3 |
| 1.473 | B.50 | C.3 |
| 1.474 | B.51 | C.3 |
| 1.475 | B.52 | C.3 |
| 1.476 | B.53 | C.3 |
| 1.477 | B.54 | C.3 |
| 1.478 | B.55 | C.3 |
| 1.479 | B.56 | C.3 |
| 1.480 | B.57 | C.3 |
| 1.481 | B.58. | C.3 |
| 1.482 | B.59 | C.3 |
| 1.483 | B.60 | C.3 |
| 1.484 | B.61 | C.3 |
| 1.485 | B.62 | C.3 |
| 1.486 | B.63 | C.3 |
| 1.487 | B.64 | C.3 |
| 1.488 | B.65 | C.3 |
| 1.489 | B.66 | C.3 |
| 1.490 | B.67 | C.3 |
| 1.491 | B.68 | C.3 |
| 1.492 | B.69 | C.3 |
| 1.493 | B.70 | C.3 |

TABLE 1-continued (herbicidal combinations 1.1 to 1.1833):

| comp. no. | herbicide B | safener C |
|---|---|---|
| 1.494 | B.71 | C.3 |
| 1.495 | B.72 | C.3 |
| 1.496 | B.73 | C.3 |
| 1.497 | B.74 | C.3 |
| 1.498 | B.75 | C.3 |
| 1.499 | B.76 | C.3 |
| 1.500 | B.77 | C.3 |
| 1.501 | B.78 | C.3 |
| 1.502 | B.79 | C.3 |
| 1.503 | B.80 | C.3 |
| 1.504 | B.81 | C.3 |
| 1.505 | B.82 | C.3 |
| 1.506 | B.83 | C.3 |
| 1.507 | B.84 | C.3 |
| 1.508 | B.85 | C.3 |
| 1.509 | B.86 | C.3 |
| 1.510 | B.87 | C.3 |
| 1.511 | B.88 | C.3 |
| 1.512 | B.89 | C.3 |
| 1.513 | B.90 | C.3 |
| 1.514 | B.91 | C.3 |
| 1.515 | B.92 | C.3 |
| 1.516 | B.93 | C.3 |
| 1.517 | B.94 | C.3 |
| 1.518 | B.95 | C.3 |
| 1.519 | B.96 | C.3 |
| 1.520 | B.97 | C.3 |
| 1.521 | B.98 | C.3 |
| 1.522 | B.99 | C.3 |
| 1.523 | B.100 | C.3 |
| 1.524 | B.101 | C.3 |
| 1.525 | B.102 | C.3 |
| 1.526 | B.103 | C.3 |
| 1.527 | B.104 | C.3 |
| 1.528 | B.105 | C.3 |
| 1.529 | B.106 | C.3 |
| 1.530 | B.107 | C.3 |
| 1.531 | B.108 | C.3 |
| 1.532 | B.109 | C.3 |
| 1.533 | B.110 | C.3 |
| 1.534 | B.111 | C.3 |
| 1.535 | B.112 | C.3 |
| 1.536 | B.113 | C.3 |
| 1.537 | B.114 | C.3 |
| 1.538 | B.115 | C.3 |
| 1.539 | B.116 | C.3 |
| 1.540 | B.117 | C.3 |
| 1.541 | B.118 | C.3 |
| 1.542 | B.119 | C.3 |
| 1.543 | B.120 | C.3 |
| 1.544 | B.121 | C.3 |
| 1.545 | B.122 | C.3 |
| 1.546 | B.123 | C.3 |
| 1.547 | B.124 | C.3 |
| 1.548 | B.125 | C.3 |
| 1.549 | B.126 | C.3 |
| 1.550 | B.127 | C.3 |
| 1.551 | B.128 | C.3 |
| 1.552 | B.129 | C.3 |
| 1.553 | B.130 | C.3 |
| 1.554 | B.131 | C.3 |
| 1.555 | B.132 | C.3 |
| 1.556 | B.133 | C.3 |
| 1.557 | B.134 | C.3 |
| 1.558 | B.135 | C.3 |
| 1.559 | B.136 | C.3 |
| 1.560 | B.137 | C.3 |
| 1.561 | B.138 | C.3 |
| 1.562 | B.139 | C.3 |
| 1.563 | B.140 | C.3 |
| 1.564 | B.141 | C.3 |
| 1.565 | B.1 | C.4 |
| 1.566 | B.2 | C.4 |
| 1.567 | B.3 | C.4 |
| 1.568 | B.4 | C.4 |
| 1.569 | B.5 | C.4 |
| 1.570 | B.6 | C.4 |
| 1.571 | B.7 | C.4 |
| 1.572 | B.8 | C.4 |
| 1.573 | B.9 | C.4 |
| 1.574 | B.10 | C.4 |
| 1.575 | B.11 | C.4 |
| 1.576 | B.12 | C.4 |
| 1.577 | B.13 | C.4 |
| 1.578 | B.14 | C.4 |
| 1.579 | B.15 | C.4 |
| 1.580 | B.16 | C.4 |
| 1.581 | B.17 | C.4 |
| 1.582 | B.18 | C.4 |
| 1.583 | B.19 | C.4 |
| 1.584 | B.20 | C.4 |
| 1.585 | B.21 | C.4 |
| 1.586 | B.22 | C.4 |
| 1.587 | B.23 | C.4 |
| 1.588 | B.24 | C.4 |
| 1.589 | B.25 | C.4 |
| 1.590 | B.26 | C.4 |
| 1.591 | B.27 | C.4 |
| 1.592 | B.28 | C.4 |
| 1.593 | B.29 | C.4 |
| 1.594 | B.30 | C.4 |
| 1.595 | B.31 | C.4 |
| 1.596 | B.32 | C.4 |
| 1.597 | B.33 | C.4 |
| 1.598 | B.34 | C.4 |
| 1.599 | B.35 | C.4 |
| 1.600 | B.36 | C.4 |
| 1.601 | B.37 | C.4 |
| 1.602 | B.38 | C.4 |
| 1.603 | B.39 | C.4 |
| 1.604 | B.40 | C.4 |
| 1.605 | B.41 | C.4 |
| 1.606 | B.42 | C.4 |
| 1.607 | B.43 | C.4 |
| 1.608 | B.44 | C.4 |
| 1.609 | B.45 | C.4 |
| 1.610 | B.46 | C.4 |
| 1.611 | B.47 | C.4 |
| 1.612 | B.48 | C.4 |
| 1.613 | B.49 | C.4 |
| 1.614 | B.50 | C.4 |
| 1.615 | B.51 | C.4 |
| 1.616 | B.52 | C.4 |
| 1.617 | B.53 | C.4 |
| 1.618 | B.54 | C.4 |
| 1.619 | B.55 | C.4 |
| 1.620 | B.56 | C.4 |
| 1.621 | B.57 | C.4 |
| 1.622 | B.58. | C.4 |
| 1.623 | B.59 | C.4 |
| 1.624 | B.60 | C.4 |
| 1.625 | B.61 | C.4 |
| 1.626 | B.62 | C.4 |
| 1.627 | B.63 | C.4 |
| 1.628 | B.64 | C.4 |
| 1.629 | B.65 | C.4 |
| 1.630 | B.66 | C.4 |
| 1.631 | B.67 | C.4 |
| 1.632 | B.68 | C.4 |
| 1.633 | B.69 | C.4 |
| 1.634 | B.70 | C.4 |
| 1.635 | B.71 | C.4 |
| 1.636 | B.72 | C.4 |
| 1.637 | B.73 | C.4 |
| 1.638 | B.74 | C.4 |
| 1.639 | B.75 | C.4 |
| 1.640 | B.76 | C.4 |
| 1.641 | B.77 | C.4 |
| 1.642 | B.78 | C.4 |
| 1.643 | B.79 | C.4 |

TABLE 1-continued (herbicidal combinations 1.1 to 1.1833):

| comp. no. | herbicide B | safener C |
|---|---|---|
| 1.644 | B.80 | C.4 |
| 1.645 | B.81 | C.4 |
| 1.646 | B.82 | C.4 |
| 1.647 | B.83 | C.4 |
| 1.648 | B.84 | C.4 |
| 1.649 | B.85 | C.4 |
| 1.650 | B.86 | C.4 |
| 1.651 | B.87 | C.4 |
| 1.652 | B.88 | C.4 |
| 1.653 | B.89 | C.4 |
| 1.654 | B.90 | C.4 |
| 1.655 | B.91 | C.4 |
| 1.656 | B.92 | C.4 |
| 1.657 | B.93 | C.4 |
| 1.658 | B.94 | C.4 |
| 1.659 | B.95 | C.4 |
| 1.660 | B.96 | C.4 |
| 1.661 | B.97 | C.4 |
| 1.662 | B.98 | C.4 |
| 1.663 | B.99 | C.4 |
| 1.664 | B.100 | C.4 |
| 1.665 | B.101 | C.4 |
| 1.666 | B.102 | C.4 |
| 1.667 | B.103 | C.4 |
| 1.668 | B.104 | C.4 |
| 1.669 | B.105 | C.4 |
| 1.670 | B.106 | C.4 |
| 1.671 | B.107 | C.4 |
| 1.672 | B.108 | C.4 |
| 1.673 | B.109 | C.4 |
| 1.674 | B.110 | C.4 |
| 1.675 | B.111 | C.4 |
| 1.676 | B.112 | C.4 |
| 1.677 | B.113 | C.4 |
| 1.678 | B.114 | C.4 |
| 1.679 | B.115 | C.4 |
| 1.680 | B.116 | C.4 |
| 1.681 | B.117 | C.4 |
| 1.682 | B.118 | C.4 |
| 1.683 | B.119 | C.4 |
| 1.684 | B.120 | C.4 |
| 1.685 | B.121 | C.4 |
| 1.686 | B.122 | C.4 |
| 1.687 | B.123 | C.4 |
| 1.688 | B.124 | C.4 |
| 1.689 | B.125 | C.4 |
| 1.690 | B.126 | C.4 |
| 1.691 | B.127 | C.4 |
| 1.692 | B.128 | C.4 |
| 1.693 | B.129 | C.4 |
| 1.694 | B.130 | C.4 |
| 1.695 | B.131 | C.4 |
| 1.696 | B.132 | C.4 |
| 1.697 | B.133 | C.4 |
| 1.698 | B.134 | C.4 |
| 1.699 | B.135 | C.4 |
| 1.700 | B.136 | C.4 |
| 1.701 | B.137 | C.4 |
| 1.702 | B.138 | C.4 |
| 1.703 | B.139 | C.4 |
| 1.704 | B.140 | C.4 |
| 1.705 | B.141 | C.4 |
| 1.706 | B.1 | C.5 |
| 1.707 | B.2 | C.5 |
| 1.708 | B.3 | C.5 |
| 1.709 | B.4 | C.5 |
| 1.710 | B.5 | C.5 |
| 1.711 | B.6 | C.5 |
| 1.712 | B.7 | C.5 |
| 1.713 | B.8 | C.5 |
| 1.714 | B.9 | C.5 |
| 1.715 | B.10 | C.5 |
| 1.716 | B.11 | C.5 |
| 1.717 | B.12 | C.5 |
| 1.718 | B.13 | C.5 |
| 1.719 | B.14 | C.5 |
| 1.720 | B.15 | C.5 |
| 1.721 | B.16 | C.5 |
| 1.722 | B.17 | C.5 |
| 1.723 | B.18 | C.5 |
| 1.724 | B.19 | C.5 |
| 1.725 | B.20 | C.5 |
| 1.726 | B.21 | C.5 |
| 1.727 | B.22 | C.5 |
| 1.728 | B.23 | C.5 |
| 1.729 | B.24 | C.5 |
| 1.730 | B.25 | C.5 |
| 1.731 | B.26 | C.5 |
| 1.732 | B.27 | C.5 |
| 1.733 | B.28 | C.5 |
| 1.734 | B.29 | C.5 |
| 1.735 | B.30 | C.5 |
| 1.736 | B.31 | C.5 |
| 1.737 | B.32 | C.5 |
| 1.738 | B.33 | C.5 |
| 1.739 | B.34 | C.5 |
| 1.740 | B.35 | C.5 |
| 1.741 | B.36 | C.5 |
| 1.742 | B.37 | C.5 |
| 1.743 | B.38 | C.5 |
| 1.744 | B.39 | C.5 |
| 1.745 | B.40 | C.5 |
| 1.746 | B.41 | C.5 |
| 1.747 | B.42 | C.5 |
| 1.748 | B.43 | C.5 |
| 1.749 | B.44 | C.5 |
| 1.750 | B.45 | C.5 |
| 1.751 | B.46 | C.5 |
| 1.752 | B.47 | C.5 |
| 1.753 | B.48 | C.5 |
| 1.754 | B.49 | C.5 |
| 1.755 | B.50 | C.5 |
| 1.756 | B.51 | C.5 |
| 1.757 | B.52 | C.5 |
| 1.758 | B.53 | C.5 |
| 1.759 | B.54 | C.5 |
| 1.760 | B.55 | C.5 |
| 1.761 | B.56 | C.5 |
| 1.762 | B.57 | C.5 |
| 1.763 | B.58. | C.5 |
| 1.764 | B.59 | C.5 |
| 1.765 | B.60 | C.5 |
| 1.766 | B.61 | C.5 |
| 1.767 | B.62 | C.5 |
| 1.768 | B.63 | C.5 |
| 1.769 | B.64 | C.5 |
| 1.770 | B.65 | C.5 |
| 1.771 | B.66 | C.5 |
| 1.772 | B.67 | C.5 |
| 1.773 | B.68 | C.5 |
| 1.774 | B.69 | C.5 |
| 1.775 | B.70 | C.5 |
| 1.776 | B.71 | C.5 |
| 1.777 | B.72 | C.5 |
| 1.778 | B.73 | C.5 |
| 1.779 | B.74 | C.5 |
| 1.780 | B.75 | C.5 |
| 1.781 | B.76 | C.5 |
| 1.782 | B.77 | C.5 |
| 1.783 | B.78 | C.5 |
| 1.784 | B.79 | C.5 |
| 1.785 | B.80 | C.5 |
| 1.786 | B.81 | C.5 |
| 1.787 | B.82 | C.5 |
| 1.788 | B.83 | C.5 |
| 1.789 | B.84 | C.5 |
| 1.790 | B.85 | C.5 |
| 1.791 | B.86 | C.5 |
| 1.792 | B.87 | C.5 |
| 1.793 | B.88 | C.5 |

TABLE 1-continued (herbicidal combinations 1.1 to 1.1833):

| comp. no. | herbicide B | safener C |
|---|---|---|
| 1.794 | B.89 | C.5 |
| 1.795 | B.90 | C.5 |
| 1.796 | B.91 | C.5 |
| 1.797 | B.92 | C.5 |
| 1.798 | B.93 | C.5 |
| 1.799 | B.94 | C.5 |
| 1.800 | B.95 | C.5 |
| 1.801 | B.96 | C.5 |
| 1.802 | B.97 | C.5 |
| 1.803 | B.98 | C.5 |
| 1.804 | B.99 | C.5 |
| 1.805 | B.100 | C.5 |
| 1.806 | B.101 | C.5 |
| 1.807 | B.102 | C.5 |
| 1.808 | B.103 | C.5 |
| 1.809 | B.104 | C.5 |
| 1.810 | B.105 | C.5 |
| 1.811 | B.106 | C.5 |
| 1.812 | B.107 | C.5 |
| 1.813 | B.108 | C.5 |
| 1.814 | B.109 | C.5 |
| 1.815 | B.110 | C.5 |
| 1.816 | B.111 | C.5 |
| 1.817 | B.112 | C.5 |
| 1.818 | B.113 | C.5 |
| 1.819 | B.114 | C.5 |
| 1.820 | B.115 | C.5 |
| 1.821 | B.116 | C.5 |
| 1.822 | B.117 | C.5 |
| 1.823 | B.118 | C.5 |
| 1.824 | B.119 | C.5 |
| 1.825 | B.120 | C.5 |
| 1.826 | B.121 | C.5 |
| 1.827 | B.122 | C.5 |
| 1.828 | B.123 | C.5 |
| 1.829 | B.124 | C.5 |
| 1.830 | B.125 | C.5 |
| 1.831 | B.126 | C.5 |
| 1.832 | B.127 | C.5 |
| 1.833 | B.128 | C.5 |
| 1.834 | B.129 | C.5 |
| 1.835 | B.130 | C.5 |
| 1.836 | B.131 | C.5 |
| 1.837 | B.132 | C.5 |
| 1.838 | B.133 | C.5 |
| 1.839 | B.134 | C.5 |
| 1.840 | B.135 | C.5 |
| 1.841 | B.136 | C.5 |
| 1.842 | B.137 | C.5 |
| 1.843 | B.138 | C.5 |
| 1.844 | B.139 | C.5 |
| 1.845 | B.140 | C.5 |
| 1.846 | B.141 | C.5 |
| 1.847 | B.1 | C.6 |
| 1.848 | B.2 | C.6 |
| 1.849 | B.3 | C.6 |
| 1.850 | B.4 | C.6 |
| 1.851 | B.5 | C.6 |
| 1.852 | B.6 | C.6 |
| 1.853 | B.7 | C.6 |
| 1.854 | B.8 | C.6 |
| 1.855 | B.9 | C.6 |
| 1.856 | B.10 | C.6 |
| 1.857 | B.11 | C.6 |
| 1.858 | B.12 | C.6 |
| 1.859 | B.13 | C.6 |
| 1.860 | B.14 | C.6 |
| 1.861 | B.15 | C.6 |
| 1.862 | B.16 | C.6 |
| 1.863 | B.17 | C.6 |
| 1.864 | B.18 | C.6 |
| 1.865 | B.19 | C.6 |
| 1.866 | B.20 | C.6 |
| 1.867 | B.21 | C.6 |
| 1.868 | B.22 | C.6 |
| 1.869 | B.23 | C.6 |
| 1.870 | B.24 | C.6 |
| 1.871 | B.25 | C.6 |
| 1.872 | B.26 | C.6 |
| 1.873 | B.27 | C.6 |
| 1.874 | B.28 | C.6 |
| 1.875 | B.29 | C.6 |
| 1.876 | B.30 | C.6 |
| 1.877 | B.31 | C.6 |
| 1.878 | B.32 | C.6 |
| 1.879 | B.33 | C.6 |
| 1.880 | B.34 | C.6 |
| 1.881 | B.35 | C.6 |
| 1.882 | B.36 | C.6 |
| 1.883 | B.37 | C.6 |
| 1.884 | B.38 | C.6 |
| 1.885 | B.39 | C.6 |
| 1.886 | B.40 | C.6 |
| 1.887 | B.41 | C.6 |
| 1.888 | B.42 | C.6 |
| 1.889 | B.43 | C.6 |
| 1.890 | B.44 | C.6 |
| 1.891 | B.45 | C.6 |
| 1.892 | B.46 | C.6 |
| 1.893 | B.47 | C.6 |
| 1.894 | B.48 | C.6 |
| 1.895 | B.49 | C.6 |
| 1.896 | B.50 | C.6 |
| 1.897 | B.51 | C.6 |
| 1.898 | B.52 | C.6 |
| 1.899 | B.53 | C.6 |
| 1.900 | B.54 | C.6 |
| 1.901 | B.55 | C.6 |
| 1.902 | B.56 | C.6 |
| 1.903 | B.57 | C.6 |
| 1.904 | B.58. | C.6 |
| 1.905 | B.59 | C.6 |
| 1.906 | B.60 | C.6 |
| 1.907 | B.61 | C.6 |
| 1.908 | B.62 | C.6 |
| 1.909 | B.63 | C.6 |
| 1.910 | B.64 | C.6 |
| 1.911 | B.65 | C.6 |
| 1.912 | B.66 | C.6 |
| 1.913 | B.67 | C.6 |
| 1.914 | B.68 | C.6 |
| 1.915 | B.69 | C.6 |
| 1.916 | B.70 | C.6 |
| 1.917 | B.71 | C.6 |
| 1.918 | B.72 | C.6 |
| 1.919 | B.73 | C.6 |
| 1.920 | B.74 | C.6 |
| 1.921 | B.75 | C.6 |
| 1.922 | B.76 | C.6 |
| 1.923 | B.77 | C.6 |
| 1.924 | B.78 | C.6 |
| 1.925 | B.79 | C.6 |
| 1.926 | B.80 | C.6 |
| 1.927 | B.81 | C.6 |
| 1.928 | B.82 | C.6 |
| 1.929 | B.83 | C.6 |
| 1.930 | B.84 | C.6 |
| 1.931 | B.85 | C.6 |
| 1.932 | B.86 | C.6 |
| 1.933 | B.87 | C.6 |
| 1.934 | B.88 | C.6 |
| 1.935 | B.89 | C.6 |
| 1.936 | B.90 | C.6 |
| 1.937 | B.91 | C.6 |
| 1.938 | B.92 | C.6 |
| 1.939 | B.93 | C.6 |
| 1.940 | B.94 | C.6 |
| 1.941 | B.95 | C.6 |
| 1.942 | B.96 | C.6 |
| 1.943 | B.97 | C.6 |

TABLE 1-continued (herbicidal combinations 1.1 to 1.1833):

| comp. no. | herbicide B | safener C |
|---|---|---|
| 1.944 | B.98 | C.6 |
| 1.945 | B.99 | C.6 |
| 1.946 | B.100 | C.6 |
| 1.947 | B.101 | C.6 |
| 1.948 | B.102 | C.6 |
| 1.949 | B.103 | C.6 |
| 1.950 | B.104 | C.6 |
| 1.951 | B.105 | C.6 |
| 1.952 | B.106 | C.6 |
| 1.953 | B.107 | C.6 |
| 1.954 | B.108 | C.6 |
| 1.955 | B.109 | C.6 |
| 1.956 | B.110 | C.6 |
| 1.957 | B.111 | C.6 |
| 1.958 | B.112 | C.6 |
| 1.959 | B.113 | C.6 |
| 1.960 | B.114 | C.6 |
| 1.961 | B.115 | C.6 |
| 1.962 | B.116 | C.6 |
| 1.963 | B.117 | C.6 |
| 1.964 | B.118 | C.6 |
| 1.965 | B.119 | C.6 |
| 1.966 | B.120 | C.6 |
| 1.967 | B.121 | C.6 |
| 1.968 | B.122 | C.6 |
| 1.969 | B.123 | C.6 |
| 1.970 | B.124 | C.6 |
| 1.971 | B.125 | C.6 |
| 1.972 | B.126 | C.6 |
| 1.973 | B.127 | C.6 |
| 1.974 | B.128 | C.6 |
| 1.975 | B.129 | C.6 |
| 1.976 | B.130 | C.6 |
| 1.977 | B.131 | C.6 |
| 1.978 | B.132 | C.6 |
| 1.979 | B.133 | C.6 |
| 1.980 | B.134 | C.6 |
| 1.981 | B.135 | C.6 |
| 1.982 | B.136 | C.6 |
| 1.983 | B.137 | C.6 |
| 1.984 | B.138 | C.6 |
| 1.985 | B.139 | C.6 |
| 1.986 | B.140 | C.6 |
| 1.987 | B.141 | C.6 |
| 1.988 | B.1 | C.7 |
| 1.989 | B.2 | C.7 |
| 1.990 | B.3 | C.7 |
| 1.991 | B.4 | C.7 |
| 1.992 | B.5 | C.7 |
| 1.993 | B.6 | C.7 |
| 1.994 | B.7 | C.7 |
| 1.995 | B.8 | C.7 |
| 1.996 | B.9 | C.7 |
| 1.997 | B.10 | C.7 |
| 1.998 | B.11 | C.7 |
| 1.999 | B.12 | C.7 |
| 1.1000 | B.13 | C.7 |
| 1.1001 | B.14 | C.7 |
| 1.1002 | B.15 | C.7 |
| 1.1003 | B.16 | C.7 |
| 1.1004 | B.17 | C.7 |
| 1.1005 | B.18 | C.7 |
| 1.1006 | B.19 | C.7 |
| 1.1007 | B.20 | C.7 |
| 1.1008 | B.21 | C.7 |
| 1.1009 | B.22 | C.7 |
| 1.1010 | B.23 | C.7 |
| 1.1011 | B.24 | C.7 |
| 1.1012 | B.25 | C.7 |
| 1.1013 | B.26 | C.7 |
| 1.1014 | B.27 | C.7 |
| 1.1015 | B.28 | C.7 |
| 1.1016 | B.29 | C.7 |
| 1.1017 | B.30 | C.7 |
| 1.1018 | B.31 | C.7 |
| 1.1019 | B.32 | C.7 |
| 1.1020 | B.33 | C.7 |
| 1.1021 | B.34 | C.7 |
| 1.1022 | B.35 | C.7 |
| 1.1023 | B.36 | C.7 |
| 1.1024 | B.37 | C.7 |
| 1.1025 | B.38 | C.7 |
| 1.1026 | B.39 | C.7 |
| 1.1027 | B.40 | C.7 |
| 1.1028 | B.41 | C.7 |
| 1.1029 | B.42 | C.7 |
| 1.1030 | B.43 | C.7 |
| 1.1031 | B.44 | C.7 |
| 1.1032 | B.45 | C.7 |
| 1.1033 | B.46 | C.7 |
| 1.1034 | B.47 | C.7 |
| 1.1035 | B.48 | C.7 |
| 1.1036 | B.49 | C.7 |
| 1.1037 | B.50 | C.7 |
| 1.1038 | B.51 | C.7 |
| 1.1039 | B.52 | C.7 |
| 1.1040 | B.53 | C.7 |
| 1.1041 | B.54 | C.7 |
| 1.1042 | B.55 | C.7 |
| 1.1043 | B.56 | C.7 |
| 1.1044 | B.57 | C.7 |
| 1.1045 | B.58. | C.7 |
| 1.1046 | B.59 | C.7 |
| 1.1047 | B.60 | C.7 |
| 1.1048 | B.61 | C.7 |
| 1.1049 | B.62 | C.7 |
| 1.1050 | B.63 | C.7 |
| 1.1051 | B.64 | C.7 |
| 1.1052 | B.65 | C.7 |
| 1.1053 | B.66 | C.7 |
| 1.1054 | B.67 | C.7 |
| 1.1055 | B.68 | C.7 |
| 1.1056 | B.69 | C.7 |
| 1.1057 | B.70 | C.7 |
| 1.1058 | B.71 | C.7 |
| 1.1059 | B.72 | C.7 |
| 1.1060 | B.73 | C.7 |
| 1.1061 | B.74 | C.7 |
| 1.1062 | B.75 | C.7 |
| 1.1063 | B.76 | C.7 |
| 1.1064 | B.77 | C.7 |
| 1.1065 | B.78 | C.7 |
| 1.1066 | B.79 | C.7 |
| 1.1067 | B.80 | C.7 |
| 1.1068 | B.81 | C.7 |
| 1.1069 | B.82 | C.7 |
| 1.1070 | B.83 | C.7 |
| 1.1071 | B.84 | C.7 |
| 1.1072 | B.85 | C.7 |
| 1.1073 | B.86 | C.7 |
| 1.1074 | B.87 | C.7 |
| 1.1075 | B.88 | C.7 |
| 1.1076 | B.89 | C.7 |
| 1.1077 | B.90 | C.7 |
| 1.1078 | B.91 | C.7 |
| 1.1079 | B.92 | C.7 |
| 1.1080 | B.93 | C.7 |
| 1.1081 | B.94 | C.7 |
| 1.1082 | B.95 | C.7 |
| 1.1083 | B.96 | C.7 |
| 1.1084 | B.97 | C.7 |
| 1.1085 | B.98 | C.7 |
| 1.1086 | B.99 | C.7 |
| 1.1087 | B.100 | C.7 |
| 1.1088 | B.101 | C.7 |
| 1.1089 | B.102 | C.7 |
| 1.1090 | B.103 | C.7 |
| 1.1091 | B.104 | C.7 |
| 1.1092 | B.105 | C.7 |
| 1.1093 | B.106 | C.7 |

TABLE 1-continued (herbicidal combinations 1.1 to 1.1833):

| comp. no. | herbicide B | safener C |
|---|---|---|
| 1.1094 | B.107 | C.7 |
| 1.1095 | B.108 | C.7 |
| 1.1096 | B.109 | C.7 |
| 1.1097 | B.110 | C.7 |
| 1.1098 | B.111 | C.7 |
| 1.1099 | B.112 | C.7 |
| 1.1100 | B.113 | C.7 |
| 1.1101 | B.114 | C.7 |
| 1.1102 | B.115 | C.7 |
| 1.1103 | B.116 | C.7 |
| 1.1104 | B.117 | C.7 |
| 1.1105 | B.118 | C.7 |
| 1.1106 | B.119 | C.7 |
| 1.1107 | B.120 | C.7 |
| 1.1108 | B.121 | C.7 |
| 1.1109 | B.122 | C.7 |
| 1.1110 | B.123 | C.7 |
| 1.1111 | B.124 | C.7 |
| 1.1112 | B.125 | C.7 |
| 1.1113 | B.126 | C.7 |
| 1.1114 | B.127 | C.7 |
| 1.1115 | B.128 | C.7 |
| 1.1116 | B.129 | C.7 |
| 1.1117 | B.130 | C.7 |
| 1.1118 | B.131 | C.7 |
| 1.1119 | B.132 | C.7 |
| 1.1120 | B.133 | C.7 |
| 1.1121 | B.134 | C.7 |
| 1.1122 | B.135 | C.7 |
| 1.1123 | B.136 | C.7 |
| 1.1124 | B.137 | C.7 |
| 1.1125 | B.138 | C.7 |
| 1.1126 | B.139 | C.7 |
| 1.1127 | B.140 | C.7 |
| 1.1128 | B.141 | C.7 |
| 1.1129 | B.1 | C.8 |
| 1.1130 | B.2 | C.8 |
| 1.1131 | B.3 | C.8 |
| 1.1132 | B.4 | C.8 |
| 1.1133 | B.5 | C.8 |
| 1.1134 | B.6 | C.8 |
| 1.1135 | B.7 | C.8 |
| 1.1136 | B.8 | C.8 |
| 1.1137 | B.9 | C.8 |
| 1.1138 | B.10 | C.8 |
| 1.1139 | B.11 | C.8 |
| 1.1140 | B.12 | C.8 |
| 1.1141 | B.13 | C.8 |
| 1.1142 | B.14 | C.8 |
| 1.1143 | B.15 | C.8 |
| 1.1144 | B.16 | C.8 |
| 1.1145 | B.17 | C.8 |
| 1.1146 | B.18 | C.8 |
| 1.1147 | B.19 | C.8 |
| 1.1148 | B.20 | C.8 |
| 1.1149 | B.21 | C.8 |
| 1.1150 | B.22 | C.8 |
| 1.1151 | B.23 | C.8 |
| 1.1152 | B.24 | C.8 |
| 1.1153 | B.25 | C.8 |
| 1.1154 | B.26 | C.8 |
| 1.1155 | B.27 | C.8 |
| 1.1156 | B.28 | C.8 |
| 1.1157 | B.29 | C.8 |
| 1.1158 | B.30 | C.8 |
| 1.1159 | B.31 | C.8 |
| 1.1160 | B.32 | C.8 |
| 1.1161 | B.33 | C.8 |
| 1.1162 | B.34 | C.8 |
| 1.1163 | B.35 | C.8 |
| 1.1164 | B.36 | C.8 |
| 1.1165 | B.37 | C.8 |
| 1.1166 | B.38 | C.8 |
| 1.1167 | B.39 | C.8 |
| 1.1168 | B.40 | C.8 |
| 1.1169 | B.41 | C.8 |
| 1.1170 | B.42 | C.8 |
| 1.1171 | B.43 | C.8 |
| 1.1172 | B.44 | C.8 |
| 1.1173 | B.45 | C.8 |
| 1.1174 | B.46 | C.8 |
| 1.1175 | B.47 | C.8 |
| 1.1176 | B.48 | C.8 |
| 1.1177 | B.49 | C.8 |
| 1.1178 | B.50 | C.8 |
| 1.1179 | B.51 | C.8 |
| 1.1180 | B.52 | C.8 |
| 1.1181 | B.53 | C.8 |
| 1.1182 | B.54 | C.8 |
| 1.1183 | B.55 | C.8 |
| 1.1184 | B.56 | C.8 |
| 1.1185 | B.57 | C.8 |
| 1.1186 | B.58. | C.8 |
| 1.1187 | B.59 | C.8 |
| 1.1188 | B.60 | C.8 |
| 1.1189 | B.61 | C.8 |
| 1.1190 | B.62 | C.8 |
| 1.1191 | B.63 | C.8 |
| 1.1192 | B.64 | C.8 |
| 1.1193 | B.65 | C.8 |
| 1.1194 | B.66 | C.8 |
| 1.1195 | B.67 | C.8 |
| 1.1196 | B.68 | C.8 |
| 1.1197 | B.69 | C.8 |
| 1.1198 | B.70 | C.8 |
| 1.1199 | B.71 | C.8 |
| 1.1200 | B.72 | C.8 |
| 1.1201 | B.73 | C.8 |
| 1.1202 | B.74 | C.8 |
| 1.1203 | B.75 | C.8 |
| 1.1204 | B.76 | C.8 |
| 1.1205 | B.77 | C.8 |
| 1.1206 | B.78 | C.8 |
| 1.1207 | B.79 | C.8 |
| 1.1208 | B.80 | C.8 |
| 1.1209 | B.81 | C.8 |
| 1.1210 | B.82 | C.8 |
| 1.1211 | B.83 | C.8 |
| 1.1212 | B.84 | C.8 |
| 1.1213 | B.85 | C.8 |
| 1.1214 | B.86 | C.8 |
| 1.1215 | B.87 | C.8 |
| 1.1216 | B.88 | C.8 |
| 1.1217 | B.89 | C.8 |
| 1.1218 | B.90 | C.8 |
| 1.1219 | B.91 | C.8 |
| 1.1220 | B.92 | C.8 |
| 1.1221 | B.93 | C.8 |
| 1.1222 | B.94 | C.8 |
| 1.1223 | B.95 | C.8 |
| 1.1224 | B.96 | C.8 |
| 1.1225 | B.97 | C.8 |
| 1.1226 | B.98 | C.8 |
| 1.1227 | B.99 | C.8 |
| 1.1228 | B.100 | C.8 |
| 1.1229 | B.101 | C.8 |
| 1.1230 | B.102 | C.8 |
| 1.1231 | B.103 | C.8 |
| 1.1232 | B.104 | C.8 |
| 1.1233 | B.105 | C.8 |
| 1.1234 | B.106 | C.8 |
| 1.1235 | B.107 | C.8 |
| 1.1236 | B.108 | C.8 |
| 1.1237 | B.109 | C.8 |
| 1.1238 | B.110 | C.8 |
| 1.1239 | B.111 | C.8 |
| 1.1240 | B.112 | C.8 |
| 1.1241 | B.113 | C.8 |
| 1.1242 | B.114 | C.8 |
| 1.1243 | B.115 | C.8 |

TABLE 1-continued (herbicidal combinations 1.1 to 1.1833):

| comp. no. | herbicide B | safener C |
|---|---|---|
| 1.1244 | B.116 | C.8 |
| 1.1245 | B.117 | C.8 |
| 1.1246 | B.118 | C.8 |
| 1.1247 | B.119 | C.8 |
| 1.1248 | B.120 | C.8 |
| 1.1249 | B.121 | C.8 |
| 1.1250 | B.122 | C.8 |
| 1.1251 | B.123 | C.8 |
| 1.1252 | B.124 | C.8 |
| 1.1253 | B.125 | C.8 |
| 1.1254 | B.126 | C.8 |
| 1.1255 | B.127 | C.8 |
| 1.1256 | B.128 | C.8 |
| 1.1257 | B.129 | C.8 |
| 1.1258 | B.130 | C.8 |
| 1.1259 | B.131 | C.8 |
| 1.1260 | B.132 | C.8 |
| 1.1261 | B.133 | C.8 |
| 1.1262 | B.134 | C.8 |
| 1.1263 | B.135 | C.8 |
| 1.1264 | B.136 | C.8 |
| 1.1265 | B.137 | C.8 |
| 1.1266 | B.138 | C.8 |
| 1.1267 | B.139 | C.8 |
| 1.1268 | B.140 | C.8 |
| 1.1269 | B.141 | C.8 |
| 1.1270 | B.1 | C.9 |
| 1.1271 | B.2 | C.9 |
| 1.1272 | B.3 | C.9 |
| 1.1273 | B.4 | C.9 |
| 1.1274 | B.5 | C.9 |
| 1.1275 | B.6 | C.9 |
| 1.1276 | B.7 | C.9 |
| 1.1277 | B.8 | C.9 |
| 1.1278 | B.9 | C.9 |
| 1.1279 | B.10 | C.9 |
| 1.1280 | B.11 | C.9 |
| 1.1281 | B.12 | C.9 |
| 1.1282 | B.13 | C.9 |
| 1.1283 | B.14 | C.9 |
| 1.1284 | B.15 | C.9 |
| 1.1285 | B.16 | C.9 |
| 1.1286 | B.17 | C.9 |
| 1.1287 | B.18 | C.9 |
| 1.1288 | B.19 | C.9 |
| 1.1289 | B.20 | C.9 |
| 1.1290 | B.21 | C.9 |
| 1.1291 | B.22 | C.9 |
| 1.1292 | B.23 | C.9 |
| 1.1293 | B.24 | C.9 |
| 1.1294 | B.25 | C.9 |
| 1.1295 | B.26 | C.9 |
| 1.1296 | B.27 | C.9 |
| 1.1297 | B.28 | C.9 |
| 1.1298 | B.29 | C.9 |
| 1.1299 | B.30 | C.9 |
| 1.1300 | B.31 | C.9 |
| 1.1301 | B.32 | C.9 |
| 1.1302 | B.33 | C.9 |
| 1.1303 | B.34 | C.9 |
| 1.1304 | B.35 | C.9 |
| 1.1305 | B.36 | C.9 |
| 1.1306 | B.37 | C.9 |
| 1.1307 | B.38 | C.9 |
| 1.1308 | B.39 | C.9 |
| 1.1309 | B.40 | C.9 |
| 1.1310 | B.41 | C.9 |
| 1.1311 | B.42 | C.9 |
| 1.1312 | B.43 | C.9 |
| 1.1313 | B.44 | C.9 |
| 1.1314 | B.45 | C.9 |
| 1.1315 | B.46 | C.9 |
| 1.1316 | B.47 | C.9 |
| 1.1317 | B.48 | C.9 |
| 1.1318 | B.49 | C.9 |
| 1.1319 | B.50 | C.9 |
| 1.1320 | B.51 | C.9 |
| 1.1321 | B.52 | C.9 |
| 1.1322 | B.53 | C.9 |
| 1.1323 | B.54 | C.9 |
| 1.1324 | B.55 | C.9 |
| 1.1325 | B.56 | C.9 |
| 1.1326 | B.57 | C.9 |
| 1.1327 | B.58. | C.9 |
| 1.1328 | B.59 | C.9 |
| 1.1329 | B.60 | C.9 |
| 1.1330 | B.61 | C.9 |
| 1.1331 | B.62 | C.9 |
| 1.1332 | B.63 | C.9 |
| 1.1333 | B.64 | C.9 |
| 1.1334 | B.65 | C.9 |
| 1.1335 | B.66 | C.9 |
| 1.1336 | B.67 | C.9 |
| 1.1337 | B.68 | C.9 |
| 1.1338 | B.69 | C.9 |
| 1.1339 | B.70 | C.9 |
| 1.1340 | B.71 | C.9 |
| 1.1341 | B.72 | C.9 |
| 1.1342 | B.73 | C.9 |
| 1.1343 | B.74 | C.9 |
| 1.1344 | B.75 | C.9 |
| 1.1345 | B.76 | C.9 |
| 1.1346 | B.77 | C.9 |
| 1.1347 | B.78 | C.9 |
| 1.1348 | B.79 | C.9 |
| 1.1349 | B.80 | C.9 |
| 1.1350 | B.81 | C.9 |
| 1.1351 | B.82 | C.9 |
| 1.1352 | B.83 | C.9 |
| 1.1353 | B.84 | C.9 |
| 1.1354 | B.85 | C.9 |
| 1.1355 | B.86 | C.9 |
| 1.1356 | B.87 | C.9 |
| 1.1357 | B.88 | C.9 |
| 1.1358 | B.89 | C.9 |
| 1.1359 | B.90 | C.9 |
| 1.1360 | B.91 | C.9 |
| 1.1361 | B.92 | C.9 |
| 1.1362 | B.93 | C.9 |
| 1.1363 | B.94 | C.9 |
| 1.1364 | B.95 | C.9 |
| 1.1365 | B.96 | C.9 |
| 1.1366 | B.97 | C.9 |
| 1.1367 | B.98 | C.9 |
| 1.1368 | B.99 | C.9 |
| 1.1369 | B.100 | C.9 |
| 1.1370 | B.101 | C.9 |
| 1.1371 | B.102 | C.9 |
| 1.1372 | B.103 | C.9 |
| 1.1373 | B.104 | C.9 |
| 1.1374 | B.105 | C.9 |
| 1.1375 | B.106 | C.9 |
| 1.1376 | B.107 | C.9 |
| 1.1377 | B.108 | C.9 |
| 1.1378 | B.109 | C.9 |
| 1.1379 | B.110 | C.9 |
| 1.1380 | B.111 | C.9 |
| 1.1381 | B.112 | C.9 |
| 1.1382 | B.113 | C.9 |
| 1.1383 | B.114 | C.9 |
| 1.1384 | B.115 | C.9 |
| 1.1385 | B.116 | C.9 |
| 1.1386 | B.117 | C.9 |
| 1.1387 | B.118 | C.9 |
| 1.1388 | B.119 | C.9 |
| 1.1389 | B.120 | C.9 |
| 1.1390 | B.121 | C.9 |
| 1.1391 | B.122 | C.9 |
| 1.1392 | B.123 | C.9 |
| 1.1393 | B.124 | C.9 |

TABLE 1-continued (herbicidal combinations 1.1 to 1.1833):

| comp. no. | herbicide B | safener C |
|---|---|---|
| 1.1394 | B.125 | C.9 |
| 1.1395 | B.126 | C.9 |
| 1.1396 | B.127 | C.9 |
| 1.1397 | B.128 | C.9 |
| 1.1398 | B.129 | C.9 |
| 1.1399 | B.130 | C.9 |
| 1.1400 | B.131 | C.9 |
| 1.1401 | B.132 | C.9 |
| 1.1402 | B.133 | C.9 |
| 1.1403 | B.134 | C.9 |
| 1.1404 | B.135 | C.9 |
| 1.1405 | B.136 | C.9 |
| 1.1406 | B.137 | C.9 |
| 1.1407 | B.138 | C.9 |
| 1.1408 | B.139 | C.9 |
| 1.1409 | B.140 | C.9 |
| 1.1410 | B.141 | C.9 |
| 1.1411 | B.1 | C.10 |
| 1.1412 | B.2 | C.10 |
| 1.1413 | B.3 | C.10 |
| 1.1414 | B.4 | C.10 |
| 1.1415 | B.5 | C.10 |
| 1.1416 | B.6 | C.10 |
| 1.1417 | B.7 | C.10 |
| 1.1418 | B.8 | C.10 |
| 1.1419 | B.9 | C.10 |
| 1.1420 | B.10 | C.10 |
| 1.1421 | B.11 | C.10 |
| 1.1422 | B.12 | C.10 |
| 1.1423 | B.13 | C.10 |
| 1.1424 | B.14 | C.10 |
| 1.1425 | B.15 | C.10 |
| 1.1426 | B.16 | C.10 |
| 1.1427 | B.17 | C.10 |
| 1.1428 | B.18 | C.10 |
| 1.1429 | B.19 | C.10 |
| 1.1430 | B.20 | C.10 |
| 1.1431 | B.21 | C.10 |
| 1.1432 | B.22 | C.10 |
| 1.1433 | B.23 | C.10 |
| 1.1434 | B.24 | C.10 |
| 1.1435 | B.25 | C.10 |
| 1.1436 | B.26 | C.10 |
| 1.1437 | B.27 | C.10 |
| 1.1438 | B.28 | C.10 |
| 1.1439 | B.29 | C.10 |
| 1.1440 | B.30 | C.10 |
| 1.1441 | B.31 | C.10 |
| 1.1442 | B.32 | C.10 |
| 1.1443 | B.33 | C.10 |
| 1.1444 | B.34 | C.10 |
| 1.1445 | B.35 | C.10 |
| 1.1446 | B.36 | C.10 |
| 1.1447 | B.37 | C.10 |
| 1.1448 | B.38 | C.10 |
| 1.1449 | B.39 | C.10 |
| 1.1450 | B.40 | C.10 |
| 1.1451 | B.41 | C.10 |
| 1.1452 | B.42 | C.10 |
| 1.1453 | B.43 | C.10 |
| 1.1454 | B.44 | C.10 |
| 1.1455 | B.45 | C.10 |
| 1.1456 | B.46 | C.10 |
| 1.1457 | B.47 | C.10 |
| 1.1458 | B.48 | C.10 |
| 1.1459 | B.49 | C.10 |
| 1.1460 | B.50 | C.10 |
| 1.1461 | B.51 | C.10 |
| 1.1462 | B.52 | C.10 |
| 1.1463 | B.53 | C.10 |
| 1.1464 | B.54 | C.10 |
| 1.1465 | B.55 | C.10 |
| 1.1466 | B.56 | C.10 |
| 1.1467 | B.57 | C.10 |
| 1.1468 | B.58. | C.10 |
| 1.1469 | B.59 | C.10 |
| 1.1470 | B.60 | C.10 |
| 1.1471 | B.61 | C.10 |
| 1.1472 | B.62 | C.10 |
| 1.1473 | B.63 | C.10 |
| 1.1474 | B.64 | C.10 |
| 1.1475 | B.65 | C.10 |
| 1.1476 | B.66 | C.10 |
| 1.1477 | B.67 | C.10 |
| 1.1478 | B.68 | C.10 |
| 1.1479 | B.69 | C.10 |
| 1.1480 | B.70 | C.10 |
| 1.1481 | B.71 | C.10 |
| 1.1482 | B.72 | C.10 |
| 1.1483 | B.73 | C.10 |
| 1.1484 | B.74 | C.10 |
| 1.1485 | B.75 | C.10 |
| 1.1486 | B.76 | C.10 |
| 1.1487 | B.77 | C.10 |
| 1.1488 | B.78 | C.10 |
| 1.1489 | B.79 | C.10 |
| 1.1490 | B.80 | C.10 |
| 1.1491 | B.81 | C.10 |
| 1.1492 | B.82 | C.10 |
| 1.1493 | B.83 | C.10 |
| 1.1494 | B.84 | C.10 |
| 1.1495 | B.85 | C.10 |
| 1.1496 | B.86 | C.10 |
| 1.1497 | B.87 | C.10 |
| 1.1498 | B.88 | C.10 |
| 1.1499 | B.89 | C.10 |
| 1.1500 | B.90 | C.10 |
| 1.1501 | B.91 | C.10 |
| 1.1502 | B.92 | C.10 |
| 1.1503 | B.93 | C.10 |
| 1.1504 | B.94 | C.10 |
| 1.1505 | B.95 | C.10 |
| 1.1506 | B.96 | C.10 |
| 1.1507 | B.97 | C.10 |
| 1.1508 | B.98 | C.10 |
| 1.1509 | B.99 | C.10 |
| 1.1510 | B.100 | C.10 |
| 1.1511 | B.101 | C.10 |
| 1.1512 | B.102 | C.10 |
| 1.1513 | B.103 | C.10 |
| 1.1514 | B.104 | C.10 |
| 1.1515 | B.105 | C.10 |
| 1.1516 | B.106 | C.10 |
| 1.1517 | B.107 | C.10 |
| 1.1518 | B.108 | C.10 |
| 1.1519 | B.109 | C.10 |
| 1.1520 | B.110 | C.10 |
| 1.1521 | B.111 | C.10 |
| 1.1522 | B.112 | C.10 |
| 1.1523 | B.113 | C.10 |
| 1.1524 | B.114 | C.10 |
| 1.1525 | B.115 | C.10 |
| 1.1526 | B.116 | C.10 |
| 1.1527 | B.117 | C.10 |
| 1.1528 | B.118 | C.10 |
| 1.1529 | B.119 | C.10 |
| 1.1530 | B.120 | C.10 |
| 1.1531 | B.121 | C.10 |
| 1.1532 | B.122 | C.10 |
| 1.1533 | B.123 | C.10 |
| 1.1534 | B.124 | C.10 |
| 1.1535 | B.125 | C.10 |
| 1.1536 | B.126 | C.10 |
| 1.1537 | B.127 | C.10 |
| 1.1538 | B.128 | C.10 |
| 1.1539 | B.129 | C.10 |
| 1.1540 | B.130 | C.10 |
| 1.1541 | B.131 | C.10 |
| 1.1542 | B.132 | C.10 |
| 1.1543 | B.133 | C.10 |

TABLE 1-continued (herbicidal combinations 1.1 to 1.1833):

| comp. no. | herbicide B | safener C |
|---|---|---|
| 1.1544 | B.134 | C.10 |
| 1.1545 | B.135 | C.10 |
| 1.1546 | B.136 | C.10 |
| 1.1547 | B.137 | C.10 |
| 1.1548 | B.138 | C.10 |
| 1.1549 | B.139 | C.10 |
| 1.1550 | B.140 | C.10 |
| 1.1551 | B.141 | C.10 |
| 1.1552 | B.1 | C.11 |
| 1.1553 | B.2 | C.11 |
| 1.1554 | B.3 | C.11 |
| 1.1555 | B.4 | C.11 |
| 1.1556 | B.5 | C.11 |
| 1.1557 | B.6 | C.11 |
| 1.1558 | B.7 | C.11 |
| 1.1559 | B.8 | C.11 |
| 1.1560 | B.9 | C.11 |
| 1.1561 | B.10 | C.11 |
| 1.1562 | B.11 | C.11 |
| 1.1563 | B.12 | C.11 |
| 1.1564 | B.13 | C.11 |
| 1.1565 | B.14 | C.11 |
| 1.1566 | B.15 | C.11 |
| 1.1567 | B.16 | C.11 |
| 1.1568 | B.17 | C.11 |
| 1.1569 | B.18 | C.11 |
| 1.1570 | B.19 | C.11 |
| 1.1571 | B.20 | C.11 |
| 1.1572 | B.21 | C.11 |
| 1.1573 | B.22 | C.11 |
| 1.1574 | B.23 | C.11 |
| 1.1575 | B.24 | C.11 |
| 1.1576 | B.25 | C.11 |
| 1.1577 | B.26 | C.11 |
| 1.1578 | B.27 | C.11 |
| 1.1579 | B.28 | C.11 |
| 1.1580 | B.29 | C.11 |
| 1.1581 | B.30 | C.11 |
| 1.1582 | B.31 | C.11 |
| 1.1583 | B.32 | C.11 |
| 1.1584 | B.33 | C.11 |
| 1.1585 | B.34 | C.11 |
| 1.1586 | B.35 | C.11 |
| 1.1587 | B.36 | C.11 |
| 1.1588 | B.37 | C.11 |
| 1.1589 | B.38 | C.11 |
| 1.1590 | B.39 | C.11 |
| 1.1591 | B.40 | C.11 |
| 1.1592 | B.41 | C.11 |
| 1.1593 | B.42 | C.11 |
| 1.1594 | B.43 | C.11 |
| 1.1595 | B.44 | C.11 |
| 1.1596 | B.45 | C.11 |
| 1.1597 | B.46 | C.11 |
| 1.1598 | B.47 | C.11 |
| 1.1599 | B.48 | C.11 |
| 1.1600 | B.49 | C.11 |
| 1.1601 | B.50 | C.11 |
| 1.1602 | B.51 | C.11 |
| 1.1603 | B.52 | C.11 |
| 1.1604 | B.53 | C.11 |
| 1.1605 | B.54 | C.11 |
| 1.1606 | B.55 | C.11 |
| 1.1607 | B.56 | C.11 |
| 1.1608 | B.57 | C.11 |
| 1.1609 | B.58. | C.11 |
| 1.1610 | B.59 | C.11 |
| 1.1611 | B.60 | C.11 |
| 1.1612 | B.61 | C.11 |
| 1.1613 | B.62 | C.11 |
| 1.1614 | B.63 | C.11 |
| 1.1615 | B.64 | C.11 |
| 1.1616 | B.65 | C.11 |
| 1.1617 | B.66 | C.11 |
| 1.1618 | B.67 | C.11 |
| 1.1619 | B.68 | C.11 |
| 1.1620 | B.69 | C.11 |
| 1.1621 | B.70 | C.11 |
| 1.1622 | B.71 | C.11 |
| 1.1623 | B.72 | C.11 |
| 1.1624 | B.73 | C.11 |
| 1.1625 | B.74 | C.11 |
| 1.1626 | B.75 | C.11 |
| 1.1627 | B.76 | C.11 |
| 1.1628 | B.77 | C.11 |
| 1.1629 | B.78 | C.11 |
| 1.1630 | B.79 | C.11 |
| 1.1631 | B.80 | C.11 |
| 1.1632 | B.81 | C.11 |
| 1.1633 | B.82 | C.11 |
| 1.1634 | B.83 | C.11 |
| 1.1635 | B.84 | C.11 |
| 1.1636 | B.85 | C.11 |
| 1.1637 | B.86 | C.11 |
| 1.1638 | B.87 | C.11 |
| 1.1639 | B.88 | C.11 |
| 1.1640 | B.89 | C.11 |
| 1.1641 | B.90 | C.11 |
| 1.1642 | B.91 | C.11 |
| 1.1643 | B.92 | C.11 |
| 1.1644 | B.93 | C.11 |
| 1.1645 | B.94 | C.11 |
| 1.1646 | B.95 | C.11 |
| 1.1647 | B.96 | C.11 |
| 1.1648 | B.97 | C.11 |
| 1.1649 | B.98 | C.11 |
| 1.1650 | B.99 | C.11 |
| 1.1651 | B.100 | C.11 |
| 1.1652 | B.101 | C.11 |
| 1.1653 | B.102 | C.11 |
| 1.1654 | B.103 | C.11 |
| 1.1655 | B.104 | C.11 |
| 1.1656 | B.105 | C.11 |
| 1.1657 | B.106 | C.11 |
| 1.1658 | B.107 | C.11 |
| 1.1659 | B.108 | C.11 |
| 1.1660 | B.109 | C.11 |
| 1.1661 | B.110 | C.11 |
| 1.1662 | B.111 | C.11 |
| 1.1663 | B.112 | C.11 |
| 1.1664 | B.113 | C.11 |
| 1.1665 | B.114 | C.11 |
| 1.1666 | B.115 | C.11 |
| 1.1667 | B.116 | C.11 |
| 1.1668 | B.117 | C.11 |
| 1.1669 | B.118 | C.11 |
| 1.1670 | B.119 | C.11 |
| 1.1671 | B.120 | C.11 |
| 1.1672 | B.121 | C.11 |
| 1.1673 | B.122 | C.11 |
| 1.1674 | B.123 | C.11 |
| 1.1675 | B.124 | C.11 |
| 1.1676 | B.125 | C.11 |
| 1.1677 | B.126 | C.11 |
| 1.1678 | B.127 | C.11 |
| 1.1679 | B.128 | C.11 |
| 1.1680 | B.129 | C.11 |
| 1.1681 | B.130 | C.11 |
| 1.1682 | B.131 | C.11 |
| 1.1683 | B.132 | C.11 |
| 1.1684 | B.133 | C.11 |
| 1.1685 | B.134 | C.11 |
| 1.1686 | B.135 | C.11 |
| 1.1687 | B.136 | C.11 |
| 1.1688 | B.137 | C.11 |
| 1.1689 | B.138 | C.11 |
| 1.1690 | B.139 | C.11 |
| 1.1691 | B.140 | C.11 |
| 1.1692 | B.141 | C.11 |
| 1.1693 | B.1 | C.12 |

TABLE 1-continued (herbicidal combinations 1.1 to 1.1833):

| comp. no. | herbicide B | safener C |
|---|---|---|
| 1.1694 | B.2 | C.12 |
| 1.1695 | B.3 | C.12 |
| 1.1696 | B.4 | C.12 |
| 1.1697 | B.5 | C.12 |
| 1.1698 | B.6 | C.12 |
| 1.1699 | B.7 | C.12 |
| 1.1700 | B.8 | C.12 |
| 1.1701 | B.9 | C.12 |
| 1.1702 | B.10 | C.12 |
| 1.1703 | B.11 | C.12 |
| 1.1704 | B.12 | C.12 |
| 1.1705 | B.13 | C.12 |
| 1.1706 | B.14 | C.12 |
| 1.1707 | B.15 | C.12 |
| 1.1708 | B.16 | C.12 |
| 1.1709 | B.17 | C.12 |
| 1.1710 | B.18 | C.12 |
| 1.1711 | B.19 | C.12 |
| 1.1712 | B.20 | C.12 |
| 1.1713 | B.21 | C.12 |
| 1.1714 | B.22 | C.12 |
| 1.1715 | B.23 | C.12 |
| 1.1716 | B.24 | C.12 |
| 1.1717 | B.25 | C.12 |
| 1.1718 | B.26 | C.12 |
| 1.1719 | B.27 | C.12 |
| 1.1720 | B.28 | C.12 |
| 1.1721 | B.29 | C.12 |
| 1.1722 | B.30 | C.12 |
| 1.1723 | B.31 | C.12 |
| 1.1724 | B.32 | C.12 |
| 1.1725 | B.33 | C.12 |
| 1.1726 | B.34 | C.12 |
| 1.1727 | B.35 | C.12 |
| 1.1728 | B.36 | C.12 |
| 1.1729 | B.37 | C.12 |
| 1.1730 | B.38 | C.12 |
| 1.1731 | B.39 | C.12 |
| 1.1732 | B.40 | C.12 |
| 1.1733 | B.41 | C.12 |
| 1.1734 | B.42 | C.12 |
| 1.1735 | B.43 | C.12 |
| 1.1736 | B.44 | C.12 |
| 1.1737 | B.45 | C.12 |
| 1.1738 | B.46 | C.12 |
| 1.1739 | B.47 | C.12 |
| 1.1740 | B.48 | C.12 |
| 1.1741 | B.49 | C.12 |
| 1.1742 | B.50 | C.12 |
| 1.1743 | B.51 | C.12 |
| 1.1744 | B.52 | C.12 |
| 1.1745 | B.53 | C.12 |
| 1.1746 | B.54 | C.12 |
| 1.1747 | B.55 | C.12 |
| 1.1748 | B.56 | C.12 |
| 1.1749 | B.57 | C.12 |
| 1.1750 | B.58. | C.12 |
| 1.1751 | B.59 | C.12 |
| 1.1752 | B.60 | C.12 |
| 1.1753 | B.61 | C.12 |
| 1.1754 | B.62 | C.12 |
| 1.1755 | B.63 | C.12 |
| 1.1756 | B.64 | C.12 |
| 1.1757 | B.65 | C.12 |
| 1.1758 | B.66 | C.12 |
| 1.1759 | B.67 | C.12 |
| 1.1760 | B.68 | C.12 |
| 1.1761 | B.69 | C.12 |
| 1.1762 | B.70 | C.12 |
| 1.1763 | B.71 | C.12 |
| 1.1764 | B.72 | C.12 |
| 1.1765 | B.73 | C.12 |
| 1.1766 | B.74 | C.12 |
| 1.1767 | B.75 | C.12 |
| 1.1768 | B.76 | C.12 |
| 1.1769 | B.77 | C.12 |
| 1.1770 | B.78 | C.12 |
| 1.1771 | B.79 | C.12 |
| 1.1772 | B.80 | C.12 |
| 1.1773 | B.81 | C.12 |
| 1.1774 | B.82 | C.12 |
| 1.1775 | B.83 | C.12 |
| 1.1776 | B.84 | C.12 |
| 1.1777 | B.85 | C.12 |
| 1.1778 | B.86 | C.12 |
| 1.1779 | B.87 | C.12 |
| 1.1780 | B.88 | C.12 |
| 1.1781 | B.89 | C.12 |
| 1.1782 | B.90 | C.12 |
| 1.1783 | B.91 | C.12 |
| 1.1784 | B.92 | C.12 |
| 1.1785 | B.93 | C.12 |
| 1.1786 | B.94 | C.12 |
| 1.1787 | B.95 | C.12 |
| 1.1788 | B.96 | C.12 |
| 1.1789 | B.97 | C.12 |
| 1.1790 | B.98 | C.12 |
| 1.1791 | B.99 | C.12 |
| 1.1792 | B.100 | C.12 |
| 1.1793 | B.101 | C.12 |
| 1.1794 | B.102 | C.12 |
| 1.1795 | B.103 | C.12 |
| 1.1796 | B.104 | C.12 |
| 1.1797 | B.105 | C.12 |
| 1.1798 | B.106 | C.12 |
| 1.1799 | B.107 | C.12 |
| 1.1800 | B.108 | C.12 |
| 1.1801 | B.109 | C.12 |
| 1.1802 | B.110 | C.12 |
| 1.1803 | B.111 | C.12 |
| 1.1804 | B.112 | C.12 |
| 1.1805 | B.113 | C.12 |
| 1.1806 | B.114 | C.12 |
| 1.1807 | B.115 | C.12 |
| 1.1808 | B.116 | C.12 |
| 1.1809 | B.117 | C.12 |
| 1.1810 | B.118 | C.12 |
| 1.1811 | B.119 | C.12 |
| 1.1812 | B.120 | C.12 |
| 1.1813 | B.121 | C.12 |
| 1.1814 | B.122 | C.12 |
| 1.1815 | B.123 | C.12 |
| 1.1816 | B.124 | C.12 |
| 1.1817 | B.125 | C.12 |
| 1.1818 | B.126 | C.12 |
| 1.1819 | B.127 | C.12 |
| 1.1820 | B.128 | C.12 |
| 1.1821 | B.129 | C.12 |
| 1.1822 | B.130 | C.12 |
| 1.1823 | B.131 | C.12 |
| 1.1824 | B.132 | C.12 |
| 1.1825 | B.133 | C.12 |
| 1.1826 | B.134 | C.12 |
| 1.1827 | B.135 | C.12 |
| 1.1828 | B.136 | C.12 |
| 1.1829 | B.137 | C.12 |
| 1.1830 | B.138 | C.12 |
| 1.1831 | B.139 | C.12 |
| 1.1832 | B.140 | C.12 |
| 1.1833 | B.141 | C.12 |

The specific number for each single combination is deductible as follows

Combination 1.777 for example comprises the composition A, flumioxazin (B.72) and fenclorim (C.5) (see table 1, entry 1.777; as well as table B, entry B.72 and table C, entry C.5). Combination 7.777 for example comprises imazaquin (B32) (see the definition for combinations 7.1 to 7.1692 below), and the composition A, flumioxazin (B.72) and fenclorim (C.5) (see table 1, entry 1.777; as well as table B, entry B.77 and table C, entry C.5).

Also especially preferred are combinations 2.1 to 2.1833, which differ from the corresponding combinations 1.1 to 1.1833 only in that they additionally comprise B.2 as further herbicide B.

Also especially preferred are combinations 3.1 to 3.1833, which differ from the corresponding combinations 1.1 to 1.1833 only in that they additionally comprise B.7 as further herbicide B.

Also especially preferred are combinations 4.1 to 4.1833, which differ from the corresponding combinations 1.1 to 1.1833 only in that they additionally comprise B.29 as further herbicide B.

Also especially preferred are combinations 5.1 to 5.1833, which differ from the corresponding combinations 1.1 to 1.1833 only in that they additionally comprise B.30 as further herbicide B.

Also especially preferred are combinations 6.1 to 6.1833, which differ from the corresponding combinations 1.1 to 1.1833 only in that they additionally comprise B.31 as further herbicide B.

Also especially preferred are combinations 7.1 to 7.1833, which differ from the corresponding combinations 1.1 to 1.1833 only in that they additionally comprise B.32 as further herbicide B.

Also especially preferred are combinations 8.1 to 8.1833, which differ from the corresponding combinations 1.1 to 1.1833 only in that they additionally comprise B.33 as further herbicide B.

Also especially preferred are combinations 9.1 to 9.1833, which differ from the corresponding combinations 1.1 to 1.1833 only in that they additionally comprise B.40 as further herbicide B.

Also especially preferred are combinations 10.1 to 10.1833, which differ from the corresponding combinations 1.1 to 1.1833 only in that they additionally comprise B.44 as further herbicide B.

Also especially preferred are combinations 11.1 to 11.1833, which differ from the corresponding combinations 1.1 to 1.1833 only in that they additionally comprise B.45 as further herbicide B.

Also especially preferred are combinations 12.1 to 12.1833, which differ from the corresponding combinations 1.1 to 1.1833 only in that they additionally comprise B.52 as further herbicide B.

Also especially preferred are combinations 13.1 to 13.1833, which differ from the corresponding combinations 1.1 to 1.1833 only in that they additionally comprise B.53 as further herbicide B.

Also especially preferred are combinations 14.1 to 14.1833, which differ from the corresponding combinations 1.1 to 1.1833 only in that they additionally comprise B.54 as further herbicide B.

Also especially preferred are combinations 15.1 to 15.1833, which differ from the corresponding combinations 1.1 to 1.1833 only in that they additionally comprise B.55 as further herbicide B.

Also especially preferred are combinations 16.1 to 16.1833, which differ from the corresponding combinations 1.1 to 1.1833 only in that they additionally comprise B.56 as further herbicide B.

Also especially preferred are combinations 17.1 to 17.1833, which differ from the corresponding combinations 1.1 to 1.1833 only in that they additionally comprise B.57 as further herbicide B.

Also especially preferred are combinations 18.1 to 18.1833, which differ from the corresponding combinations 1.1 to 1.1833 only in that they additionally comprise B.60 as further herbicide B.

Also especially preferred are combinations 19.1 to 19.1833, which differ from the corresponding combinations 1.1 to 1.1833 only in that they additionally comprise B.65 as further herbicide B.

Also especially preferred are combinations 20.1 to 20.1833, which differ from the corresponding combinations 1.1 to 1.1833 only in that they additionally comprise B.66 as further herbicide B.

Also especially preferred are combinations 21.1 to 21.1833, which differ from the corresponding combinations 1.1 to 1.1833 only in that they additionally comprise B.69 as further herbicide B.

Also especially preferred are combinations 22.1 to 22.1833, which differ from the corresponding combinations 1.1 to 1.1833 only in that they additionally comprise B.72 as further herbicide B.

Also especially preferred are combinations 23.1 to 23.1833, which differ from the corresponding combinations 1.1 to 1.1833 only in that they additionally comprise B.73 as further herbicide B.

Also especially preferred are combinations 24.1 to 24.1833, which differ from the corresponding combinations 1.1 to 1.1833 only in that they additionally comprise B.76 as further herbicide B.

Also especially preferred are combinations 25.1 to 25.1833, which differ from the corresponding combinations 1.1 to 1.1833 only in that they additionally comprise B.77 as further herbicide B.

Also especially preferred are combinations 26.1 to 26.1833, which differ from the corresponding combinations 1.1 to 1.1833 only in that they additionally comprise B.80 as further herbicide B.

Also especially preferred are combinations 27.1 to 27.1833, which differ from the corresponding combinations 1.1 to 1.1833 only in that they additionally comprise B.81 as further herbicide B.

Also especially preferred are combinations 28.1 to 28.1833, which differ from the corresponding combinations 1.1 to 1.1833 only in that they additionally comprise B.84 as further herbicide B.

Also especially preferred are combinations 29.1 to 29.1833, which differ from the corresponding combinations 1.1 to 1.1833 only in that they additionally comprise B.84 and B.54 as further herbicides B.

Also especially preferred are combinations 30.1 to 30.1833, which differ from the corresponding combinations 1.1 to 1.1833 only in that they additionally comprise B.84 and B.60 as further herbicides B.

Also especially preferred are combinations 31.1 to 31.1833, which differ from the corresponding combinations 1.1 to 1.1833 only in that they additionally comprise B.84 and B.66 as further herbicides B.

Also especially preferred are combinations 32.1 to 32.1833, which differ from the corresponding combinations 1.1 to 1.1833 only in that they additionally comprise B. 85 as further herbicide B.

Also especially preferred are combinations 33.1 to 33.1833, which differ from the corresponding combinations 1.1 to 1.1833 only in that they additionally comprise B. 85 and B.54 as further herbicides B.

Also especially preferred are combinations 34.1 to 34.1833, which differ from the corresponding combinations Also especially preferred are combinations 35.1 to 35.1833, which differ from the corresponding combinations 1.1 to 1.1833 only in that they additionally comprise B. 85 and B.66 as further herbicides B.

Also especially preferred are combinations 36.1 to 36.1833, which differ from the corresponding combinations 1.1 to 1.1833 only in that they additionally comprise B.87 as further herbicide B.

Also especially preferred are combinations 37.1 to 37.1833, which differ from the corresponding combinations 1.1 to 1.1833 only in that they additionally comprise B. 88 as further herbicide B.

Also especially preferred are combinations 38.1 to 38.1833, which differ from the corresponding combinations 1.1 to 1.1833 only in that they additionally comprise B. 88 and B.54 as further herbicides B.

Also especially preferred are combinations 39.1 to 39.1833, which differ from the corresponding combinations 1.1 to 1.1833 only in that they additionally comprise B. 88 and B.60 as further herbicides B.

Also especially preferred are combinations 40.1 to 40.1833, which differ from the corresponding combinations 1.1 to 1.1833 only in that they additionally comprise B. 88 and B.66 as further herbicides B.

Also especially preferred are combinations 41.1 to 41.1833, which differ from the corresponding combinations 1.1 to 1.1833 only in that they additionally comprise B.90 as further herbicide B.

Also especially preferred are combinations 42.1 to 42.1833, which differ from the corresponding combinations 1.1 to 1.1833 only in that they additionally comprise B.91 as further herbicide B.

Also especially preferred are combinations 43.1 to 43.1833, which differ from the corresponding combinations 1.1 to 1.1833 only in that they additionally comprise B.91 and B.54 as further herbicides B.

Also especially preferred are combinations 44.1 to 44.1833, which differ from the corresponding combinations 1.1 to 1.1833 only in that they additionally comprise B.91 and B.60 as further herbicides B.

Also especially preferred are combinations 45.1 to 45.1833, which differ from the corresponding combinations 1.1 to 1.1833 only in that they additionally comprise B.91 and B.66 as further herbicides B.

Also especially preferred are combinations 46.1 to 46.1833, which differ from the corresponding combinations 1.1 to 1.1833 only in that they additionally comprise B.95 as further herbicide B.

Also especially preferred are combinations 47.1 to 47.1833, which differ from the corresponding combinations 1.1 to 1.1833 only in that they additionally comprise B.95 and B.54 as further herbicides B.

Also especially preferred are combinations 48.1 to 48.1833, which differ from the corresponding combinations 1.1 to 1.1833 only in that they additionally comprise B.95 and B.76 as further herbicides B.

Also especially preferred are combinations 49.1 to 49.1833, which differ from the corresponding combinations 1.1 to 1.1833 only in that they additionally comprise B.95 and B.84 as further herbicides B.

Also especially preferred are combinations 50.1 to 50.1833, which differ from the corresponding combinations 1.1 to 1.1833 only in that they additionally comprise B.95 and B.103 as further herbicides B.

Also especially preferred are combinations 51.1 to 51.1833, which differ from the corresponding combinations 1.1 to 1.1833 only in that they additionally comprise B.95 and B.85 as further herbicides B.

Also especially preferred are combinations 52.1 to 52.1833, which differ from the corresponding combinations 1.1 to 1.1833 only in that they additionally comprise B.95 and B.88 as further herbicides B.

Also especially preferred are combinations 53.1 to 53.1833, which differ from the corresponding combinations 1.1 to 1.1833 only in that they additionally comprise B.95 and B.91 as further herbicides B.

Also especially preferred are combinations 54.1 to 54.1833, which differ from the corresponding combinations 1.1 to 1.1833 only in that they additionally comprise B.98 as further herbicide B.

Also especially preferred are combinations 55.1 to 55.1833, which differ from the corresponding combinations 1.1 to 1.1833 only in that they additionally comprise B.101 as further herbicide B.

Also especially preferred are combinations 56.1 to 56.1833, which differ from the corresponding combinations 1.1 to 1.1833 only in that they additionally comprise B.103 as further herbicide B.

Also especially preferred are combinations 57.1 to 57.1833, which differ from the corresponding combinations 1.1 to 1.1833 only in that they additionally comprise B.106 as further herbicide B.

Also especially preferred are combinations 58.1 to 58.1833, which differ from the corresponding combinations 1.1 to 1.1833 only in that they additionally comprise B.107 as further herbicide B.

Also especially preferred are combinations 59.1 to 59.1833, which differ from the corresponding combinations 1.1 to 1.1833 only in that they additionally comprise B.108 as further herbicide B.

Also especially preferred are combinations 60.1 to 60.1833, which differ from the corresponding combinations 1.1 to 1.1833 only in that they additionally comprise B.110 as further herbicide B.

Also especially preferred are combinations 61.1 to 61.1833, which differ from the corresponding combinations 1.1 to 1.1833 only in that they additionally comprise B.112 as further herbicide B.

Also especially preferred are combinations 62.1 to 62.1833, which differ from the corresponding combinations 1.1 to 1.1833 only in that they additionally comprise B.113 as further herbicide B.

Also especially preferred are combinations 63.1 to 63.1833, which differ from the corresponding combinations 1.1 to 1.1833 only in that they additionally comprise B.117 as further herbicide B.

Also especially preferred are combinations 64.1 to 64.1833, which differ from the corresponding combinations 1.1 to 1.1833 only in that they additionally comprise B.119 as further herbicide B.

Also especially preferred are combinations 65.1 to 65.1833, which differ from the corresponding combinations 1.1 to 1.1833 only in that they additionally comprise B.120 as further herbicide B.

Also especially preferred are combinations 66.1 to 66.1833, which differ from the corresponding combinations 1.1 to 1.1833 only in that they additionally comprise B.122 as further herbicide B.

Also especially preferred are combinations 67.1 to 67.1833, which differ from the corresponding combinations 1.1 to 1.1833 only in that they additionally comprise B.123 as further herbicide B.

Also especially preferred are combinations 68.1 to 68.1833, which differ from the corresponding combinations 1.1 to 1.1833 only in that they additionally comprise B.130 as further herbicide B.

Also especially preferred are combinations 69.1 to 69.12 comprising the composition A, and as further compound the substance as defined in the respective row of table C

TABLE C

| comp. no. | safener C |
|---|---|
| 69.1 | C.1 |
| 69.2 | C.2 |
| 69.3 | C.3 |
| 69.4 | C.4 |
| 69.5 | C.5 |
| 69.6 | C.6 |
| 69.7 | C.7 |
| 69.8 | C.8 |
| 69.9 | C.9 |
| 69.10 | C.10 |
| 69.11 | C.11 |
| 69.12 | C.12 |

According to one embodiment of the invention, in the ready-to-use preparations of combinations according to the invention in the form of plant protection agents, the components A (composition A) and B and/or C can be present formulated jointly or separately in suspended, emulsified or dissolved form. The use forms depend entirely on the intended applications.

Accordingly, a first embodiment of the invention relates to combinations in the form of a plant protection agent formulated as a 1-component combination comprising the composition A and at least one further active compound selected from the herbicides B and the safeners C and also a solid or liquid carrier and, if appropriate, one or more surfactants.

Accordingly, a second embodiment of the invention relates to combinations in the form of a plant protection agent formulated as a 2-component combination comprising a first formulation (component) comprising the composition A, a solid or liquid carrier and, if appropriate, one or more surfactants, and a second component comprising at least one further active compound selected from the herbicides B and safeners C, a solid or liquid carrier and, if appropriate, one or more surfactants.

The composition A and the at least one further active compound B and/or C can be applied jointly or separately, simultaneously or in succession, before, during or after the emergence of the plants. The order of the application of the components A, B and/or C is of minor importance. The only thing that is important is that the composition A and at least one further active component B and/or C are present simultaneously at the site of action, i.e. are at the same time in contact with or taken up by the plant to be controlled.

The required application rate of component B and, if appropriate, C without formulation auxiliaries depends on the structure of the plant stand, on the development stage of the plants, on the climatic conditions at the site of use and on the application technique. In general, the application rate of B and, if appropriate, C, is from 0.001 to 3 kg/ha, preferably from 0.005 to 2.5 kg/ha and in particular from 0.01 to 2 kg/ha of active substance (a.s.).

The required application rates of component B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of component C are generally in the range of from 0.0005 kg/ha to 2.5 kg/ha and preferably in the range of from 0.005 kg/ha to 2 kg/ha or 0.01 kg/ha to 1.5 kg/h of a.s.

The combinations according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal combinations may also be applied by the low-volume or the ultra-low-volume method, or in the form of microgranules.

The combinations according to the invention can be applied pre- or post-emergence, or together with the seed of a crop plant. It is also possible to apply the combinations by applying seed, pretreated with a combination of the invention, of a crop plant. If the active components A and B and, if appropriate C, are less well tolerated by certain crop plants, application techniques may be used in which the herbicidal combinations are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

The following illustrations and examples serve to illustrate the invention and should not be regarded as limiting.

The particle size distribution has been determined by light scattering on a Malvern Mastersizer 2000 from Malvern Instruments Ldt. according to the European norm ISO 13320 using the Mie scattering model.

EXAMPLE 1

Reference

A suspension made of 422 parts per weight water, 60 parts propylene glycol, 167 parts Pluronic® PE 10500 18% Solution, 20 parts Tamol® DN, 2.5 parts Wacker Silicon SRE-PFL and 508 parts crystalline benzoxazinone (I) of modification A was circulated through a beadI mill until $x_{80} < 2$ µm. Subsequently, a suspension of 10 parts propylene glycol, 3 parts Rhodopol® G, 3 parts water, 2 parts Acticide® MBS and 2.5 parts Wacker Silicon SRE-PFL was added yielding a suspension concentrate (SC) containing 500 g/L benzoxazinone (I).

The particle sizes according to laser scattering were $x_{10} = 0.5$ µm, $x_{50} = 1.0$ µm, $x_{90} = 2.3$ µm; $x_{95} = 3.0$ µm (i.e. 95% per volume<3 µm), $x_{99} = 5.0$ µm (i.e. 99% per volume<5 µm) and no detectable particles above 45 µm.

EXAMPLE 2

Using the same recipe like in example 1 a suspension concentrate containing 500 g/L crystalline benzoxazinone (I) of modification A was manufactured, but instead of a bead mill a mechanical crushing mill was used.

In this SC formulation the particles are characterized as follows $x_{10} = 1.0$ µm, $x_{50} = 5.3$ µm, $x_{90} = 49$ µm, $x_{39} = 3.0$ µm (i.e. 39% per volume<3 µm), $x_{49} = 5.0$ µm (i.e. 49% per volume<5 µm) and $x_{88} = 45.0$ µm (i.e. 12% per volume>45 µm).

EXAMPLE 3

Using the same recipe like in example 1 a suspension concentrate containing 500 g/L crystalline benzoxazinone (I) of modification A was manufactured, but instead of a bead mill a rotor stator system was used.

In this SC formulation the particles are characterized as follows $x_{10}=1.1$ µm, $x_{50}=7.8$ µm, $x_{90}=38$ µm, $x_{30}=3.0$ µm (i.e. 30% per volume<3 µm), $x_{40}=5.0$ µm (i.e. 40% per volume<5 µm) and $x_{93}=45.0$ µm (i.e. 7% per volume>45 µm).

Preparation of Form a of Benzoxazinone (I) by Crystallization from a Solution in an Organic Solvent with Evaporation

EXAMPLES 4.1 TO 4.10

50 mg of benzoxazinone (I) were dissolved in 2-3 ml of the respective solvent in a test vessel. The test vessel was placed in a greenhouse and a nitrogen flow (5 l/min) was passed over the surface of the solvent. In this manner, benzoxazinone (I) was obtained in the form of small crystalline rods, which were isolated and analyzed by X-ray powder diffraction (XRPD). On the basis of the characteristic reflections, form A was identified.

TABLE 1

| Example | Solvent | Form | Crystal form |
| --- | --- | --- | --- |
| 4.1 | ethylbenzene | A | small rods |
| 4.2 | dichlorobenzene | A | small rods |
| 4.3 | chlorobenze | A | small rods |
| 4.4 | p-xylene | A | small rods |
| 4.5 | acetone | A | small rods |
| 4.6 | methylethylketone | A | small rods |
| 4.7 | methylbutylketone | A | small rods |
| 4.8 | methanol | A | small rods |
| 4.9 | ethanol | A | small rods |
| 4.10 | isopropanol | A | small rods |

Preparation of Form a of Benzoxazinone (I) by Crystallization from a Slurry in a Mixture of Water and Organic Solvent

EXAMPLE 4.11

A mixture of forms A and B of benzoxazinone (I), obtained by comparative example 1 (500 mg) were suspended in 3 ml of a mixture of water and Ethanol (11 v/v) and the slurry was stirred for 48 h at 23° C. A slurry of crystalline material was obtained, which was filtered and analysed by XRPD and DSC. The obtained material was pure form A of benzoxazinone (I).

EXAMPLE 4.12

Form B of benzoxazinone (I), obtained by example 16 (500 mg) were suspended in 3 ml of a mixture of water and tetrahydrofurane (11 v/v) and the slurry was stirred for 48 h at 23° C. A slurry of crystalline material was obtained, which was filtered and analysed by XRPD and DSC. The obtained material was pure form A of benzoxazinone (I).

EXAMPLE 4.13

A mixture forms A and B of benzoxazinone (I), obtained by comparative example 1 (500 mg) were suspended in 3 ml of a mixture of toluene and the slurry was stirred for 48 h at 23° C. A slurry of crystalline material was obtained, which was filtered and analysed by XRPD and DSC. The obtained material was pure form A of benzoxazinone (I).

EXAMPLE 4.14

A mixture forms A and B of benzoxazinone (I), obtained by comparative example 1 (500 mg) were suspended in 3 ml of a mixture of water and 1,3-propanediol (11 v/v) and the slurry was stirred for 48 h at 23° C. A slurry of crystalline material was obtained, which was filtered and analysed by XRPD and DSC. The obtained material was pure form A of benzoxazinone (I).

Preparation of Form B of Benzoxazinone (I) by Crystallization from a Slurry in a Mixture of Water and Organic Solvent

EXAMPLE 4.15

Form A of benzoxazinone (I), obtained by example 12 (500 mg) were suspended in 3 ml of a mixture of water and ethanol (11 v/v) and the slurry was stirred for 48 h at 90° C. A slurry of crystalline material was obtained, which was filtered and analysed by XRPD and DSC. The obtained material was pure form B of benzoxazinone (I).

EXAMPLE 4.16

A mixture forms A and B of benzoxazinone (I), obtained by comparative example 1 (500 mg) were suspended in 3 ml of a mixture of water and 1,3-propanediol (11 v/v) and the slurry was stirred for 48 h at 90° C. A slurry of crystalline material was obtained, which was filtered and analysed by PXRD and DSC. The obtained material was pure form B of benzoxazinone (I).

Preparation of Form B of Benzoxazinone (I) by Crystallization from a Solution in an Organic Solvent with Evaporation

EXAMPLE 4.17

50 mg of benzoxazinone (I) were dissolved in 2-3 ml of toluene in a test vessel. The test vessel placed in a greenhouse and heated to 95° C. and a nitrogen flow (5 l/min) was passed over the surface of the solvent. In this manner, benzoxazinone (I) was obtained in the form of small crystalline plates, which were isolated and analyzed by X-ray powder diffraction (XRPD). On the basis of the characteristic reflections, form B was identified.

Preparation of Form B of Benzoxazinone (I) by Heating Form A

EXAMPLE 4.18

500 mg of form A of benzoxazinone (I), obtained by example 12 were placed into an open vessel. The vessel was purged with nitrogen and sealed and then heated to 180° C. for 2 h. The obtained material was isolated and analyzed by X-ray powder diffraction (XRPD). On the basis of the characteristic reflections, form B was identified.

Preparation of a Mixture of Forms A and B of Benzoxazinone (I)

50 mg of benzoxazinone (I) were dissolved in 2-3 ml of the respective solvent (e.g. 1-butanol, isobutanol) in a test vessel. The test vessel was placed in a greenhouse and heated to 90° C. A nitrogen flow (5 l/min) was passed over the surface of the solvent. In this manner, benzoxazinone (I)

was obtained in the form of small crystalline rods, which were isolated and analyzed by X-ray powder diffraction (XRPD). On the basis of the characteristic reflections, a mixture of forms A and B was identified.

FIG. 1 shows an X-ray powder diffraction diagram of form A. The X-ray diffraction diagram of form A was recorded by using Panalytical X'Pert Pro diffractometer (manufacturer Panalytical) in reflection geometry in the range from 2θ=3°–35° with increments of 0.0167° C. using Cu-Kα radiation (at 25° C.). The recorded 2θ values were used to calculate the stated interplanar spacings d. The intensity of the peaks (y-axis linear intensity counts) is plotted versus the 2θ angle (x-axis in degrees 2θ).

Figure 1:
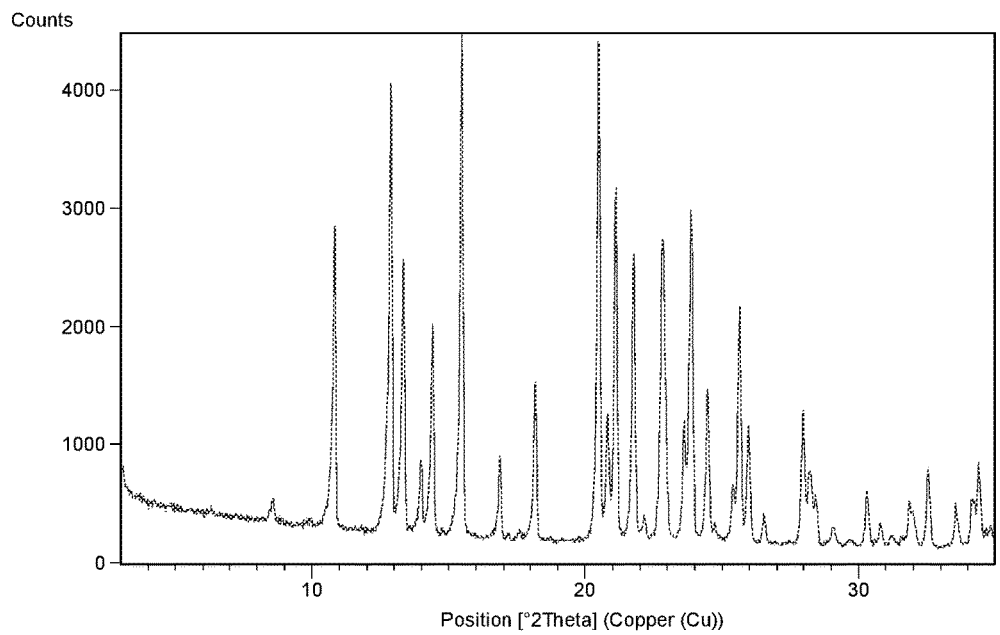
Figure 2:
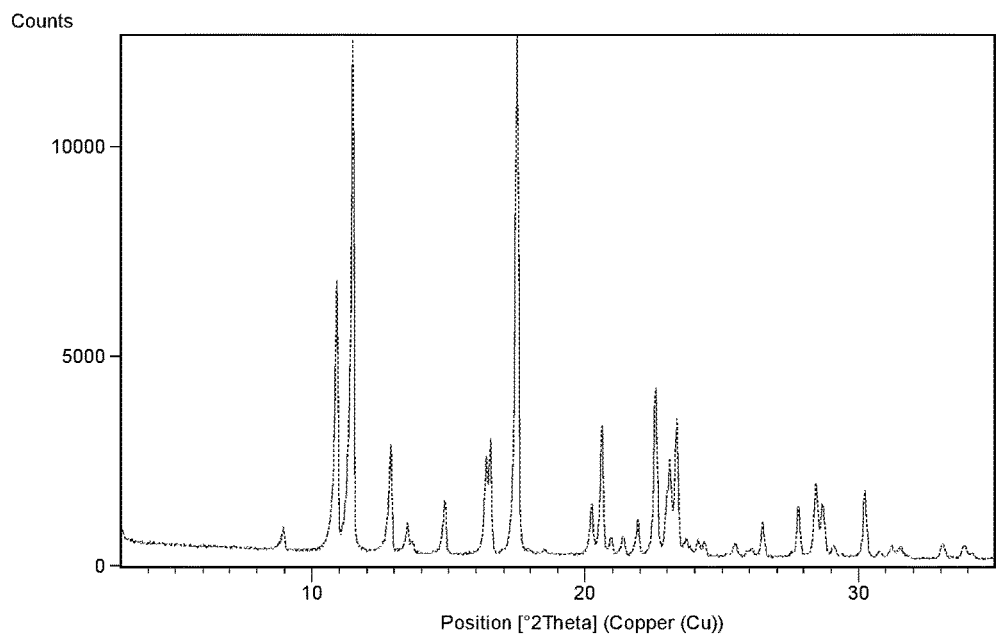
FIG. 2 shows an X-ray powder diffraction diagram of form B. The X-ray diffraction diagram was recorded under the conditions stated for FIG. 1.
Figure 3:
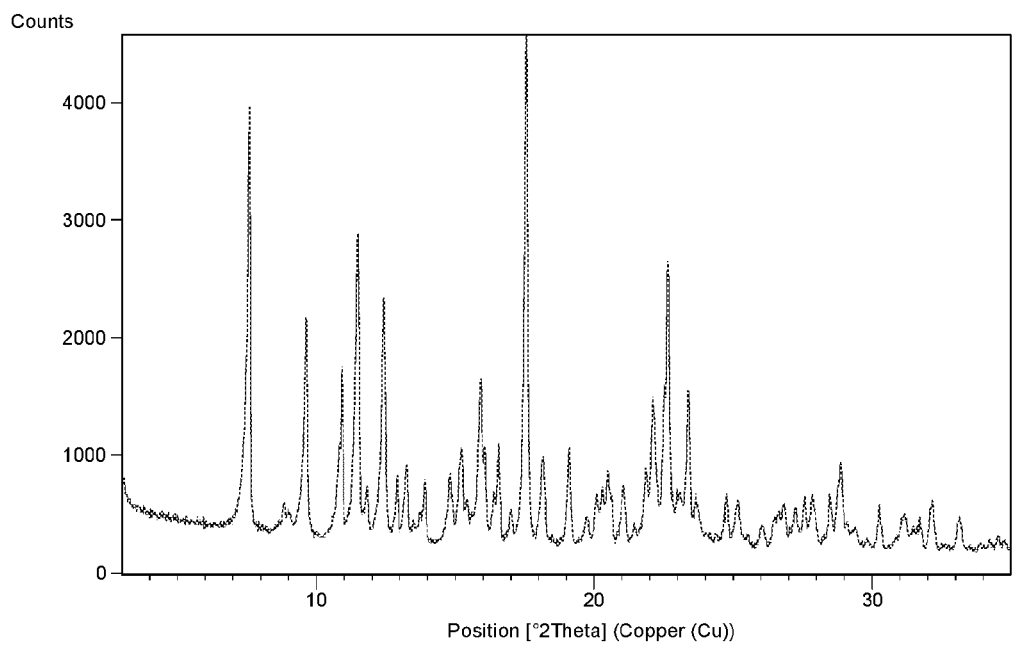
FIG. 3 shows an X-ray powder diffraction diagram of a mixture of forms A+B+C. The X-ray diffraction diagram was recorded under the conditions stated for FIG. 1.

The single crystal X-ray diffraction data of Form A was collected on a Bruker AXS CCD Detector using graphite Cu-Kα radiation (at −173° C.). The structure was solved using direct methods, refined and expanded by using Fourier techniques with SHELX software package (G. M. Sheldrick, SHELX-97, University of Göttingen, 1997). Absorption correction was performed with SADABS software.

DSC was performed on a Mettler Toledo DSC 822e module. The samples were placed in crimped but vented aluminium pans. The samples size in each case was 5 to 10 mg. The thermal behaviour was analized in the range 30-250° C. The heating rate was 5° C./min. The samples were purged with a stream of nitrogen flowing at 150 ml/during the experiment. Melting points values were confirmed by a Mettler Hot Stage in combination with a light microscope.

Use Examples

Greenhouse Test

The herbicidal action of the composition A and combinations according to the invention was demonstrated by the following greenhouse experiments The culture containers used were trays, consisting of individually separated plastic pots (each approx. 4 cm in diameter) containing loamy sand with approximately 2.5% of organic matter as substrate. The seeds of the test plants were sown separately for each species, one seed per pot was used for corn (ZEAMX), the grass species (SETFA) was broadcasted over the pot and covered with a thin layer of soil.

For the pre-emergence treatment, the active compounds in the form of the respective suspension concentrate were diluted to comply with a rate of 50 g/ha benzoxazinone (I) and 200 l/ha water, and subsequently applied directly after sowing by drip application. A pipette was used, in total per pot a volume of 2 ml was applied. The containers were irrigated gently to promote germination and growth and subsequently covered with transparent plastic hoods until the plants had rooted. This cover caused uniform germination of the test plants unless this was adversely affected by the active compounds.

The plants were kept at 15-35° C. in the glasshouse.

The test period was approx. 10 days. During this time, the plants were tended and their response to the individual treatments was evaluated.

Evaluation was carried out using a scale from 0 to 100. 100 means no emergence of the plants, or complete destruction of at least the above-ground parts, and 0 means no damage or normal course of growth. A good herbicidal activity is given at values of at least 60, and very good herbicidal activity is given at values of at least 85. In parallel the crop injury/phytotoxicity was evaluated. The activity—selectivity window was calculated as quotient of activity and phytotoxicity obtained in the test.

A selectivity is present if the damage to the crop plant caused by the composition of benzoxazinone (I) according to the present invention is less compared to the damage caused by application of a benzoxazinone (I), wherein the particle size distribution is not according to that according to the present invention.

EXAMPLE 5

Herbicidal Action of the Pre-Emergence Applied Benzoxazinone (I) Against SETFA and Selectivity with Regard to Corn 10 Days after Treatment in the Greenhouse

| benzoxazinone (I) | application rate [g/ha] | damage to corn | herbicidal action against SETFA | Safety window |
|---|---|---|---|---|
| reference example 1 | 50 | 60 | 88 | 1.47 |
| example 2 | 50 | 18 | 83 | 4.61 |

In this example, benzoxazinone (I) was formulated as a 500 g/l SC.

Prior to application, the formulated benzoxazinone (I) was diluted into water and the aqueous solution was used for the drip application.

Field Test

The herbicidal action of the composition A and combinations according to the invention was demonstrated by the following field experiments A field trial was performed on a loamy sand soil with approximately 1.5-2.5% of organic matter.

The test plants were sown separately for each species in rows, as crop corn (ZEAMX) was planted, as indicator weed species Brassica (BRSNW) was planted according to field trial practice.

For the pre-emergence treatment, the active compounds, suspended in water, were applied directly after sowing by means of finely distributing nozzles. 200 g/ha benzoxazinone (I) in the form of the respective SC formulations were diluted with 200 l/ha water for application.

To ensure adequate activation the plots were irrigated after the application with 15 mm of water. The test period was during the whole growing period of corn. After 19 days after application the response of the crop and the activity on the indicator weed species to the individual treatments were evaluated.

Evaluation was carried out using a scale from 0 to 100. 100 means no emergence of the plants, or complete destruction of at least the above-ground parts, and 0 means no damage or normal course of growth. A good herbicidal activity is given at values of at least 60, and very good herbicidal activity is given at values of at least 85. In parallel the crop injury/phytotoxicity was evaluated. The activity—selectivity window was calculated as quotient of activity and phytotoxicity obtained in the test.

A safener action is present if the damage to the crop plant caused by the composition of benzoxazinone (I) according to the present invention is less compared to the damage caused by application of a benzoxazinone (I), wherein the particle size distribution is not according to that according to the present invention.

EXAMPLE 6

Herbicidal Action of the Pre-Emergence Applied Benzoxazinone (I) Against SETFA and Selectivity with Regard to Corn 19 Days after Treatment

| benzoxazinone (I) | application rate [g/ha] | damage to corn | herbicidal action against SETFA | Safety window |
|---|---|---|---|---|
| reference example 1 | 100 | 7 | 93 | 13.29 |
| example 3 | 100 | 4 | 93 | 23.25 |

The invention claimed is:
1. A composition of benzoxazinone (I),

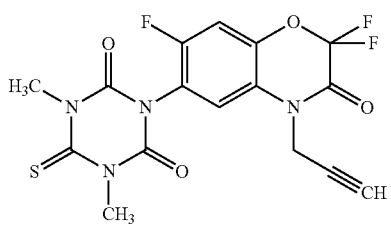

(I)

comprising the benzoxazinone (I) in form of particles, wherein at most 50% per volume of the particles have a diameter below 3 μm.

2. The composition according to claim 1, wherein at most 60% per volume of the particles have a diameter below 5 μm.

3. The composition according to claim 1, wherein at most 35% per volume of the particles have a diameter below 3 μm.

4. The composition according to claim 1, wherein at least 90% wt. % of the particles are crystalline.

5. The composition according to claim 1, wherein the particles are present in the crystalline form A.

6. The composition of claim 1, wherein at most 15% per volume of the particles have a diameter above 45 μm.

7. A plant protection agent comprising the composition as claimed in claim 1, and water.

8. A plant protection agent comprising a herbicidally active amount of a composition of benzoxazinone (I) as claimed in claim 1 and at least one inert liquid and/or solid carrier and, optionally, at least one surface-active substance.

9. A plant protection agent as claimed in claim 8 in form of a suspension concentrate (SC), oil-dispersion (OD), wettable powder (WP) and/or wettable granule (WG).

10. A process for the preparation of a plant protection agent, which comprises mixing an herbicidally active amount of a composition of benzoxazinone (I) as claimed in claim 1 and water.

11. A process for the preparation of a plant protection agent, which comprises mixing an herbicidally active amount of a composition of benzoxazinone (I) as claimed in claim 1 and at least one inert liquid and/or solid carrier and, optionally, at least one surface-active substance.

12. A method of controlling undesired vegetation in crops, which comprises allowing an herbicidally active amount of a composition of benzoxazinone (I) as claimed in claim 1 to act on plants, their environment or on seed.

13. The method of claim 12, wherein at most 60% per volume of the particles have a diameter below 5 μm.

14. The method of claim 12, wherein at most 35% per volume of the particles have a diameter below 3 μm.

15. The method of claim 12, wherein at least 90% wt. % of the particles are crystalline.

16. The method of claim 12, wherein the particles are present in the crystalline form A.

17. A method of safening crops from phytotoxic injury from application of a herbicidally effective amount of a benzoxazinone (I),

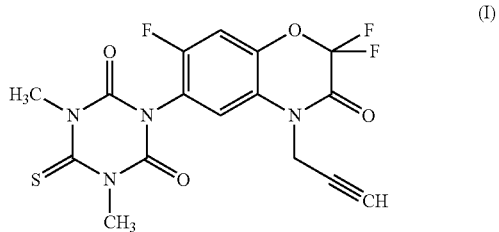 [SMILES: C#CCN1C(=O)C(F)(F)Oc2cc(F)c(-n3c(=O)n(C)c(=S)n(C)c3=O)cc21]

(I)

which comprises applying the composition of claim 1.

18. The method according to claim 17, wherein the crop plant is selected from the group consisting of *Avena sativa, Glycine max, Gossypium hirsutum, Gossypium arboreum, Gossypium herbaceum, Gossypium vitifolium, Helianthus annuus, Hordeum vulgare, Lens culinaris, Linum usitatissimum, Oryza sativa, Phaseolus lunatus, Phaseolus vulgaris, Pisum sativum, Saccharum officinarum, Secale cereale, Sorghum bicolor, Triticale, Triticum aestivum, Triticum durum, Vicia faba,* and *Zea mays*.

* * * * *